US008999666B2

(12) United States Patent
Reed et al.

(10) Patent No.: US 8,999,666 B2
(45) Date of Patent: Apr. 7, 2015

(54) PKC LIGANDS AND POLYNUCLEOTIDES ENCODING PKC LIGANDS

(75) Inventors: Thomas D. Reed, Blacksburg, VA (US); Amy H. Atzel, Minneapolis, MN (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 11/836,563

(22) Filed: Aug. 9, 2007

(65) Prior Publication Data
US 2008/0051360 A1 Feb. 28, 2008

Related U.S. Application Data

(60) Provisional application No. 60/821,958, filed on Aug. 9, 2006.

(51) Int. Cl.
*C12P 21/06* (2006.01)
*C12N 15/00* (2006.01)
*C12N 1/20* (2006.01)
*C12N 15/62* (2006.01)
*C07K 7/06* (2006.01)
*C07K 7/08* (2006.01)

(52) U.S. Cl.
CPC . *C12N 15/62* (2013.01); *C07K 7/06* (2013.01); *C07K 7/08* (2013.01); *C07K 2319/01* (2013.01)

(58) Field of Classification Search
CPC ....... C12N 1/00; C12N 15/00; C12N 2330/50
USPC ........................... 435/69.1, 320.1, 252.3, 70.1
See application file for complete search history.

(56) References Cited

U.S. PATENT DOCUMENTS

| 7,071,295 | B2 | 7/2006 | Reed |
| 2004/0185556 | A1 | 9/2004 | Reed |
| 2008/0032947 | A1 | 2/2008 | Reed |
| 2008/0050808 | A1 | 2/2008 | Reed et al. |
| 2008/0213834 | A1 | 9/2008 | Reed et al. |
| 2008/0220475 | A1 | 9/2008 | Reed et al. |
| 2009/0186379 | A1 | 7/2009 | Reed |
| 2009/0215173 | A1 | 8/2009 | Reed |
| 2009/0215866 | A1 | 8/2009 | Reed |

FOREIGN PATENT DOCUMENTS

| WO | WO 2005/040336 | A2 | 5/2005 |
| WO | WO 2005/116231 | A1 | 12/2005 |
| WO | WO 2007/047342 | * | 4/2007 |
| WO | WO 2007/048103 | A2 | 4/2007 |
| WO | WO 2007/076166 | A2 | 7/2007 |
| WO | WO 2008/119058 | A2 | 10/2008 |

OTHER PUBLICATIONS

Voet et al., Biochemistry John Wiley and Sons, 1990, p. 126-128.*
Kimchi-Sarfaty C et al., A "silent" polymorphism in the MDR1 gene changes substrate specificity.Science. Jan. 26, 2007;315(5811):525-8.*
Ngo, in The Protein Folding Problem and Tertiary Structure Prediction, Merz et al. (eds.), Birkhauser Boston: Boston, MA, pp. 433 and 492-495, 1994.*
Ahmed S et al., Protein kinase Ctheta activity is involved in the 2,3,7,8-tetrachlorodibenzo-p-dioxin-induced signal transduction pathway leading to apoptosis in L-MAT, a human lymphoblastic T-cell line, Febs J, (2005), 272:903-15.
Anthonsen MW et al., Atypical lambda/iota PKC conveys 5-lipoxygenase/leukotriene B4-mediated cross-talk between phospholipase A2s regulating NF-kappa B activation in response to tumor necrosis factor-alpha and interleukin-1beta, J Biol Chem, (2001), 276:35344-51.
Behn-Krappa A et al., The hydrophobic phosphorylation motif of conventional protein kinase C is regulated by autophosphorylation, Curr Biol, (1999), 9:728-37.
Burchfield JG et al., Akt mediates insulin-stimulated phosphorylation of Ndrg2: evidence for cross-talk with protein kinase C theta, J Biol Chem, (2004), 279:18623-32.
Buther K et al., KIBRA is a novel substrate for protein kinase Czeta, Biochem Biophys Res Commun, (2004), 317:703-7.
Cenni V et al., Regulation of novel protein kinase C epsilon by phosphorylation, Biochem J, (2002), 363:537-45.
Edlund M et al., Characterization of protein kinase C-mediated phosphorylation of the short cytoplasmic domain isoform of C-CAM, FEBS Lett, (1998), 425:166-70.
Eichholtz T et al., A myristoylated pseudosubstrate peptide, a novel protein kinase C inhibitor, J Biol Chem, (1993), 268:1982-6.
Ho MK et al., Functional role of amino-terminal serine16 and serine27 of G alphaZ in receptor and effector coupling, J Neurochem, (1997), 68:2514-22.
Jain N et al., Protein kinase C delta associates with and phosphorylates Stat3 in an interleukin-6-dependent manner, J Biol Chem, (1999), 274:24392-400.
Jayanthi LD et al., Phosphorylation of the norepinephrine transporter at threonine 258 and serine 259 is linked to protein kinase C-mediated transporter internalization, J Biol Chem, (2006), 281:23326-40.
Johnson JA et al., A protein kinase C translocation inhibitor as an isozyme-selective antagonist of cardiac function, J Biol Chem, (1996), 271:24962-6.
Koponen S et al., Prevention of NMDA-induced death of cortical neurons by inhibition of protein kinase Czeta, J Neurochem, (2003), 86:442-50.
Li Y et al., SPAK kinase is a substrate and target of PKCtheta in T-cell receptor-induced AP-1 activation pathway, Embo J, (2004), 23:1112-22.

(Continued)

*Primary Examiner* — Maria Leavitt
(74) *Attorney, Agent, or Firm* — Sterne, Kessler, Goldstein & Fox P.L.L.C.

(57) ABSTRACT

The invention relates to kinase ligands and polyligands. In particular, the invention relates to ligands, homopolyligands, and heteropolyligands that modulate PKC activity. The ligands and polyligands are utilized as research tools or as therapeutics. The invention includes linkage of the ligands, homopolyligands, and heteropolyligands to a cellular localization signal, epitope tag and/or a reporter. The invention also includes polynucleotides encoding the ligands and polyligands.

14 Claims, 14 Drawing Sheets

(56) References Cited

OTHER PUBLICATIONS

Liu Y et al., Phosphorylation of the protein kinase C-theta activation loop and hydrophobic motif regulates its kinase activity, but only activation loop phosphorylation is critical to in vivo nuclear-factor-kappaB induction, Biochem J, (2002), 361:255-65.

Nika K et al., Lipid raft targeting of hematopoietic protein tyrosine phosphatase by protein kinase C theta-mediated phosphorylation, Mol Cell Biol, (2006), 26:1806-16.

Nishikawa K et al., Determination of the specific substrate sequence motifs of protein kinase C isozymes, J Biol Chem, (1997), 272:952-60.

Noland TA, Jr. et al., Identification of sites phosphorylated in bovine cardiac troponin I and troponin T by protein kinase C and comparative substrate activity of synthetic peptides containing the phosphorylation sites, J Biol Chem, (1989), 264:20778-85.

Oehrlein SA et al., Phosphorylation of GAP-43 (growth-associated protein of 43 kDa) by conventional, novel and atypical isotypes of the protein kinase C gene family: differences between oligopeptide and polypeptide phosphorylation, Biochem J, (1996), 317 ( Pt 1):219-24.

Pietromonaco SF et al., Protein kinase C-theta phosphorylation of moesin in the actin-binding sequence, J Biol Chem, (1998), 273:7594-603.

Ren J et al., p73beta is regulated by protein kinase Cdelta catalytic fragment generated in the apoptotic response to DNA damage, J Biol Chem, (2002), 277:33758-65.

Rodriguez MM et al., Characterization of the binding and phosphorylation of cardiac calsequestrin by epsilon protein kinase C, FEBS Lett, (1999), 454:240-6.

Ron D et al., C2 region-derived peptides inhibit translocation and function of beta protein kinase C in vivo, J Biol Chem, (1995), 270:24180-7.

Satoh A et al., PKC-delta and -epsilon regulate NF-kappaB activation induced by cholecystokinin and TNF-alpha in pancreatic acinar cells, Am J Physiol Gastrointest Liver Physiol, (2004), 287:G582-91.

Shimazaki Y et al., Phosphorylation of 25-kDa synaptosome-associated protein. Possible involvement in protein kinase C-mediated regulation of neurotransmitter release, J Biol Chem, (1996), 271:14548-53.

Sommerfeld MR et al., In vitro phosphorylation of insulin receptor substrate 1 by protein kinase C-zeta: functional analysis and identification of novel phosphorylation sites, Biochemistry, (2004), 43:5888-901.

Song P et al., Modulation of Kv3.1b potassium channel phosphorylation in auditory neurons by conventional and novel protein kinase C isozymes, J Biol Chem, (2006), 281:15582-91.

Strack V et al., The Protein-tyrosine-phosphatase SHP2 is phosphorylated on serine residues 576 and 591 by protein kinase C isoforms alpha, beta 1, beta 2, and eta, Biochemistry, (2002), 41:603-8.

Thuille N et al., Critical role of novel Thr-219 autophosphorylation for the cellular function of PKCtheta in T lymphocytes, Embo J, (2005), 24:3869-80.

Uddin S et al., Protein kinase C-delta (PKC-delta ) is activated by type I interferons and mediates phosphorylation of Stat1 on serine 727, J Biol Chem, (2002), 277:14408-16.

Verghese GM et al., Protein kinase C-mediated phosphorylation and calmodulin binding of recombinant myristoylated alanine-rich C kinase substrate (MARCKS) and MARCKS-related protein, J Biol Chem, (1994), 269:9361-7.

Walaas SI et al., Protein kinase C and cyclic AMP-dependent protein kinase phosphorylate phospholemman, an insulin and adrenaline-regulated membrane phosphoprotein, at specific sites in the carboxy terminal domain, Biochem J, (1994), 304 ( Pt 2):635-40.

Ward NE et al., Inhibition of protein kinase C by N-myristoylated peptide substrate analogs, Biochemistry, (1993), 32:11903-9.

Watson JA et al., Phage display identifies thioredoxin and superoxide dismutase as novel protein kinase C-interacting proteins: thioredoxin inhibits protein kinase C-mediated phosphorylation of histone, Biochem J, (1999), 343 Pt 2:301-5.

Yang L et al., Ser1928 is a common site for Cav1.2 phosphorylation by protein kinase C isoforms, J Biol Chem, (2005), 280:207-14.

Zhang GR et al., Genetic enhancement of visual learning by activation of protein kinase C pathways in small groups of rat cortical neurons, J Neurosci, (2005), 25:8468-81.

U.S. Appl. No. 12/532,912, inventors Bachinsky et al.

Ji, Y., et al., "Targeted Inhibition of $Ca^{2+}$/Calmodulin-dependant Protein Kinase II in Cardiac Longitudinal Sarcoplasmic Reticulum Results in Decreased Phospholamban Phosphorylation at Threonine 17," *J. Biol. Chem.* 278:25063-25071, The American Society for Biochemistry and Molecular Biology, Inc. (2003).

* cited by examiner

| LIGAND X | LIGAND X |
|---|---|

FIGURE 1A

| LIGAND X | LIGAND X | LIGAND X |
|---|---|---|

FIGURE 1B

| LIGAND X | LIGAND X | LIGAND X | LIGAND X | LIGAND X |
|---|---|---|---|---|

FIGURE 1C

| LIGAND X | LIGAND Y |
|---|---|

FIGURE 3A

| LIGAND X | LIGAND Y | LIGAND Z |
|---|---|---|

FIGURE 3B

| LIGAND X | LIGAND Y | LIGAND X | LIGAND Z | LIGAND A |
|---|---|---|---|---|

FIGURE 3C

| LIGAND A | LIGAND B | LIGAND C | LIGAND D |
|---|---|---|---|

FIGURE 3D

| LIGAND A | LIGAND A | LIGAND B | LIGAND C |
|---|---|---|---|

FIGURE 3E

| LIGAND X | LIGAND X | EPITOPE |
|---|---|---|

FIGURE 5A

| EPITOPE | LIGAND X | LIGAND Y |
|---|---|---|

FIGURE 5B

| LIGAND X | SPACER | LIGAND X | EPITOPE |
|---|---|---|---|

FIGURE 5C

| EPITOPE | LIGAND X | SPACER | LIGAND Y |
|---|---|---|---|

FIGURE 5D

| LIGAND X | SPACER | LIGAND Y | SPACER | LIGAND A | LIGAND B | EPITOPE |
|---|---|---|---|---|---|---|

FIGURE 5E

| EPITOPE | LIGAND X | SPACER | LIGAND Y | LIGAND A | LIGAND B |
|---|---|---|---|---|---|

FIGURE 5F

| LIGAND X | EPITOPE |
|---|---|

FIGURE 5G

| LIGAND X | LIGAND X | LOCALIZATION SIGNAL |

FIGURE 7A

| LOCALIZATION SIGNAL | LIGAND X | LIGAND Y |

FIGURE 7B

| LIGAND X | SPACER | LIGAND X | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND A | LIGAND B | LIGAND C | LIGAND D |

FIGURE 7F

| LOCALIZATION SIGNAL | LIGAND Y |

FIGURE 7G

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

FIGURE 9G

PKC LIGANDS AND POLYNUCLEOTIDES ENCODING PKC LIGANDS

CROSS-REFERENCE TO RELATED APPLICATIONS

This application claims priority to U.S. Ser. No. 60/821,958, filed 9 Aug. 2006, which is incorporated by reference.

BACKGROUND OF THE INVENTION

1. Field of the Invention

The invention relates to mammalian kinase ligands, substrates and modulators. In particular, the invention relates to polypeptides, polypeptide compositions and polynucleotides that encode polypeptides that are ligands, substrates, and/or modulators of PKC. The invention also relates to polyligands that are homopolyligands or heteropolyligands that modulate PKC activity. The invention also relates to ligands and polyligands tethered to a subcellular location.

2. Background of the Invention

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Mammalian Protein Kinase C is also known as PKC. PKC can phosphorylate serine and threonine residues in protein or peptide substrates. The enzymatic activity, activation and regulation of PKC have been studied. Many cellular substrates of PKC have been identified (See for example, Ahmed et al. 2005 FEBS J 272:903-915; Anthonsen et al. 2001 J Biol Chem 276:35344-51; Behn-Krappa et al. 1999 Curent Biology 9:7298-37; Burchfield et al. 2004 J Biol Chem 279:18623-32; Buther et al. Biochem Biophys Res Commun 2004:703-707; Cenni et al. 2002 Biochem J 363:537-45; Edlund et al. 1998 FEBS Letters 425:166-70; Eichholtz et al. 1993 J Biol Chem 268:1982-86; Ho et al. 1997 J Neurochem 68:2514-22; Jain et al. 1999 J Biol Chem 274:24392-24400; Jayanthi et al. J Biol Chem Jun. 1, 2006 manuscript M601156200; Jayanthi et al. 2006 J Biol Chem 281:23326-40; Johnson et al. 1996 J Biol Chem 271:24962-66; Koponen et al. 2003 J Neurochem 86:442-50; Li et al. 2004 EMBO J 23:1112-1122; Liu et al. 2002 Biochem J 361:255-265; Nika et al. 2006 Mol Cell Biol 26:1806-1816; Nishikawa et al. 1997 J Biol Chem 272:952-60; Noland et al. 1989 J Biol Chem 264:20778-785; Oehrlein et al. 1996 Biochem J 317:219-224; Pietromonaco et al. 1998 J Biol Chem 273:7594-603; Ren et al. 2002 J Biol Chem 277:33758-765; Rodriguez et al. 1999 FEBS Letters 454:240-46; Ron et al. 1995 J Biol Chem 270:24180-87; Satoh et al. 2004 Am J Physiol Gastrointest Liver Physiol 287:G582-G591; Shimazaki et al. 1996 J Biol Chem 271:14548-53; Sommerfeld et al. 2004 Biochemistry 43:5888-5901; Song et al. 2006 J Biol Chem 281:15582-91; Strack et al. 2002 Biochemistery 41:603-608; Thuille et al. 2005 EMBO J 24:3869-80; Uddin et al. 2002 J Biol Chem 277:14408-14416; Verghese et al. 1994 J Biol Chem 269:9361-67; Walaas et al. 1994 Biochem J 302:635-40; Ward et al. 1993 Biochemistry 32:11903-11909; Watson et al. 1999 Biochem J 343:301-305; Yang et al. 2005 J Biol Chem 280:207-214; Zhang et al. 2005 J Neurosci 25:8468-81).

There are several small molecule agents known in the art and used experimentally, such as staurosporine, K-252a, UCN-01, tamoxifen, benzolactams, ruboxistaurin that modulate PKC activity. Natural and synthetic polypeptides have been studied to examine PKC substrate specificity. While polypeptides and variants thereof have been studied as individual PKC substrates or ligands, mixed ligands linked together as polyligands that modulate PKC activity have not been demonstrated before this invention. An aspect of the invention is to provide novel, modular, inhibitors of PKC activity by modifying one or more natural substrates either by truncation or by amino acid substitution. A further aspect of the invention is the subcellular localization of a PKC inhibitor, ligand, or polyligand by linking to a subcellular localization signal.

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

SUMMARY OF THE INVENTION

The invention relates to polypeptide ligands and polyligands for PKC. Various embodiments of the PKC ligands and polyligands are represented in SEQ ID NOS:1-123. More specifically, the invention relates to ligands, homopolyligands, and heteropolyligands that comprise any one or more of SEQ ID NOS:43-123. Additionally, the invention relates to ligands and polyligands comprising one or more subsequences of SEQ ID NOS:13-42 or any portion thereof Furthermore, the invention relates to polyligands with at least about 80%, 85%, 90%, 95%, 96%, 97%, 98% and 99% sequence identity to a polyligand comprising one or more of SEQ ID NOS:43-123 or any portion thereof Furthermore, the invention relates to polyligands with at least about 80%, 85%, 90%, 95%, 96%, 97%, 98% and 99% sequence identity to a polyligand comprising one or more subsequences of SEQ ID NOS:13-42.

Polyligands, which can be homopolyligands or heteropolyligands, are chimeric ligands composed of two or more monomeric polypeptide ligands. An example of a monomeric ligand is the polypeptide represented by SEQ ID NO:57, wherein Xaa is any amino acid. SEQ ID NO:57 is a selected subsequence of wild-type full length SEQ ID NO:13, wherein the amino acid corresponding to Xaa in the wild-type sequence is a serine or threonine phosphorylatable by PKC. An example of a homopolyligand is a polypeptide comprising a dimer or multimer of SEQ ID NO:57, wherein Xaa is any amino acid. An example of a heteropolyligand is a polypeptide comprising SEQ ID NO:43 and one or more of SEQ ID NOS:44-123, wherein Xaa is any amino acid. There are numerous ways to combine SEQ ID NOS:43-123 into homopolymeric or heteropolymeric ligands. Furthermore, there are numerous ways to combine additional subsequences of SEQ ID NOS:13-42 with each other and with SEQ ID NOS:43-123 to make polymeric ligands.

The polyligands of the invention optionally comprise spacer amino acids between monomers. SEQ ID NO:1 is an embodiment of a polyligand of the structure A-S1-B-S2-C-S1-D, wherein A is SEQ ID NO:43, B is SEQ ID NO:44, C is SEQ ID NO:45, and D is SEQ ID NO:46, wherein Xaa is alanine, and wherein S1 and S2 are four amino acid spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

A monomeric ligand is a polypeptide where at least a portion of the polypeptide is capable of being recognized by PKC. The portion of the polypeptide capable of recognition is termed the recognition motif In the present invention, recognition motifs can be natural or synthetic. Examples of recognition motifs are well known in the art and include, but are not limited to, naturally occurring PKC substrates and pseudosubstrate motifs.

A polymeric ligand comprises two or more monomeric ligands.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where each of the monomeric ligands does not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclease activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

BRIEF DESCRIPTION OF THE DRAWINGS

FIGS. 1A-1C show examples of homopolymeric ligands without spacers.

FIGS. 3A-3E show examples of heteropolymeric ligands without spacers.

FIGS. 5A-5G show examples of ligands and polymeric ligands linked to an optional epitope tag.

FIGS. 7A-7G show examples of ligands and polymeric ligands linked to an optional localization signal.

FIGS. 8A-8G show examples of ligands and polymeric ligands linked to an optional localization signal and an optional epitope tag.

FIGS. 9A-9G show examples of gene constructs where ligands and polyligands are linked to an optional localization signal, an optional epitope tag, and an optional reporter.

DETAILED DESCRIPTION OF THE INVENTION

Figure 2A:
FIGS. 2A-2C show examples of homopolymeric ligands with spacers.
Figure 2B:
Figure 2C:

This application has subject matter related to application Ser. No. 10/724,532 (now U.S. Pat. No. 7,071,295), Ser. No. 10/682,764 (US2004/0185556, PCT/US2004/013517, WO2005/040336), Ser. No. 11/233,246, and US20040572011P (WO2005116231). Each of these patents and applications is hereby incorporated by reference.

The present invention relates to ligands and polyligands that are PKC modulators. Various embodiments of ligands and polyligands are represented in SEQ ID NOS:1-123. Polyligands are chimeric ligands comprising two or more monomeric polypeptide ligands. An example of a monomeric ligand is the polypeptide represented by SEQ ID NO:58, wherein Xaa is any amino acid. SEQ ID NO:58 is a selected subsequence of wild-type full length SEQ ID NO:14, wherein the amino acid corresponding to Xaa in the wild-type sequence is a serine or threonine phosphorylatable by PKC. Another example of a monomeric ligand is the polypeptide represented by SEQ ID NO:123. Each of SEQ ID NOS:43-123 represents an individual polypeptide ligand in monomeric form, wherein Xaa is any amino acid. SEQ ID NOS:43-105 are selected examples of subsequences of SEQ ID NOS:13-42, however, other subsequences of SEQ ID NOS:13-42 may also be utilized as monomeric ligands. Monomeric ligand subsequences of SEQ ID NOS:13-42 may be wild-type subsequences. Additionally, monomeric ligand subsequences of SEQ ID NOS:13-42 may have the PKC phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:43-123. Furthermore, monomeric ligands and polyligands may have at least about 80%, 85%, 90%, 95%, 96%, 97%, 98% and 99% sequence identity to a subsequence of SEQ ID NOS:13-42.

An example of a homopolyligand is a polypeptide comprising a dimer or multimer of SEQ ID NO:43, wherein Xaa is any amino acid. An example of a heteropolyligand is a polypeptide comprising SEQ ID NO:43 and one or more of SEQ ID NOS:44-123, wherein Xaa is any amino acid. There are numerous ways to combine SEQ ID NOS:43-123 into homopolymeric or heteropolymeric ligands. Furthermore, there are numerous ways to combine additional subsequences of SEQ ID NOS:13-42 with each other and with SEQ ID NOS:53-123 to make polymeric ligands.

Polyligands may comprise any two or more of SEQ ID NOS:43-123, wherein Xaa is any amino acid. A dimer or multimer of SEQ ID NO:91 is an example of a homopolyligand. An example of a heteropolyligand is a polypeptide comprising SEQ ID NO:123 and one or more of SEQ ID NOS:43-122. There are numerous ways to combine SEQ ID NOS:43-123 into homopolymeric or heteropolymeric ligands. SEQ ID NOS:43-105 are selected examples of subsequences of SEQ ID NOS:13-42, however, additional subsequences, wild-type or mutated, may be utilized to form polyligands. The instant invention is directed to all possible combinations of homopolyligands and heteropolyligands without limitation.

SEQ ID NOS:13-42 show proteins that contain at least one serine or threonine residue phosphorylatable by PKC, the positions of which are represented by Xaa. SEQ ID NOS:43-105 are subsequences of SEQ ID NOS:13-42 where, again, the locations of the PKC phosphorylatable residues are represented by Xaa. In nature, Xaa is, generally speaking, serine or threonine. In one embodiment of the instant invention, Xaa can be any amino acid. Ligands where Xaa is serine or threonine can be used as part of a polyligand, however in one embodiment, at least one phosphorylatable serine or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the PKC phosphorylatable serine(s) or threonine(s) are replaced by alanine. The ligands and polyligands of the invention are designed to modulate the endogenous effects of one or more isoforms of PKC.

In general, ligand monomers based on natural PKC substrates are built by isolating a putative PKC phosphorylation recognition motif in a PKC substrate. Sometimes it is desirable to modify the phosphorylatable residue to an amino acid other than serine or threonine. Additional monomers include the PKC recognition motif as well as amino acids adjacent and contiguous on either side of the PKC recognition motif. Monomeric ligands may therefore be any length provided the monomer includes the PKC recognition motif For example, the monomer may comprise an PKC recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of PKC comprising at least one copy of a peptide selected from the group consisting of: a) a peptide at least 80%, 85%, 90%, 95%, 96%, 97%, 98% or 99% identical to a peptide comprising amino acid residues corresponding to amino acid residues 444-451 of SEQ ID NO:13, wherein the amino acid residue corresponding to amino acid residue 449 of SEQ ID NO:13 has been mutated to an amino acid residue other than serine or threonine; b) a peptide at least 80%, 85%, 90%, 95%, 96%, 97%, 98% or 99% identical to a peptide comprising amino acid residues corresponding to amino acid residues 440-453 of SEQ ID NO:13, wherein the amino acid residue corresponding to amino acid residue 449 of SEQ ID NO:13 has been mutated to an amino acid residue other than serine or threonine; c) a peptide at least 80%, 85%, 90%, 95%, 96%, 97%, 98% or 99% identical to a peptide comprising amino acid residues corresponding to amino acid residues 435-455 of SEQ ID NO:13, wherein the amino acid residue corresponding to amino acid residue 449 of SEQ ID NO:13 has been mutated to an amino acid residue other than serine or threonine; and d) a peptide at least 80%, 85%, 90%, 95%, 96%, 97%, 98% or 99% identical to a peptide comprising amino acid residues corresponding to amino acid residues 430-458 of SEQ ID NO:13, wherein the amino acid residue corresponding to amino acid residue 449 of SEQ ID NO:13 has been mutated to an amino acid residue other than serine or threonine.

As used herein, the terms "correspond(s) to" and "corresponding to," as they relate to sequence alignment, are intended to mean enumerated positions within a reference protein, e.g., kibra (SEQ ID NO:26), and those positions that align with the positions on the reference protein. Thus, when the amino acid sequence of a subject peptide is aligned with the amino acid sequence of a reference peptide, e.g., SEQ ID NO:26, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for PKC, such as substrates identified by SEQ ID NOS: 13-105. Furthermore, if the substrate has more than one recognition motif, then more than one monomer may be identified therein.

Further embodiments of the invention include monomers based on PKC inhibitors and regulators, such as those identified by SEQ ID NOS:106-123 and subsequences thereof.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting PKC in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring PKC recognition motif that has been modified by addition, deletion, or substitution of one or more amino acids in the primary structure (amino acid sequence) of the motif For example, a modified PKC recognition motif may be a motif where the phosphorylatable amino acid has been modified to a non-phosphorylatable amino acid. The terms "protein" and "polypeptide" are used interchangeably herein. The reference inhibitor is not necessarily a wild-type protein or a portion thereof Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

Figure 4A:
FIGS. 4A-4F show examples of heteropolymeric ligands with spacers.
Figure 4B:
Figure 4C:
Figure 4D:
Figure 4E:

The polyligands of the invention optionally comprise spacer amino acids between monomers. The length and composition of the spacer may vary. An example of a spacer is glycine, alanine, polyglycine, or polyalanine. Specific examples of spacers used between monomers in SEQ ID NO:9 are the six amino acids AAGGAA, the six amino acids GGAAGG, and the seven amino acids PGAGAGA. In the instance of SEQ ID NO:9, the proline-containing spacer is intended to break an alpha helical secondary structure. Spacer amino acids may be any amino acid and are not limited to alanine, glycine and proline. SEQ ID NO:9, depicted generically in FIG. 4D, represents a specific example of a polyligand of the structure X-S5-Y-S6-Z-S7-A, wherein X is SEQ ID NO:50, Y is SEQ ID NO:5 1, Z is SEQ ID NO:52, and A is SEQ ID NO:53, wherein Xaa is alanine, and wherein S5, S6 and S7 are spacers. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G). Non-limiting examples of epitope tags are FLAG™ (Kodak; Rochester, N.Y.), HA (hemagluttinin), c-Myc and His6. Additional examples of epitope tags are given in Jarvik & Telmer 1998 Annual Reviw of Genetics 32:601-18. Non-limiting examples of reporters are alkaline phosphatase, galactosidase, peroxidase, luciferase and green fluorescent protein (GFP). Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Pepetides can also be synthesized utilizing non-automated peptide sythesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. For example, the ligands generically depicted in FIGS. 1A-1C, FIGS. 2A-2C, FIGS. 3A-3C, and FIGS. 4A-4C represent embodiments of conventional polypeptide therapeutics. However, ligands linked to localization signals have utility as subcellular tools or therapeutics. For example, ligands depicted generically in FIGS. 7A-7G represent ligands with utility as subcellular tools or therapeutics. PKC ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10A:
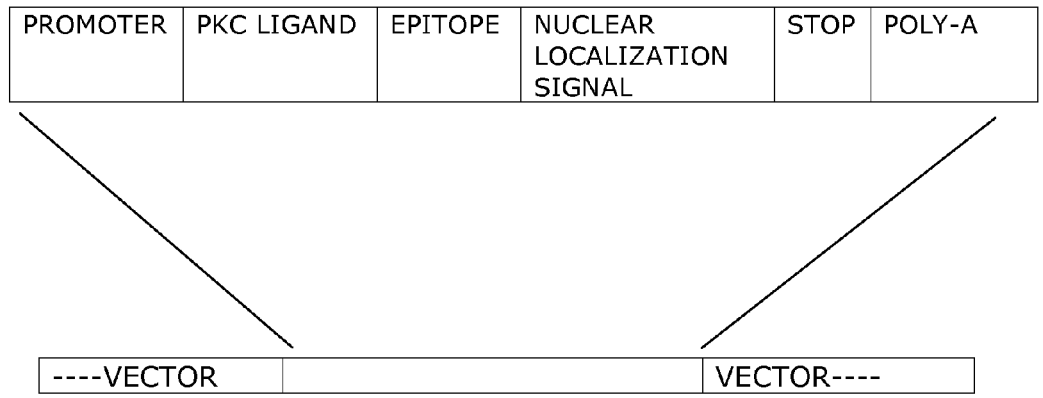
FIGS. 10A-10D show examples of vectors containing ligand gene constructs.
Figure 10B:
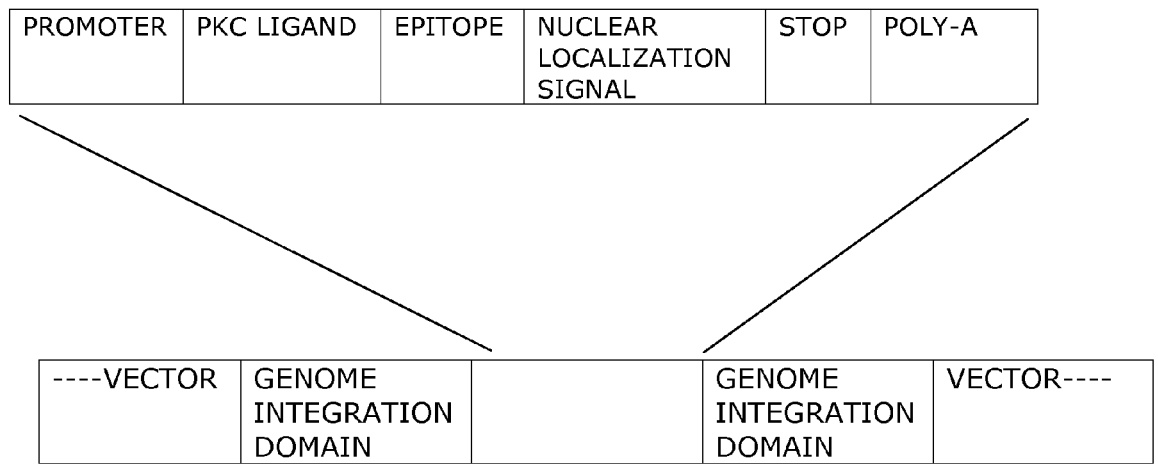
Figure 10C:
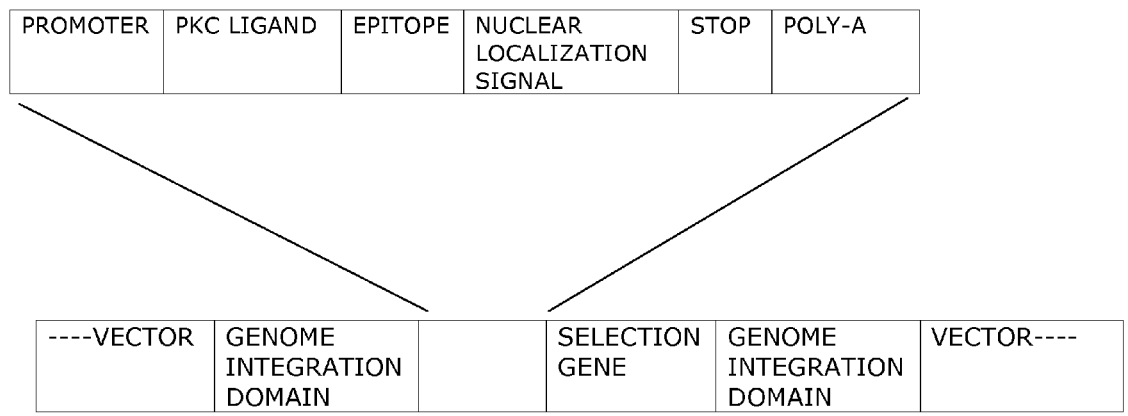

FIG. 10A shows a vector containing a PKC ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
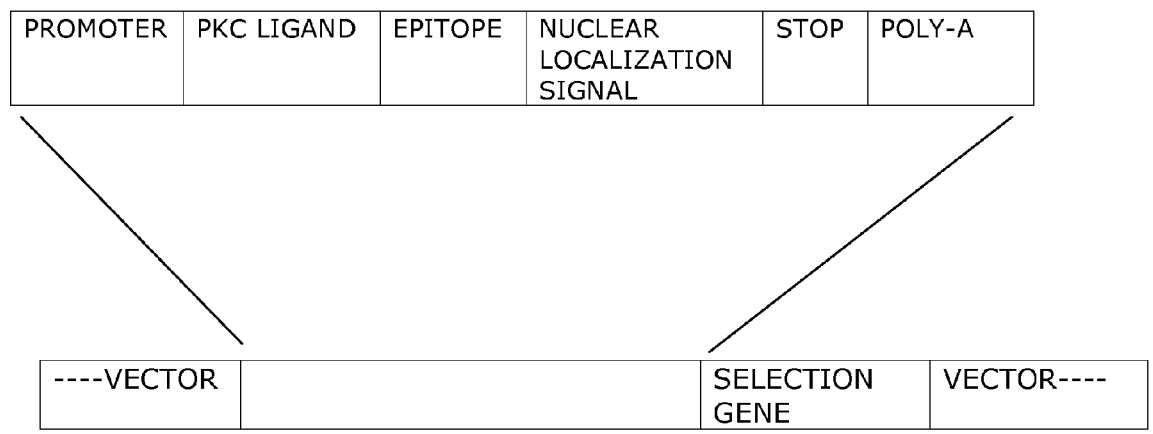

FIG. 10D shows a vector containing a PKC ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclese activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealled. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. For example, a tetracycline-inducible promotor is activated to express a downstream coding sequence when the cell containing the promotor and other necessary cellular factors is treated with tetracycline. When tetracycline is removed, gene expression is subsequently reduced. Other inducible promotors are activated by other drugs or factors. RheoSwitchR is an inducible promotor system available from RheoGene. Temperature sensitive promotors can also be used to increase or decrease gene expression. An embodiment of the invention comprises a ligand or polyligand gene construct whose expression is controlled by an inducible promotor. In one embodiment, the inducible promotor is tetracycline inducible.

Figure 11:
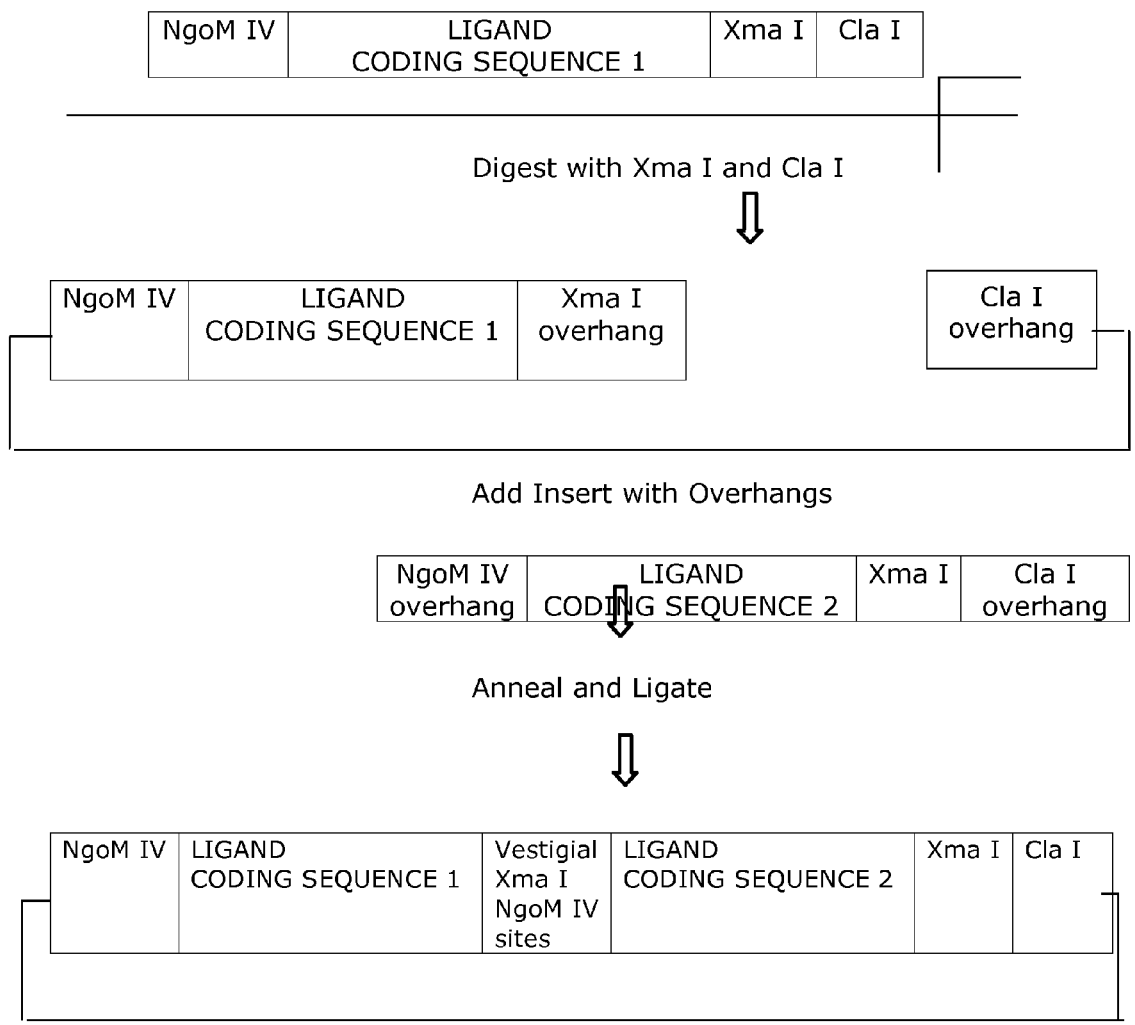
FIG. 11 shows an example of a sequential cloning process useful for combinatorial synthesis of polyligands.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5° Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endouclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate PKC activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

Assays. Ligands of the invention are assayed for kinase modulating activity using one or more of the following methods.

Method 1. A biochemical assay is performed employing commercially-obtained kinase, commercially-obtained substrate, commercially-obtained kinase inhibitor (control), and semi-purified inhibitor ligand of the invention (decoy ligand). Decoy ligands are linked to an epitope tag at one end of the polypeptide for purification and/or immobilzation, for example, on a microtiter plate. The tagged decoy ligand is made using an in vitro transcription/translation system such as a reticulocyte lysate system well known in the art. A vector polynucleotide comprising a promotor, such as T7 and/or T3 and/or SP6 promotor, a decoy ligand coding sequence, and an epitope tag coding sequence is employed to synthesize the tagged decoy ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations are performed as described in: Using Antibodies: A Laboratory Manual (Harlow and Lane Cold Spring Harbor Laboratory Press, 1999).

Specifically, tagged decoy ligand synthesized using an in vitro transcription/translation system is semi-purified and added to a microtiter plate containing kinase enzyme and substrate immobilized by an anti-substrate specific antibody. Microtiter plates are rinsed to substantially remove non-immobilized components. Kinase activity is a direct measure of the phosphorylation of substrate by kinase employing a phospho-substrate specific secondary antibody conjugated to horseradish peroxidase (HRP) followed by the addition of 3,3',5,5'-tetramethylbenzidine (TMB) substrate solution. The catalysis of TMB by HRP results in a blue color that changes to yellow upon addition of phosphoric or sulfuric acid with a maximum absorbance at 450 nm. The Control experiments include absence of kinase enzyme, and/or absence of decoy ligand, and/or presence/absence of known kinase inhibitors. A known kinase inhibitor useful in the assay is staurosporine.

Method 2. A similar assay is performed employing the same reagents as above but the substrate is biotinylated and immobilized by binding to a streptavidin-coated plate.

Method 3. A biochemical assay is performed employing commercially-obtained kinase, commercially-obtained substrate, commercially-obtained kinase inhibitor (control), and semi-purified inhibitor ligand of the invention (decoy ligand) in a microtiter plate. A luminescent-based detection system, such as Promega's Kinase-Glo, is then added to inversely measure kinase activity.

Specifically, tagged decoy ligand synthesized using an in vitro transcription/translation system is semi-purified and added to a microtiter plate containing kinase enzyme and substrate. After the kinase assay is performed, luciferase and luciferin are added to the reaction. Luciferase utilizes any remaining ATP not used by the kinase to catalyze luciferin. The luciferase reaction results in the production of light which is inversely related to kinase activity. Control experiments include absence of kinase enzyme, and/or absence of decoy ligand, and/or presence/absence of known kinase inhibitors. A known kinase inhibitor useful in the assay is staurosporine.

Method 4. A similar cell-based assay is performed employing same reagents as above, but synthesizing the decoy ligand in a mammalian cell system instead of an in vitro transcription/translation system. Decoy ligands are linked to an epitope tag at one end of the polypeptide for immobilzation and/or for purification and/or for identification in a western blot. Optionally, tagged decoy ligands are also linked to a cellular localization signal for phenotypic comparison of pan-cellular and localized kinase modulation. A vector polynucleotide comprising a constitutive promotor, such as the CMV promotor, a decoy ligand coding sequence, an epitope tag coding sequence, and optionally a localization signal coding sequence is employed to express the decoy ligand in cells. Transfection and expression protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Western Blots and immunoreagent-containing methods are performed as described in: Using Antibodies: A Laboratory Manual (Harlow and Lane Cold Spring Harbor Laboratory Press, 1999).

EXAMPLE 1

A polypeptide comprising a heteropolyligand, an endoplasmic reticulum cellular localization signal, and a His6 epitope is synthesized. Examples of such polypeptides are generically represented by FIGS. 8A, 8B, 8D, 8E and 8F. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

EXAMPLE 2

A transgene is constructed using a human cytomegalovirus (CMV) promoter to direct expression of a fusion protein comprising SEQ ID NO:107, SEQ ID NO:108, SEQ ID NO:110 (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein (GFP) by confocal microscopy.

EXAMPLE 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a PKC ligand, a FLAG™ epitope, and a nuclear localization signal. The PKC ligand is a monomeric ligand, homopolymeric ligand or heteropolymeric ligand as described herein. Nucleotide sequences encoding a FLAG™ epitope are placed downstream of nucleotide sequences encoding the PKC ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

EXAMPLE 4

Modulation of PKC cellular function by subcellularly localized PKC polyligand is illustrated. A transgene construct containing nucleic acids that encode a polyligand fusion protein, epitope, and nuclear localization signal is made. The expression unit contains nucleotides that encode SEQ ID NO:1 (POLYLIGAND), a c-Myc epitope (EPITOPE), and a nuclear localization signal (LOCALIZATION SIGNAL). This expression unit is subsequently subcloned into a vector between a CMV promoter and an SV40 polyadenylation signal (Generically depicted in FIG. 10A and FIG. 12). The completed transgene-containing expression vector is then used to transfect cells. Inhibition of PKC activity is demonstrated by measuring phosphorylation of endogenous substrates against controls.

EXAMPLE 5

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode a tetramer of SEQ ID NO:75, a hemagluttinin epitope, and a mitochondrial localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 5 harbor the transgene in their genomes.

Test 2: Tissue homogenates are prepared for Western blot analysis. This experiment demonstrates the transgene is expressed in tissues of transgenic mice because hemagluttinin epitope is detected in transgenic homogenates but not in non-transgenic homogenates.

Test 3: Function is assessed by phenotypic observation or analysis against controls.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate PKC activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

SEQ ID NOS:1-12 are example polyligands and polynucleotides encoding them.

Figure 12:
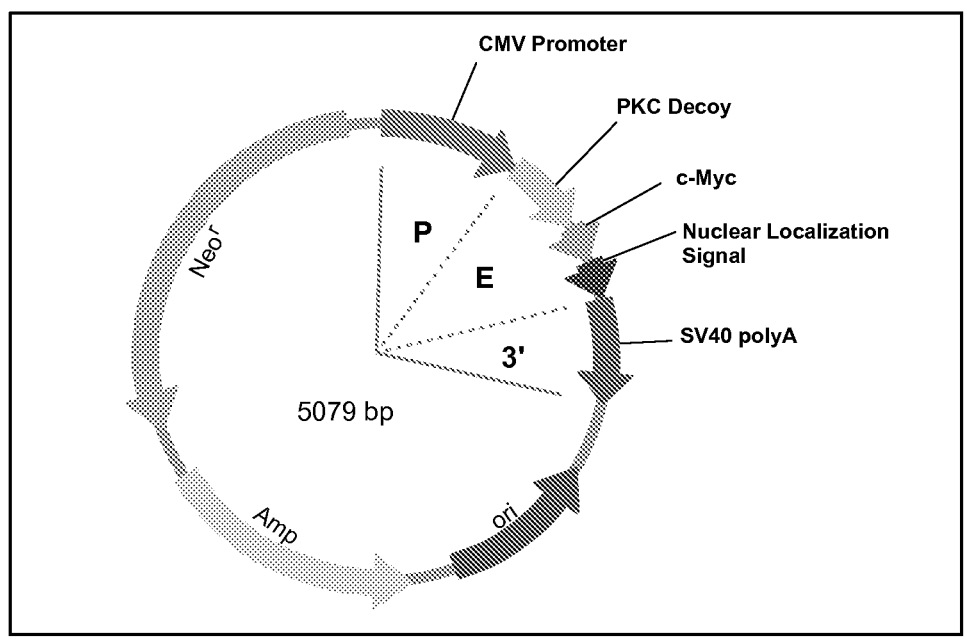
FIG. 12 shows a diagram of a vector for cell transformation.

Specifically, the PKC polyligand of SEQ ID NO:1 is encoded by SEQ ID NO:2, SEQ ID NO:3 and by SEQ ID NO:4, wherein the the codons of SEQ ID NO:3 and SEQ ID NO:4 have been optimized for vector insertion. SEQ ID NO:4 includes flanking restriction sites. A vector map of a vector containing SEQ ID NO:3 is shown in FIG. 12 (labeled PKC decoy). SEQ ID NO:1 is an embodiment of a polyligand of the structure A-S1-B-S2-C-S1-D, wherein A is SEQ ID NO:43, B is SEQ ID NO:44, C is SEQ ID NO:45, and D is SEQ ID NO:46, wherein Xaa is alanine, and wherein S1 is a spacer of the amino acid sequence GAGA and S2 is a spacer of amino acid sequence AGAG. A polyligand of structure A-S1-B-S2-C-S1-D is also called herein a heteropolyligand, shown generically in FIG. 4D.

Figure 4F:
Figure 6A:
FIGS. 6A-6G show examples of ligands and polymeric ligands linked to an optional reporter.
Figure 6B:
Figure 6C:
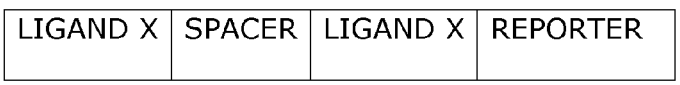
Figure 6D:
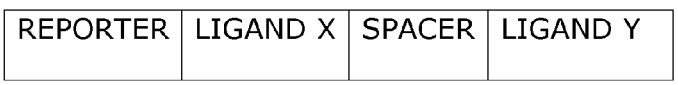
Figure 6E:
Figure 6F:
Figure 6G:

SEQ ID NO:5 is an embodiment of a polyligand of the structure X-S4-Y-S4-Z-S4-Y, wherein X is SEQ ID NO:47, Y is SEQ ID NO:48, and Z is SEQ ID NO:49, wherein Xaa is alanine, and wherein S4 is a spacer of amino acid sequence AAGPGAA. The PKC polyligand of SEQ ID NO:5 is encoded by SEQ ID NO:6, SEQ ID NO:7 and by SEQ ID NO:8, wherein the the codons of SEQ ID NOS:7 and 8 have been optimized for vector insertion. SEQ ID NO:8 includes flanking restriction sites. A polyligand of structure X-S4-Y-S4-Z-S4-Y is also called herein a heteropolyligand, shown generically in FIG. 4F.

SEQ ID NO:9 is an embodiment of a polyligand of the structure X-S5-Y-S6-Z-S7-A, wherein X is SEQ ID NO:50, Y is SEQ ID NO:51, Z is SEQ ID NO:52, and A is SEQ ID NO:53, wherein Xaa is alanine, and wherein S5 is a six amino acid spacer with the sequence AAGGAA, S6 is a six amino acid spacer with the sequence GGAAGG, and S7 is a seven amino acid spacer with sequence PGAGAGA. The PKC polyligand of SEQ ID NO:9 is encoded by SEQ ID NO:10, SEQ ID NO:11, and by SEQ ID NO:12, wherein the codons of SEQ ID NOS:11 and 12 have been optimized for vector insertion. SEQ ID NO:12 includes flanking restriction sites. A polyligand of structure X-S5-Y-S6-Z-S7-A is also called herein a heteropolyligand.

SEQ ID NOS:13-42 are full length PKC protein substrates. These sequences have the following public database accession numbers: CAA50435, NP002825, NP_036988, AAB28649, NP034195, AAA41244, CAH72875, P29966, P42225, NP005418, AAA75480, CAA73665, AAX37356, NP056053, CAA41264, NP056053, NP542155, AAC72238, NP002435, CAA41402, AAB27731, NP113836, AAH26342, AAH66915, NP003072, NP_006248, NP_001020429, NP_006167, AAU20354, and NP_000499. Each of the sequences represented by these accession numbers is incorporated by reference herein. In SEQ ID NOS:13-42, the positions of the amino acid(s) phosphorylatable by PKC are represented by Xaa. In wild-type proteins, Xaa is serine or threonine. In the ligands of the invention, Xaa is any amino acid.

SEQ ID NOS:43-105 are peptide sequences including subsequences of SEQ ID NOS:13-42, which represent examples of peptide ligand sequences where the location of the PKC phosphorylatable serine or threonine in the natural polypeptide is designated as Xaa.

SEQ ID NOS:106-123 are inhibitors of PKC, wherein SEQ ID NOS:106-123 are non-endogenous, artificial peptides.

SEQ ID NOS:43-123 represent examples of monomeric peptide ligand sequences.

Amino acid sequences containing Xaa encompass peptides where Xaa is any amino acid.

What is claimed is:

1. An isolated polynucleotide comprising a nucleotide sequence encoding a polypeptide polyligand comprising monomeric ligands, said polypeptide polyligand having at least 95% sequence identity to the polypeptide of SEQ ID NO: 5, wherein said polypeptide polyligand inhibits protein kinase C activity.

2. A vector comprising the isolated polynucleotide of claim 1.

3. The isolated polynucleotide of claim 1, wherein the polynucleotide is flanked at one terminus by a sequence cleavable by a first restriction endonuclease, and wherein the polynucleotide is flanked at the other terminus by a sequence cleavable by a second restriction endonuclease, and wherein the first and second restriction endonucleases generate non-compatible cohesive ends.

4. The polynucleotide of claim 3, wherein the first restriction endonuclease and the second endonuclease are selected from the group consisting of NgoM IV, Xma I and Cla I.

5. A host cell comprising the vector of claim 2.

6. A method for inhibiting PKC in a cell comprising introducing the vector of claim 2 into a host cell and maintaining the host cell under conditions suitable to produce at least one copy of the polypeptide.

7. The method of claim 6, wherein said method is performed in vitro.

8. The isolated polynucleotide of claim 1, wherein said polypeptide is at least 96% identical to the polypeptide of SEQ ID NO: 5.

9. The isolated polynucleotide of claim 1, wherein said polypeptide is at least 97% identical to the polypeptide of SEQ ID NO: 5.

10. The isolated polynucleotide of claim 1, wherein said polypeptide is at least 98% identical to the polypeptide of SEQ ID NO: 5.

11. The isolated polynucleotide of claim 1, wherein said polypeptide is at least 99% identical to the polypeptide of SEQ ID NO: 5.

12. The isolated polynucleotide of claim 1, wherein said polynucleotide comprises SEQ ID NO: 6.

13. The isolated polynucleotide of claim 1, wherein said polynucleotide comprises SEQ ID NO: 7.

14. The isolated polynucleotide of claim 1, wherein said polynucleotide comprises SEQ ID NO: 8.

* * * * *

SEQUENCE LISTING

<160> NUMBER OF SEQ ID NOS: 123

<210> SEQ ID NO 1
<211> LENGTH: 75
<212> TYPE: PRT
<213> ORGANISM: artificial sequence
<220> FEATURE:
<223> OTHER INFORMATION: Synthetic

<400> SEQUENCE: 1

Gln Lys Arg Pro Ala Gln Arg Ser Lys Tyr Leu Gly Ala Gly Ala Ala
1               5                   10                  15

Ala Lys Ile Gln Ala Ala Phe Arg Gly His Met Ala Arg Lys Lys Ala
            20                  25                  30

Gly Ala Gly Arg Arg Gly Arg Ala Gly Arg Gly Arg Arg Gly Ile Phe
        35                  40                  45

Arg His Glu Gly Thr His Ala Thr Lys Arg Gly Ala Gly Ala Pro Leu
    50                  55                  60

Ser Arg Thr Leu Ala Gln Arg Ser Lys Tyr Leu
65                  70                  75

<210> SEQ ID NO 2
<211> LENGTH: 225
<212> TYPE: DNA
<213> ORGANISM: artificial sequence
<220> FEATURE:
<223> OTHER INFORMATION: Synthetic

<400> SEQUENCE: 2
cagaagaggc ccgcccagag gagcaagtac ctgggcgccg cgccgccgc caagatccag      60 gccgccttca ggggccacat ggccaggaag aaggccggcg ccggcaggag gggcagggcc    120
ggcaggggca ggaggggcat cttcaggcac gagggcaccc acgccaccaa gaggggcgcc    180 ggcgccccc tgagcaggac cctggcccag aggagcaagt acctg                      225

<210> SEQ ID NO 3
<211> LENGTH: 225
<212> TYPE: DNA
<213> ORGANISM: artificial sequence
<220> FEATURE:
<223> OTHER INFORMATION: Synthetic

<400> SEQUENCE: 3
cagaagaggc ccgcccagag gagcaagtac ctgggagccg gagccgccgc caagatccag      60
gccgccttca ggggccacat ggctaggaag aaggccggag ctggcaggag gggcagggct    120
ggcaggggca ggaggggcat cttcaggcat gagggcaccc acgccaccaa gaggggcgct    180 ggagccccc tgagcaggac actggcccag aggagcaagt acctg                      225

<210> SEQ ID NO 4
<211> LENGTH: 255
<212> TYPE: DNA
<213> ORGANISM: artificial sequence
<220> FEATURE:
<223> OTHER INFORMATION: Synthetic

<400> SEQUENCE: 4
gccggcgctc agaagaggcc cgcccagagg agcaagtacc tgggagccgg agccgccgcc      60
aagatccagg ccgccttcag gggccacatg gctaggaaga aggccggagc tggcaggagg    120
ggcagggctg gcaggggcag gaggggcatc ttcaggcatg agggcaccca cgccaccaag    180
aggggcgctg agccccccct gagcaggaca ctggcccaga ggagcaagta cctgcccggg    240
ggaggcggaa tcgat                                                      255

<210> SEQ ID NO 5
<211> LENGTH: 157
<212> TYPE: PRT
<213> ORGANISM: artificial sequence
<220> FEATURE:
<223> OTHER INFORMATION: Synthetic

<400> SEQUENCE: 5

Gly Asn Glu Ile Asp Thr Gln Asn Arg Gln Ile Asp Arg Ile Met Glu
1               5                   10                  15

Lys Ala Asp Ala Asn Lys Thr Arg Ile Asp Glu Ala Asn Gln Arg Ala
                20                  25                  30

Thr Lys Met Leu Gly Ala Ala Gly Pro Gly Ala Ala Ala Leu Ser Asn
            35                  40                  45

Met Met His Phe Gly Gly Tyr Ile Gln Lys Gln Ala Gln Ala Glu Arg
        50                  55                  60

Lys Ser Gly Lys Arg Gln Ala Glu Arg Glu Lys Ala Ala Gly Pro Gly
 65                  70                  75                  80

Ala Ala Ile Thr Glu Ile Ala Asp Leu Thr Gln Lys Ile Tyr Asp Leu
                 85                  90                  95

Arg Gly Lys Phe Lys Arg Pro Ala Leu Arg Arg Val Arg Ile Ser Ala
                100                 105                 110

Asp Ala Met Met Gln Ala Leu Ala Ala Gly Pro Gly Ala Ala Ala Leu
            115                 120                 125

Ser Asn Met Met His Phe Gly Gly Tyr Ile Gln Lys Gln Ala Gln Ala
        130                 135                 140

Glu Arg Lys Ser Gly Lys Arg Gln Ala Glu Arg Glu Lys
145                 150                 155

<210> SEQ ID NO 6
<211> LENGTH: 471
<212> TYPE: DNA
<213> ORGANISM: artificial sequence
<220> FEATURE:
<223> OTHER INFORMATION: Synthetic

<400> SEQUENCE: 6
ggcaacgaga tcgacaccca gaacaggcag atcgacagga tcatggagaa ggccgacgcc      60
aacaagacca ggatcgacga ggccaaccag agggccacca agatgctggg cgccgccggc     120
cccggcgccg ccgccctgag caacatgatg cacttcggcg gctacatcca gaagcaggcc     180
caggccgaga ggaagagcgg caagaggcag gccgagaggg agaaggccgc cggccccggc     240
gccgccatca ccgagatcgc cgacctgacc cagaagatct acgacctgag ggcaagttc      300 aagaggcccg ccctgaggag ggtgaggatc agcgccgacg ccatgatgca ggccctggcc     360
gccggccccg cgccgccgc cctgagcaac atgatgcact cggcggcta catccagaag       420 caggcccagg ccgagaggaa gagcggcaag aggcaggccg agagggagaa g              471

<210> SEQ ID NO 7
<211> LENGTH: 471
<212> TYPE: DNA
<213> ORGANISM: artificial sequence
<220> FEATURE:
<223> OTHER INFORMATION: Synthetic

<400> SEQUENCE: 7
ggcaacgaga tcgacaccca gaacaggcag atcgacagga tcatggagaa ggccgacgcc      60
aacaagacca ggatcgacga ggccaaccag agggccacca agatgctcgg agccgctggc     120
cccggagccg ccgccctgag caacatgatg cacttcggcg gctacatcca gaagcaggcc     180
caggccgaga ggaagagcgg caagaggcag gccgagaggg agaaggccgc tggccccggc     240
gctgccatca ccgagatcgc cgacctgacc cagaaaatct acgacctgag ggcaagttc      300 aagaggcccg ccctgaggag ggtgaggatc agcgccgacg ccatgatgca ggccctggcc     360
gccggacccg agccgccgc cctgagcaac atgatgcact cggcggcta catccagaag       420 caggcccagg ccgagaggaa gagcggcaag aggcaggccg agagggagaa g              471

<210> SEQ ID NO 8
<211> LENGTH: 501
<212> TYPE: DNA
<213> ORGANISM: artificial sequence
<220> FEATURE:

<223> OTHER INFORMATION: Synthetic

<400> SEQUENCE: 8

```
gccggcgctg gcaacgagat cgacacccag aacaggcaga tcgacaggat catggagaag    60
gccgacgcca acaagaccag gatcgacgag gccaaccaga gggccaccaa gatgctcgga   120
gccgctggcc ccggagccgc cgccctgagc aacatgatgc acttcggcgg ctacatccag   180
aagcaggccc aggccgagag gaagagcggc aagaggcagg ccgagaggga gaaggccgct   240
ggccccggcg ctgccatcac cgagatcgcc gacctgaccc agaaaatcta cgacctgagg   300
ggcaagttca gaggcccgc cctgaggagg gtgaggatca cgccgacgc catgatgcag    360
gccctggccg ccggacccgg agccgccgcc ctgagcaaca tgatgcactt cggcggctac   420
atccagaagc aggcccaggc cgagaggaag agcggcaaga ggcaggccga gagggagaag   480
cccgggggag gcggaatcga t                                             501
```

<210> SEQ ID NO 9
<211> LENGTH: 108
<212> TYPE: PRT
<213> ORGANISM: artificial sequence
<220> FEATURE:
<223> OTHER INFORMATION: Synthetic

<400> SEQUENCE: 9

```
Gly Gly Arg Leu Pro Gly Tyr Arg His Ala Ala Phe Val Pro Thr His
1               5                   10                  15
Ser Tyr Pro Glu Ala Ala Gly Gly Ala Ala Asn Leu His Thr Asp Asp
            20                  25                  30
Gly Tyr Met Pro Met Ala Pro Gly Val Ala Pro Val Pro Gly Gly Ala
        35                  40                  45
Ala Gly Gly Gly Val Glu Asp Lys Glu Met Met Lys Lys Tyr Gly Lys
    50                  55                  60
Ala Phe Arg Lys Leu Leu Ser Leu Cys Leu Gln Pro Gly Ala Gly Ala
65                  70                  75                  80
Gly Ala Asn Asp Met Ile His Ala Glu Asn Met Arg Leu Gly Arg Asp
                85                  90                  95
Lys Tyr Lys Ala Leu Arg Gln Ile Arg Gln Gly Asn
            100                 105
```

<210> SEQ ID NO 10
<211> LENGTH: 324
<212> TYPE: DNA
<213> ORGANISM: artificial sequence
<220> FEATURE:
<223> OTHER INFORMATION: Synthetic

<400> SEQUENCE: 10

```
ggcggcaggc tgcccggcta caggcacgcc gccttcgtgc ccacccacag ctaccccgag    60
gccgccggcg gcgccgccaa cctgcacacc gacgacggct acatgcccat ggccccccggc   120
gtggccccg tgcccggcgg cgccgccggc ggcggcgtgg aggacaagga gatgatgaag   180
aagtacggca aggccttcag gaagctgctg agcctgtgcc tgcagcccgg cgccggcgcc   240
ggcgccaacg acatgatcca cgccgagaac atgaggctgg gcagggacaa gtacaaggcc   300
ctgaggcaga tcaggcaggg caac                                          324
```

<210> SEQ ID NO 11
<211> LENGTH: 324
<212> TYPE: DNA

<213> ORGANISM: artificial sequence
<220> FEATURE:
<223> OTHER INFORMATION: Synthetic

<400> SEQUENCE: 11

```
ggcggcaggc tgcccggcta caggcacgcc gccttcgtgc ccacccacag ctaccccgag    60
gccgctggcg gagccgccaa cctgcacacc gacgacggct acatgcctat ggccccggc   120
gtggccccg tgcccggcgg agccgctggc ggcggcgtgg aggacaagga gatgatgaag   180
aagtacggca agccttcag gaagctgctg agcctgtgcc tgcaacccgg agccggagcc   240
ggagccaacg acatgatcca cgccgagaac atgaggctgg caggacaa gtacaaggcc   300
ctgaggcaga tcaggcaggg caac                                         324
```

<210> SEQ ID NO 12
<211> LENGTH: 354
<212> TYPE: DNA
<213> ORGANISM: artificial sequence
<220> FEATURE:
<223> OTHER INFORMATION: Synthetic

<400> SEQUENCE: 12

```
gccggcgctg gcggcaggct gcccggctac aggcacgccg ccttcgtgcc cacccacagc    60
taccccgagg ccgctggcgg agccgccaac ctgcacaccg acgacggcta catgcctatg   120
gccccggcg tggccccgt gcccggcgga gccgctggcg gcggcgtgga ggacaaggag   180
atgatgaaga agtacggcaa agccttcagg aagctgctga gcctgtgcct gcaacccgga   240
gccggagccg gagccaacga catgatccac gccgagaaca tgaggctggg cagggacaag   300
tacaaggccc tgaggcagat caggcagggc aaccccgggg gaggcggaat cgat         354
```

<210> SEQ ID NO 13
<211> LENGTH: 458
<212> TYPE: PRT
<213> ORGANISM: rat
<220> FEATURE:
<221> NAME/KEY: misc_feature
<222> LOCATION: (449)..(449)
<223> OTHER INFORMATION: Xaa can be any naturally occurring amino acid

<400> SEQUENCE: 13

```
Met Glu Leu Ala Ser Ala Arg Leu Leu Arg Gly Gln Ile Pro Trp Arg
1               5                   10                  15

Gly Leu Leu Leu Thr Ala Ser Leu Leu Thr Tyr Trp Ser Pro Leu Thr
            20                  25                  30

Thr Ala Gln Val Thr Val Asp Ala Val Pro Pro Asn Val Val Glu Glu
        35                  40                  45

Ser Ser Val Leu Leu Leu Thr His Asn Leu Pro Gln Glu Phe Gln Val
    50                  55                  60

Phe Tyr Trp Tyr Lys Val Thr Thr Thr Gly Leu Asn Ser Glu Ile Ala
65                  70                  75                  80

Arg Tyr Ile Arg Ser Ser Asn Thr Ser Gln Thr Glu Pro Ala Tyr Ser
                85                  90                  95

Gly Arg Val Thr Ile Tyr Ser Asn Gly Ser Leu Phe Phe Gln Asn Val
            100                 105                 110

Asn Lys Thr Asp Glu Gly Pro Tyr Thr Leu Ser Val Ile Asp Lys Gln
        115                 120                 125

Phe Asn Pro Ile Gln Thr Ser Val Gln Phe Arg Val Tyr Pro Ala Leu
    130                 135                 140
```

Gln Lys Pro Asn Val Thr Gly Asn Asn Ser Asn Pro Met Glu Gly Glu
145                 150                 155                 160

Pro Phe Val Ser Leu Met Cys Glu Pro Tyr Thr Asn Asn Thr Ser Tyr
                165                 170                 175

Leu Trp Ser Arg Asn Gly Glu Ser Leu Ser Glu Gly Asp Arg Val Thr
            180                 185                 190

Phe Ser Glu Gly Asn Arg Thr Leu Thr Leu Leu Asn Val Arg Arg Thr
        195                 200                 205

Asp Lys Gly Tyr Tyr Glu Cys Glu Ala Arg Asn Pro Ala Thr Phe Asn
    210                 215                 220

Arg Ser Asp Pro Phe Asn Leu Asp Val Ile Tyr Gly Pro Asp Ala Pro
225                 230                 235                 240

Val Ile Ser Pro Pro Asp Ile Tyr Leu His Gln Gly Ser Asn Leu Asn
                245                 250                 255

Leu Ser Cys His Ala Asp Ser Asn Pro Pro Ala Gln Tyr Phe Trp Leu
            260                 265                 270

Ile Asn Glu Lys Leu Gln Thr Ser Ser Gln Leu Phe Ile Ser Asn
        275                 280                 285

Ile Thr Thr Asn Asn Ser Gly Thr Tyr Ala Cys Phe Val Asn Asn Thr
    290                 295                 300

Val Thr Gly Leu Ser Arg Thr Thr Val Lys Asn Ile Thr Val Phe Glu
305                 310                 315                 320

Pro Val Thr Gln Pro Ser Ile Gln Ile Thr Asn Thr Thr Val Lys Glu
                325                 330                 335

Leu Gly Ser Val Thr Leu Thr Cys Phe Ser Lys Asp Thr Gly Val Ser
            340                 345                 350

Val Arg Trp Leu Phe Asn Ser Gln Ser Leu Gln Leu Thr Asp Arg Met
        355                 360                 365

Thr Leu Ser Gln Asp Asn Ser Thr Leu Arg Ile Asp Pro Ile Lys Arg
    370                 375                 380

Glu Asp Ala Gly Asp Tyr Gln Cys Glu Ile Ser Asn Pro Val Ser Phe
385                 390                 395                 400

Arg Ile Ser His Pro Ile Lys Leu Asp Val Ile Pro Asp Pro Thr Gln
                405                 410                 415

Gly Asn Ser Gly Leu Ser Glu Gly Ala Ile Ala Gly Ile Val Ile Gly
            420                 425                 430

Ser Val Ala Gly Val Ala Leu Ile Ala Ala Leu Ala Tyr Phe Leu Tyr
        435                 440                 445

Xaa Arg Lys Thr Gly Gly Ser Gly Ser Phe
    450                 455

<210> SEQ ID NO 14
<211> LENGTH: 593
<212> TYPE: PRT
<213> ORGANISM: human
<220> FEATURE:
<221> NAME/KEY: misc_feature
<222> LOCATION: (576)..(576)
<223> OTHER INFORMATION: Xaa can be any naturally occurring amino acid
<220> FEATURE:
<221> NAME/KEY: misc_feature
<222> LOCATION: (591)..(591)
<223> OTHER INFORMATION: Xaa can be any naturally occurring amino acid

<400> SEQUENCE: 14

Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
            35                  40                  45

Gly Ala Val Thr His Ile Lys Ile Gln Asn Thr Gly Asp Tyr Tyr Asp
 50                  55                  60

Leu Tyr Gly Gly Glu Lys Phe Ala Thr Leu Ala Glu Leu Val Gln Tyr
 65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110

Phe His Gly His Leu Ser Gly Lys Glu Ala Glu Lys Leu Leu Thr Glu
            115                 120                 125

Lys Gly Lys His Gly Ser Phe Leu Val Arg Glu Ser Gln Ser His Pro
130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
            195                 200                 205

Val Leu Gln Leu Lys Gln Pro Leu Asn Thr Thr Arg Ile Asn Ala Ala
210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
            275                 280                 285

Arg Val Val Leu His Asp Gly Asp Pro Asn Glu Pro Val Ser Asp Tyr
290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
            355                 360                 365

Lys Tyr Trp Pro Asp Glu Tyr Ala Leu Lys Glu Tyr Gly Val Met Arg
370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser

```
                      435                 440                 445
        Ile Met Asp Ala Gly Pro Val Val His Cys Ser Ala Gly Ile Gly
            450                 455                 460

Arg Thr Gly Thr Phe Ile Val Asp Ile Leu Ile Asp Ile Ile Arg
        465                 470                 475                 480

Glu Lys Gly Val Asp Cys Asp Ile Asp Val Pro Lys Thr Ile Gln Met
                            485                 490                 495

Val Arg Ser Gln Arg Ser Gly Met Val Gln Thr Glu Ala Gln Tyr Arg
                        500                 505                 510

Phe Ile Tyr Met Ala Val Gln His Tyr Ile Glu Thr Leu Gln Arg Arg
                    515                 520                 525

Ile Glu Glu Glu Gln Lys Ser Lys Arg Lys Gly His Glu Tyr Thr Asn
            530                 535                 540

Ile Lys Tyr Ser Leu Ala Asp Gln Thr Ser Gly Asp Gln Ser Pro Leu
        545                 550                 555                 560

Pro Pro Cys Thr Pro Thr Pro Cys Ala Glu Met Arg Glu Asp Xaa
                            565                 570                 575

Ala Arg Val Tyr Glu Asn Val Gly Leu Met Gln Gln Gln Lys Xaa Phe
                        580                 585                 590

Arg

<210> SEQ ID NO 15
<211> LENGTH: 585
<212> TYPE: PRT
<213> ORGANISM: rat
<220> FEATURE:
<221> NAME/KEY: misc_feature
<222> LOCATION: (503)..(503)
<223> OTHER INFORMATION: Xaa can be any naturally occurring amino acid

<400> SEQUENCE: 15

Met Gly Gln Gly Asp Glu Ser Glu Arg Ile Val Ile Asn Val Gly Gly
        1               5                   10                  15

Thr Arg His Gln Thr Tyr Arg Ser Thr Leu Arg Thr Leu Pro Gly Thr
                        20                  25                  30

Arg Leu Ala Trp Leu Ala Glu Pro Asp Ala His Ser His Phe Asp Tyr
                    35                  40                  45

Asp Pro Arg Ala Asp Glu Phe Phe Phe Asp Arg His Pro Gly Val Phe
            50                  55                  60

Ala His Ile Leu Asn Tyr Tyr Arg Thr Gly Lys Leu His Cys Pro Ala
        65                  70                  75                  80

Asp Val Cys Gly Pro Leu Tyr Glu Glu Glu Leu Ala Phe Trp Gly Ile
                        85                  90                  95

Asp Glu Thr Asp Val Glu Pro Cys Cys Trp Met Thr Tyr Arg Gln His
                    100                 105                 110

Arg Asp Ala Glu Glu Ala Leu Asp Ser Phe Gly Gly Ala Pro Leu Asp
                115                 120                 125

Asn Ser Ala Asp Asp Ala Asp Ala Gly Pro Gly Asp Ser Gly Asp
            130                 135                 140

Gly Glu Asp Glu Leu Glu Met Thr Lys Arg Leu Ala Leu Ser Asp Ser
        145                 150                 155                 160

Pro Asp Gly Arg Pro Gly Gly Phe Trp Arg Arg Trp Gln Pro Arg Ile
                        165                 170                 175

Trp Ala Leu Phe Glu Asp Pro Tyr Ser Ser Arg Tyr Ala Arg Tyr Val
                    180                 185                 190
```

```
Ala Phe Ala Ser Leu Phe Phe Ile Leu Val Ser Ile Thr Thr Phe Cys
            195                 200                 205

Leu Glu Thr His Glu Arg Phe Asn Pro Ile Val Asn Lys Thr Glu Ile
210                 215                 220

Glu Asn Val Arg Asn Gly Thr Gln Val Arg Tyr Tyr Arg Glu Ala Glu
225                 230                 235                 240

Thr Glu Ala Phe Leu Thr Tyr Ile Glu Gly Val Cys Val Val Trp Phe
            245                 250                 255

Thr Phe Glu Phe Leu Met Arg Val Val Phe Cys Pro Asn Lys Val Glu
            260                 265                 270

Phe Ile Lys Asn Ser Leu Asn Ile Ile Asp Phe Val Ala Ile Leu Pro
            275                 280                 285

Phe Tyr Leu Glu Val Gly Leu Ser Gly Leu Ser Ser Lys Ala Ala Lys
            290                 295                 300

Asp Val Leu Gly Phe Leu Arg Val Val Arg Phe Val Arg Ile Leu Arg
305                 310                 315                 320

Ile Phe Lys Leu Thr Arg His Phe Val Gly Leu Arg Val Leu Gly His
                325                 330                 335

Thr Leu Arg Ala Ser Thr Asn Glu Phe Leu Leu Leu Ile Ile Phe Leu
            340                 345                 350

Ala Leu Gly Val Leu Ile Phe Ala Thr Met Ile Tyr Tyr Ala Glu Arg
            355                 360                 365

Ile Gly Ala Gln Pro Asn Asp Pro Ser Ala Ser Glu His Thr His Phe
            370                 375                 380

Lys Asn Ile Pro Ile Gly Phe Trp Trp Ala Val Val Thr Met Thr Thr
385                 390                 395                 400

Leu Gly Tyr Gly Asp Met Tyr Pro Gln Thr Trp Ser Gly Met Leu Val
                405                 410                 415

Gly Ala Leu Cys Ala Leu Ala Gly Val Leu Thr Ile Ala Met Pro Val
            420                 425                 430

Pro Val Ile Val Asn Asn Phe Gly Met Tyr Tyr Ser Leu Ala Met Ala
            435                 440                 445

Lys Gln Lys Leu Pro Lys Lys Lys Lys Lys His Ile Pro Arg Pro Pro
450                 455                 460

Gln Leu Gly Ser Pro Asn Tyr Cys Lys Ser Val Val Asn Ser Pro His
465                 470                 475                 480

His Ser Thr Gln Ser Asp Thr Cys Pro Leu Ala Gln Glu Glu Ile Leu
                485                 490                 495

Glu Ile Asn Arg Ala Asp Xaa Lys Leu Asn Gly Glu Val Ala Lys Ala
            500                 505                 510

Ala Leu Ala Asn Glu Asp Cys Pro His Ile Asp Gln Ala Leu Thr Pro
            515                 520                 525

Asp Glu Gly Leu Pro Phe Thr Arg Ser Gly Thr Arg Glu Arg Tyr Gly
530                 535                 540

Pro Cys Phe Leu Leu Ser Thr Gly Glu Tyr Ala Cys Pro Pro Gly Gly
545                 550                 555                 560

Gly Met Arg Lys Asp Leu Cys Lys Glu Ser Pro Val Ile Ala Lys Tyr
                565                 570                 575

Met Pro Thr Glu Ala Val Arg Val Thr
            580                 585

<210> SEQ ID NO 16
<211> LENGTH: 238
<212> TYPE: PRT
```

```
<213> ORGANISM: human
<220> FEATURE:
<221> NAME/KEY: misc_feature
<222> LOCATION: (41)..(41)
<223> OTHER INFORMATION: Xaa can be any naturally occurring amino acid

<400> SEQUENCE: 16

Met Leu Cys Cys Met Arg Arg Thr Lys Gln Val Glu Lys Asn Asp Asp
1               5                   10                  15

Asp Gln Lys Ile Glu Gln Asp Gly Ile Lys Pro Glu Asp Lys Ala His
            20                  25                  30

Lys Ala Ala Thr Lys Ile Gln Ala Xaa Phe Arg Gly His Ile Thr Arg
        35                  40                  45

Lys Lys Leu Lys Gly Glu Lys Lys Asp Asp Val Gln Ala Ala Glu Ala
    50                  55                  60

Glu Ala Asn Lys Lys Asp Glu Ala Pro Val Ala Asp Gly Val Glu Lys
65                  70                  75                  80

Lys Gly Glu Gly Thr Thr Thr Ala Glu Ala Ala Pro Ala Thr Gly Ser
                85                  90                  95

Lys Pro Asp Glu Pro Gly Lys Ala Gly Glu Thr Pro Ser Glu Glu Lys
            100                 105                 110

Lys Gly Glu Gly Asp Ala Ala Thr Glu Gln Ala Ala Pro Gln Ala Pro
        115                 120                 125

Ala Ser Ser Glu Glu Lys Ala Gly Ser Ala Glu Thr Glu Ser Ala Thr
    130                 135                 140

Lys Ala Ser Thr Asp Asn Ser Pro Ser Ser Lys Ala Glu Asp Ala Pro
145                 150                 155                 160

Ala Lys Glu Glu Pro Lys Gln Ala Asp Val Pro Ala Ala Val Thr Ala
                165                 170                 175

Ala Ala Ala Thr Thr Pro Ala Ala Glu Asp Ala Ala Lys Ala Thr
            180                 185                 190

Ala Gln Pro Pro Thr Glu Thr Gly Glu Ser Ser Gln Ala Glu Glu Asn
        195                 200                 205

Ile Glu Ala Val Asp Glu Thr Lys Pro Lys Glu Ser Ala Arg Gln Asp
    210                 215                 220

Glu Gly Lys Glu Glu Glu Pro Glu Ala Asp Gln Glu His Ala
225                 230                 235

<210> SEQ ID NO 17
<211> LENGTH: 861
<212> TYPE: PRT
<213> ORGANISM: mouse
<220> FEATURE:
<221> NAME/KEY: misc_feature
<222> LOCATION: (791)..(791)
<223> OTHER INFORMATION: Xaa can be any naturally occurring amino acid

<400> SEQUENCE: 17

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ser Thr Thr Glu Tyr
65                  70                  75                  80
```

-continued

```
Ala Glu Phe Leu His Cys Lys Gly Lys Lys Phe Thr Asp Phe Glu Glu
                 85                  90                  95
Val Arg Leu Glu Ile Glu Ala Glu Thr Asp Arg Val Thr Gly Thr Asn
            100                 105                 110
Lys Gly Ile Ser Pro Val Pro Ile Asn Leu Arg Val Tyr Ser Pro His
            115                 120                 125
Val Leu Asn Leu Thr Leu Val Asp Leu Pro Gly Met Thr Lys Val Pro
            130                 135                 140
Val Gly Asp Gln Pro Pro Asp Ile Glu Phe Gln Ile Arg Asp Met Leu
145                 150                 155                 160
Met Gln Phe Val Thr Lys Glu Asn Cys Leu Ile Leu Ala Val Ser Pro
                165                 170                 175
Ala Asn Ser Asp Leu Ala Asn Ser Asp Ala Leu Lys Ile Ala Lys Glu
            180                 185                 190
Val Asp Pro Gln Gly Gln Arg Thr Ile Gly Val Ile Thr Lys Leu Asp
            195                 200                 205
Leu Met Asp Glu Gly Thr Asp Ala Arg Asp Val Leu Glu Asn Lys Leu
            210                 215                 220
Leu Pro Leu Arg Arg Gly Tyr Ile Gly Val Val Asn Arg Ser Gln Lys
225                 230                 235                 240
Asp Ile Asp Gly Lys Lys Asp Ile Thr Ala Ala Leu Ala Ala Glu Arg
                245                 250                 255
Lys Phe Phe Leu Ser His Pro Ser Tyr Arg His Leu Ala Asp Arg Met
                260                 265                 270
Gly Thr Pro Tyr Leu Gln Lys Val Leu Asn Gln Gln Leu Thr Asn His
            275                 280                 285
Ile Arg Asp Thr Leu Pro Gly Leu Arg Asn Lys Leu Gln Ser Gln Leu
            290                 295                 300
Leu Ser Ile Glu Lys Glu Val Asp Glu Tyr Lys Asn Phe Arg Pro Asp
305                 310                 315                 320
Asp Pro Ala Arg Lys Thr Lys Ala Leu Leu Gln Met Val Gln Gln Phe
                325                 330                 335
Ala Val Asp Phe Glu Lys Arg Ile Glu Gly Ser Gly Asp Gln Ile Asp
            340                 345                 350
Thr Tyr Glu Leu Ser Gly Gly Ala Arg Ile Asn Arg Ile Phe His Glu
            355                 360                 365
Arg Phe Pro Phe Glu Leu Val Lys Met Glu Phe Asp Glu Lys Glu Leu
            370                 375                 380
Arg Arg Glu Ile Ser Tyr Ala Ile Lys Asn Ile His Gly Ile Arg Thr
385                 390                 395                 400
Gly Leu Phe Thr Pro Asp Met Ala Phe Glu Thr Ile Val Lys Lys Gln
                405                 410                 415
Val Lys Lys Ile Arg Glu Pro Cys Leu Lys Cys Val Asp Met Val Ile
            420                 425                 430
Ser Glu Leu Ile Ser Thr Val Arg Gln Cys Thr Lys Lys Leu Gln Gln
            435                 440                 445
Tyr Pro Arg Leu Arg Glu Glu Met Glu Arg Ile Val Thr Thr His Ile
            450                 455                 460
Arg Glu Arg Glu Gly Arg Thr Lys Glu Gln Val Met Leu Leu Ile Asp
465                 470                 475                 480
Ile Glu Leu Ala Tyr Met Asn Thr Asn His Glu Asp Phe Ile Gly Phe
                485                 490                 495
```

```
Ala Asn Ala Gln Gln Arg Ser Asn Gln Met Asn Lys Lys Thr Ser
            500                 505                 510
Gly Asn Gln Val Ile Arg Lys Gly Trp Leu Thr Ile Asn Asn Ile Gly
        515                 520                 525
Ile Met Lys Gly Gly Ser Lys Glu Tyr Trp Phe Val Leu Thr Ala Glu
    530                 535                 540
Asn Leu Ser Trp Tyr Lys Asp Asp Glu Glu Lys Glu Lys Lys Tyr Met
545                 550                 555                 560
Leu Ser Val Asp Asn Leu Lys Leu Arg Asp Val Glu Lys Gly Phe Met
                565                 570                 575
Ser Ser Lys His Ile Phe Ala Leu Phe Asn Thr Glu Gln Arg Asn Val
            580                 585                 590
Tyr Lys Asp Tyr Arg Gln Leu Glu Leu Ala Cys Glu Thr Gln Glu Glu
        595                 600                 605
Val Asp Ser Trp Lys Ala Ser Phe Leu Arg Ala Gly Val Tyr Pro Glu
    610                 615                 620
Arg Val Gly Asp Lys Glu Lys Ala Ser Glu Thr Glu Glu Asn Gly Ser
625                 630                 635                 640
Asp Ser Phe Met His Ser Met Asp Pro Gln Leu Glu Arg Gln Val Glu
                645                 650                 655
Thr Ile Arg Asn Leu Val Asp Ser Tyr Met Ala Ile Val Asn Lys Thr
            660                 665                 670
Val Arg Asp Leu Met Pro Lys Thr Ile Met His Leu Met Ile Asn Asn
        675                 680                 685
Thr Lys Glu Phe Ile Phe Ser Glu Leu Leu Ala Asn Leu Tyr Ser Cys
    690                 695                 700
Gly Asp Gln Asn Thr Leu Met Glu Glu Ser Ala Glu Gln Arg Gln Arg
705                 710                 715                 720
Arg Asp Glu Met Leu Arg Met Tyr His Ala Leu Lys Glu Ala Leu Ser
                725                 730                 735
Ile Ile Gly Asp Ile Asn Thr Thr Thr Val Ser Thr Pro Met Pro Pro
            740                 745                 750
Pro Val Asp Asp Ser Trp Leu Gln Val Gln Ser Val Pro Ala Gly Arg
        755                 760                 765
Arg Ser Pro Thr Ser Ser Pro Thr Pro Gln Arg Arg Ala Pro Ala Val
    770                 775                 780
Pro Pro Ala Arg Pro Gly Xaa Arg Gly Pro Ala Pro Gly Pro Pro Pro
785                 790                 795                 800
Ala Gly Ser Ala Leu Gly Gly Ala Pro Val Pro Ser Arg Pro Gly
                805                 810                 815
Ala Ser Pro Asp Pro Phe Gly Pro Pro Gln Val Pro Ser Arg Pro
        820                 825                 830
Asn Arg Ala Pro Pro Gly Val Pro Ser Arg Lys Ala Gln Pro His Leu
    835                 840                 845
Arg Asp Leu Gln Pro Pro Asp Gln Arg Leu Pro Ser
850                 855                 860
```

<210> SEQ ID NO 18
<211> LENGTH: 883
<212> TYPE: PRT
<213> ORGANISM: rat
<220> FEATURE:
<221> NAME/KEY: misc_feature
<222> LOCATION: (880)..(880)
<223> OTHER INFORMATION: Xaa can be any naturally occurring amino acid

<400> SEQUENCE: 18

```
Met Gln Lys Ile Met His Ile Ser Val Leu Leu Ser Pro Val Leu Trp
1               5                   10                  15

Gly Leu Ile Phe Gly Val Ser Ser Asn Ser Ile Gln Ile Gly Gly Leu
            20                  25                  30

Phe Pro Arg Gly Ala Asp Gln Glu Tyr Ser Ala Phe Arg Val Gly Met
        35                  40                  45

Val Gln Phe Ser Thr Ser Glu Phe Arg Leu Thr Pro His Ile Asp Asn
    50                  55                  60

Leu Glu Val Ala Asn Ser Phe Ala Val Thr Asn Ala Phe Cys Ser Gln
65                  70                  75                  80

Phe Ser Arg Gly Val Tyr Ala Ile Phe Gly Phe Tyr Asp Lys Lys Ser
                85                  90                  95

Val Asn Thr Ile Thr Ser Phe Cys Gly Thr Leu His Val Ser Phe Ile
            100                 105                 110

Thr Pro Ser Phe Pro Thr Asp Gly Thr His Pro Phe Val Ile Gln Met
        115                 120                 125

Arg Pro Asp Leu Lys Gly Ala Leu Leu Ser Leu Ile Glu Tyr Tyr Gln
    130                 135                 140

Trp Asp Lys Phe Ala Tyr Leu Tyr Asp Ser Asp Arg Gly Leu Ser Thr
145                 150                 155                 160

Leu Gln Ala Val Leu Asp Ser Ala Ala Glu Lys Lys Trp Gln Val Thr
                165                 170                 175

Ala Ile Asn Val Gly Asn Ile Asn Asn Asp Lys Lys Asp Glu Thr Tyr
            180                 185                 190

Arg Ser Leu Phe Gln Asp Leu Glu Leu Lys Lys Glu Arg Arg Val Ile
        195                 200                 205

Leu Asp Cys Glu Arg Asp Lys Val Asn Asp Ile Val Asp Gln Val Ile
    210                 215                 220

Thr Ile Gly Lys His Val Lys Gly Tyr His Tyr Ile Ile Ala Asn Leu
225                 230                 235                 240

Gly Phe Thr Asp Gly Asp Leu Leu Lys Ile Gln Phe Gly Gly Ala Asn
                245                 250                 255

Val Ser Gly Phe Gln Ile Val Asp Tyr Asp Asp Ser Leu Val Ser Lys
            260                 265                 270

Phe Ile Glu Arg Trp Ser Thr Leu Glu Glu Lys Glu Tyr Pro Gly Ala
        275                 280                 285

His Thr Ala Thr Ile Lys Tyr Thr Ser Ala Leu Thr Tyr Asp Ala Val
    290                 295                 300

Gln Val Met Thr Glu Ala Phe Arg Asn Leu Arg Lys Gln Arg Ile Glu
305                 310                 315                 320

Ile Ser Arg Arg Gly Asn Ala Gly Asp Cys Leu Ala Asn Pro Ala Val
                325                 330                 335

Pro Trp Gly Gln Gly Val Glu Ile Glu Arg Ala Leu Lys Gln Val Gln
            340                 345                 350

Val Glu Gly Leu Ser Gly Asn Ile Lys Phe Asp Gln Asn Gly Lys Arg
        355                 360                 365

Ile Asn Tyr Thr Ile Asn Ile Met Glu Leu Lys Thr Asn Gly Pro Arg
    370                 375                 380

Lys Ile Gly Tyr Trp Ser Glu Val Asp Lys Met Val Val Thr Leu Thr
385                 390                 395                 400

Glu Leu Pro Ser Gly Asn Asp Thr Ser Gly Leu Glu Asn Lys Thr Val
                405                 410                 415
```

```
Val Val Thr Thr Ile Leu Glu Ser Pro Tyr Val Met Met Lys Lys Asn
            420             425             430

His Glu Met Leu Glu Gly Asn Glu Arg Tyr Glu Gly Tyr Cys Val Asp
            435             440             445

Leu Ala Ala Glu Ile Ala Lys His Cys Gly Phe Lys Tyr Lys Leu Thr
            450             455             460

Ile Val Gly Asp Gly Lys Tyr Gly Ala Arg Asp Ala Asp Thr Lys Ile
465             470             475             480

Trp Asn Gly Met Val Gly Glu Leu Val Tyr Gly Lys Ala Asp Ile Ala
                485             490             495

Ile Ala Pro Leu Thr Ile Thr Leu Val Arg Glu Glu Val Ile Asp Phe
                500             505             510

Ser Lys Pro Phe Met Ser Leu Gly Ile Ser Ile Met Ile Lys Lys Pro
            515             520             525

Gln Lys Ser Lys Pro Gly Val Phe Ser Phe Leu Asp Pro Leu Ala Tyr
            530             535             540

Glu Ile Trp Met Cys Ile Val Phe Ala Tyr Ile Gly Val Ser Val Val
545             550             555             560

Leu Phe Leu Val Ser Arg Phe Ser Pro Tyr Glu Trp His Thr Glu Glu
                565             570             575

Phe Glu Asp Gly Arg Glu Thr Gln Ser Ser Glu Ser Thr Asn Glu Phe
                580             585             590

Gly Ile Phe Asn Ser Leu Trp Phe Ser Leu Gly Ala Phe Met Arg Gln
            595             600             605

Gly Cys Asp Ile Ser Pro Arg Ser Leu Ser Gly Arg Ile Val Gly Gly
            610             615             620

Val Trp Trp Phe Phe Thr Leu Ile Ile Ile Ser Ser Tyr Thr Ala Asn
625             630             635             640

Leu Ala Ala Phe Leu Thr Val Glu Arg Met Val Ser Pro Ile Glu Ser
                645             650             655

Ala Glu Asp Leu Ser Lys Gln Thr Glu Ile Ala Tyr Gly Thr Leu Asp
            660             665             670

Ser Gly Ser Thr Lys Glu Phe Phe Arg Arg Ser Lys Ile Ala Val Phe
            675             680             685

Asp Lys Met Trp Thr Tyr Met Arg Ser Ala Glu Pro Ser Val Phe Val
            690             695             700

Arg Thr Thr Ala Glu Gly Val Ala Arg Val Arg Lys Ser Lys Gly Lys
705             710             715             720

Tyr Ala Tyr Leu Leu Glu Ser Thr Met Asn Glu Tyr Ile Glu Gln Arg
                725             730             735

Lys Pro Cys Asp Thr Met Lys Val Gly Gly Asn Leu Asp Ser Lys Gly
            740             745             750

Tyr Gly Ile Ala Thr Pro Lys Gly Ser Ser Leu Gly Asn Ala Val Asn
            755             760             765

Leu Ala Val Leu Lys Leu Asn Glu Gln Gly Leu Leu Asp Lys Leu Lys
            770             775             780

Asn Lys Trp Trp Tyr Asp Lys Gly Glu Cys Gly Ser Gly Gly Gly Asp
785             790             795             800

Ser Lys Glu Lys Thr Ser Ala Leu Ser Leu Ser Asn Val Ala Gly Val
                805             810             815

Phe Tyr Ile Leu Val Gly Gly Leu Gly Leu Ala Met Leu Val Ala Leu
            820             825             830
```

```
Ile Glu Phe Cys Tyr Lys Ser Arg Ala Glu Ala Lys Arg Met Lys Val
            835                 840                 845

Ala Lys Asn Pro Gln Asn Ile Asn Pro Ser Ser Gln Asn Ser Gln
850                 855                 860

Asn Phe Ala Thr Tyr Lys Glu Gly Tyr Asn Val Tyr Gly Ile Glu Xaa
865                 870                 875                 880

Val Lys Ile

<210> SEQ ID NO 19
<211> LENGTH: 936
<212> TYPE: PRT
<213> ORGANISM: human
<220> FEATURE:
<221> NAME/KEY: misc_feature
<222> LOCATION: (894)..(894)
<223> OTHER INFORMATION: Xaa can be any naturally occurring amino acid

<400> SEQUENCE: 19

Met Ser Thr Met Arg Leu Leu Thr Leu Ala Leu Leu Phe Ser Cys Ser
1               5                   10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                  80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Ser Gly Tyr Val Trp Leu Val Gly Glu Arg Glu Ile Ser Gly
                245                 250                 255

Asn Ala Leu Arg Tyr Ala Pro Asp Gly Ile Leu Gly Leu Gln Leu Ile
            260                 265                 270

Asn Gly Lys Asn Glu Ser Ala His Ile Ser Asp Ala Val Gly Val Val
        275                 280                 285

Ala Gln Ala Val His Glu Leu Leu Glu Lys Glu Asn Ile Thr Asp Pro
    290                 295                 300
```

```
Pro Arg Gly Cys Val Gly Asn Thr Asn Ile Trp Lys Thr Gly Pro Leu
305                 310                 315                 320

Phe Lys Arg Val Leu Met Ser Ser Lys Tyr Ala Asp Gly Val Thr Gly
                325                 330                 335

Arg Val Glu Phe Asn Glu Asp Gly Asp Arg Lys Phe Ala Asn Tyr Ser
            340                 345                 350

Ile Met Asn Leu Gln Asn Arg Lys Leu Val Gln Val Gly Ile Tyr Asn
        355                 360                 365

Gly Thr His Val Ile Pro Asn Asp Arg Lys Ile Ile Trp Pro Gly Gly
    370                 375                 380

Glu Thr Glu Lys Pro Arg Gly Tyr Gln Met Ser Thr Arg Leu Lys Ile
385                 390                 395                 400

Val Thr Ile His Gln Glu Pro Phe Val Tyr Val Lys Pro Thr Leu Ser
                405                 410                 415

Asp Gly Thr Cys Lys Glu Glu Phe Thr Val Asn Gly Asp Pro Val Lys
            420                 425                 430

Lys Val Ile Cys Thr Gly Pro Asn Asp Thr Ser Pro Ala Arg His Thr
        435                 440                 445

Val Pro Gln Cys Cys Tyr Gly Phe Cys Ile Asp Leu Leu Ile Lys Leu
    450                 455                 460

Ala Arg Thr Met Asn Phe Thr Tyr Glu Val His Leu Val Ala Asp Gly
465                 470                 475                 480

Lys Phe Gly Thr Gln Glu Arg Val Asn Asn Ser Asn Lys Lys Glu Trp
                485                 490                 495

Asn Gly Met Met Gly Glu Leu Leu Ser Gly Gln Ala Asp Met Ile Val
            500                 505                 510

Ala Pro Leu Thr Ile Asn Asn Glu Arg Ala Gln Tyr Ile Glu Phe Ser
        515                 520                 525

Lys Pro Phe Lys Tyr Gln Gly Leu Thr Ile Leu Val Lys Lys Glu Ile
    530                 535                 540

Pro Arg Ser Thr Leu Asp Ser Phe Met Gln Pro Phe Gln Ser Thr Leu
545                 550                 555                 560

Trp Leu Leu Val Gly Leu Ser Val His Val Ala Val Met Leu Tyr
                565                 570                 575

Leu Leu Asp Arg Phe Ser Pro Phe Gly Arg Phe Lys Val Asn Ser Glu
            580                 585                 590

Glu Glu Glu Glu Asp Ala Leu Thr Leu Ser Ser Ala Met Trp Phe Ser
        595                 600                 605

Trp Gly Val Leu Leu Asn Ser Gly Ile Gly Glu Gly Ala Pro Arg Ser
    610                 615                 620

Phe Ser Ala Arg Ile Leu Gly Met Val Trp Ala Gly Phe Ala Met Ile
625                 630                 635                 640

Ile Val Ala Ser Tyr Thr Ala Asn Leu Ala Ala Phe Leu Val Leu Asp
                645                 650                 655

Arg Pro Glu Glu Arg Ile Thr Gly Ile Asn Asp Pro Arg Leu Arg Asn
            660                 665                 670

Pro Ser Asp Lys Phe Ile Tyr Ala Thr Val Lys Gln Ser Ser Val Asp
        675                 680                 685

Ile Tyr Phe Arg Arg Gln Val Glu Leu Ser Thr Met Tyr Arg His Met
    690                 695                 700

Glu Lys His Asn Tyr Glu Ser Ala Ala Glu Ala Ile Gln Ala Val Arg
705                 710                 715                 720
```

-continued

```
Asp Asn Lys Leu His Ala Phe Ile Trp Asp Ser Ala Val Leu Glu Phe
            725                 730                 735

Glu Ala Ser Gln Lys Cys Asp Leu Val Thr Thr Gly Glu Leu Phe Phe
        740                 745                 750

Arg Ser Gly Phe Gly Ile Gly Met Arg Lys Asp Ser Pro Trp Lys Gln
    755                 760                 765

Asn Val Ser Leu Ser Ile Leu Lys Ser His Glu Asn Gly Phe Met Glu
770                 775                 780

Asp Leu Asp Lys Thr Trp Val Arg Tyr Gln Glu Cys Asp Ser Arg Ser
785                 790                 795                 800

Asn Ala Pro Ala Thr Leu Thr Phe Glu Asn Met Ala Gly Val Phe Met
            805                 810                 815

Leu Val Ala Gly Gly Ile Val Ala Gly Ile Phe Leu Ile Phe Ile Glu
        820                 825                 830

Ile Ala Tyr Lys Arg His Lys Asp Ala Arg Arg Lys Gln Met Gln Leu
    835                 840                 845

Ala Phe Ala Ala Val Asn Val Trp Arg Lys Asn Leu Gln Asp Arg Lys
850                 855                 860

Ser Gly Arg Ala Glu Pro Asp Pro Lys Lys Lys Ala Thr Phe Arg Ala
865                 870                 875                 880

Ile Thr Ser Thr Leu Ala Ser Ser Phe Lys Arg Arg Arg Xaa Ser Lys
            885                 890                 895

Asp Thr Ser Thr Gly Gly Gly Arg Gly Ala Leu Gln Asn Gln Lys Asp
        900                 905                 910

Thr Val Leu Pro Arg Arg Ala Ile Glu Arg Glu Glu Gly Gln Leu Gln
    915                 920                 925

Leu Cys Ser Arg His Arg Glu Ser
    930                 935

<210> SEQ ID NO 20
<211> LENGTH: 332
<212> TYPE: PRT
<213> ORGANISM: human
<220> FEATURE:
<221> NAME/KEY: misc_feature
<222> LOCATION: (159)..(159)
<223> OTHER INFORMATION: Xaa can be any naturally occurring amino acid
<220> FEATURE:
<221> NAME/KEY: misc_feature
<222> LOCATION: (163)..(163)
<223> OTHER INFORMATION: Xaa can be any naturally occurring amino acid

<400> SEQUENCE: 20

Met Gly Ala Gln Phe Ser Lys Thr Ala Ala Lys Gly Glu Ala Ala Ala
1               5                   10                  15

Glu Arg Pro Gly Glu Ala Ala Val Ala Ser Ser Pro Ser Lys Ala Asn
            20                  25                  30

Gly Gln Glu Asn Gly His Val Lys Val Asn Gly Asp Ala Ser Pro Ala
        35                  40                  45

Ala Ala Glu Ser Gly Ala Lys Glu Glu Leu Gln Ala Asn Gly Ser Ala
    50                  55                  60

Pro Ala Ala Asp Lys Glu Glu Pro Ala Ala Gly Ser Gly Ala Ala
65                  70                  75                  80

Ser Pro Ser Ala Ala Glu Lys Gly Glu Pro Ala Ala Ala Ala Pro
                85                  90                  95

Glu Ala Gly Ala Ser Pro Val Glu Lys Glu Ala Pro Ala Glu Gly Glu
            100                 105                 110
```

```
Ala Ala Glu Pro Gly Ser Pro Thr Ala Ala Gly Glu Ala Ala Ser
            115                 120                 125
Ala Ala Ser Ser Thr Ser Ser Pro Lys Ala Glu Asp Gly Ala Thr Pro
130                 135                 140
Ser Pro Ser Asn Glu Thr Pro Lys Lys Lys Lys Arg Phe Xaa Phe
145                 150                 155                 160
Lys Lys Xaa Phe Lys Leu Ser Gly Phe Ser Phe Lys Lys Asn Lys Lys
                165                 170                 175
Glu Ala Gly Glu Gly Gly Glu Ala Ala Pro Ala Ala Gly Gly
            180                 185                 190
Lys Asp Glu Ala Ala Gly Gly Ala Ala Ala Ala Glu Ala Gly
            195                 200                 205
Ala Ala Ser Gly Glu Gln Ala Ala Ala Pro Gly Glu Glu Ala Ala Ala
210                 215                 220
Gly Glu Glu Gly Ala Ala Gly Gly Asp Pro Gln Glu Ala Lys Pro Gln
225                 230                 235                 240
Glu Ala Ala Val Ala Pro Glu Lys Pro Pro Ala Ser Asp Glu Thr Lys
                245                 250                 255
Ala Ala Glu Glu Pro Ser Lys Val Glu Glu Lys Lys Ala Glu Glu Ala
            260                 265                 270
Gly Ala Ser Ala Ala Ala Cys Glu Ala Pro Ser Ala Ala Gly Pro Gly
            275                 280                 285
Ala Pro Pro Glu Gln Glu Ala Ala Pro Ala Glu Pro Ala Ala Ala
            290                 295                 300
Ala Ala Ser Ser Ala Cys Ala Ala Pro Ser Gln Glu Ala Gln Pro Glu
305                 310                 315                 320
Cys Ser Pro Glu Ala Pro Pro Ala Glu Ala Ala Glu
                325                 330

<210> SEQ ID NO 21
<211> LENGTH: 749
<212> TYPE: PRT
<213> ORGANISM: human
<220> FEATURE:
<221> NAME/KEY: misc_feature
<222> LOCATION: (727)..(727)
<223> OTHER INFORMATION: Xaa can be any naturally occurring amino acid

<400> SEQUENCE: 21

Met Ser Gln Trp Phe Glu Leu Gln Gln Leu Asp Ser Lys Phe Leu Glu
1               5                   10                  15
Gln Val His Gln Leu Tyr Asp Asp Ser Phe Pro Met Glu Ile Arg Gln
                20                  25                  30
Tyr Leu Ala Gln Trp Leu Glu Lys Gln Asp Trp Glu His Ala Ala Tyr
            35                  40                  45
Asp Val Ser Phe Ala Thr Ile Arg Phe His Asp Leu Leu Ser Gln Leu
    50                  55                  60
Asp Asp Gln Tyr Ser Arg Phe Ser Leu Glu Asn Asn Phe Leu Leu Gln
65                  70                  75                  80
His Asn Ile Arg Lys Ser Lys Arg Asn Leu Gln Asp Asn Phe Gln Glu
                85                  90                  95
Asp Pro Val Gln Met Ser Met Ile Ile Tyr Asn Cys Leu Lys Glu Glu
            100                 105                 110
Arg Lys Ile Leu Glu Asn Ala Gln Arg Phe Asn Gln Ala Gln Glu Gly
        115                 120                 125
Asn Ile Gln Asn Thr Val Met Leu Asp Lys Gln Lys Glu Leu Asp Ser
```

```
            130                 135                 140
Lys Val Arg Asn Val Lys Asp Gln Val Met Cys Ile Glu Gln Glu Ile
145                 150                 155                 160

Lys Thr Leu Glu Glu Leu Gln Asp Glu Tyr Asp Phe Lys Cys Lys Thr
                    165                 170                 175

Ser Gln Asn Arg Glu Gly Glu Ala Asn Gly Val Ala Lys Ser Asp Gln
                180                 185                 190

Lys Gln Glu Gln Leu Leu Leu His Lys Met Phe Leu Met Leu Asp Asn
            195                 200                 205

Lys Arg Lys Glu Ile Ile His Lys Ile Arg Glu Leu Leu Asn Ser Ile
210                 215                 220

Glu Leu Thr Gln Asn Thr Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                    245                 250                 255

Asp Gln Leu Gln Thr Trp Phe Thr Ile Val Ala Glu Thr Leu Gln Gln
                260                 265                 270

Ile Arg Gln Gln Leu Lys Lys Leu Glu Glu Leu Glu Gln Lys Phe Thr
            275                 280                 285

Tyr Glu Pro Asp Pro Ile Thr Lys Asn Lys Gln Val Leu Ser Asp Arg
        290                 295                 300

Thr Phe Leu Leu Phe Gln Gln Leu Ile Gln Ser Ser Phe Val Val Glu
305                 310                 315                 320

Arg Gln Pro Cys Met Pro Thr His Pro Gln Arg Pro Leu Val Leu Lys
                    325                 330                 335

Thr Gly Val Gln Phe Thr Val Lys Ser Arg Leu Leu Val Lys Leu Gln
                340                 345                 350

Glu Ser Asn Leu Leu Thr Lys Val Lys Cys His Phe Asp Lys Asp Val
            355                 360                 365

Asn Glu Lys Asn Thr Val Lys Gly Phe Arg Lys Phe Asn Ile Leu Gly
        370                 375                 380

Thr His Thr Lys Val Met Asn Met Glu Glu Ser Thr Asn Gly Ser Leu
385                 390                 395                 400

Ala Ala Glu Leu Arg His Leu Gln Leu Lys Glu Gln Lys Asn Ala Gly
                    405                 410                 415

Asn Arg Thr Asn Glu Gly Pro Leu Ile Val Thr Glu Glu Leu His Ser
                420                 425                 430

Leu Ser Phe Glu Thr Gln Leu Cys Gln Pro Gly Leu Val Ile Asp Leu
            435                 440                 445

Glu Thr Thr Ser Leu Pro Val Val Val Ile Ser Asn Val Ser Gln Leu
        450                 455                 460

Pro Ser Gly Trp Ala Ser Ile Leu Trp Tyr Asn Met Leu Val Thr Glu
465                 470                 475                 480

Pro Arg Asn Leu Ser Phe Phe Leu Asn Pro Pro Cys Ala Trp Trp Ser
                    485                 490                 495

Gln Leu Ser Glu Val Leu Ser Trp Gln Phe Ser Ser Val Thr Lys Arg
                500                 505                 510

Gly Leu Asn Ala Asp Gln Leu Ser Met Leu Gly Glu Lys Leu Leu Gly
            515                 520                 525

Pro Asn Ala Gly Pro Asp Gly Leu Ile Pro Trp Thr Arg Phe Cys Lys
        530                 535                 540

Glu Asn Ile Asn Asp Lys Asn Phe Ser Phe Trp Pro Trp Ile Asp Thr
545                 550                 555                 560
```

```
Ile Leu Glu Leu Ile Lys Asn Asp Leu Leu Cys Leu Trp Asn Asp Gly
                565                 570                 575

Cys Ile Met Gly Phe Ile Ser Lys Glu Arg Glu Ala Leu Leu Lys
            580                 585                 590

Asp Gln Gln Pro Gly Thr Phe Leu Leu Arg Phe Ser Glu Ser Ser Arg
        595                 600                 605

Glu Gly Ala Ile Thr Phe Thr Trp Val Glu Arg Ser Gln Asn Gly Gly
        610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
                660                 665                 670

Lys Asp His Ala Phe Gly Lys Tyr Tyr Ser Arg Pro Lys Glu Ala Pro
            675                 680                 685

Glu Pro Met Glu Leu Asp Asp Pro Lys Arg Thr Gly Tyr Ile Lys Thr
        690                 695                 700

Glu Leu Ile Ser Val Ser Glu Val His Pro Ser Arg Leu Gln Thr Thr
705                 710                 715                 720

Asp Asn Leu Leu Pro Met Xaa Pro Glu Glu Phe Asp Glu Met Ser Arg
                725                 730                 735

Ile Val Gly Pro Glu Phe Asp Ser Met Met Ser Thr Val
            740                 745

<210> SEQ ID NO 22
<211> LENGTH: 636
<212> TYPE: PRT
<213> ORGANISM: human
<220> FEATURE:
<221> NAME/KEY: misc_feature
<222> LOCATION: (289)..(289)
<223> OTHER INFORMATION: Xaa can be any naturally occurring amino acid

<400> SEQUENCE: 22

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160
```

-continued

```
Ile Gln Ile Lys Val Ser Thr Pro Pro Pro Gly Thr Ala Ile Arg
            165                 170                 175
Ala Met Pro Val Tyr Lys Lys Ala Glu His Val Thr Asp Val Lys
            180                 185                 190
Arg Cys Pro Asn His Glu Leu Gly Arg Asp Phe Asn Glu Gly Gln Ser
            195                 200                 205
Ala Pro Ala Ser His Leu Ile Arg Val Glu Gly Asn Asn Leu Ser Gln
210                 215                 220
Tyr Val Asp Asp Pro Val Thr Gly Arg Gln Ser Val Val Pro Tyr
225                 230                 235                 240
Glu Pro Pro Gln Val Gly Thr Glu Phe Thr Thr Ile Leu Tyr Asn Phe
            245                 250                 255
Met Cys Asn Ser Ser Cys Val Gly Gly Met Asn Arg Arg Pro Ile Leu
            260                 265                 270
Ile Ile Ile Thr Leu Glu Met Arg Asp Gly Gln Val Leu Gly Arg Arg
            275                 280                 285
Xaa Phe Glu Gly Arg Ile Cys Ala Cys Pro Gly Arg Asp Arg Lys Ala
            290                 295                 300
Asp Glu Asp His Tyr Arg Glu Gln Gln Ala Leu Asn Glu Ser Ser Ala
305                 310                 315                 320
Lys Asn Gly Ala Ala Ser Lys Arg Ala Phe Lys Gln Ser Pro Pro Ala
            325                 330                 335
Val Pro Ala Leu Gly Ala Gly Val Lys Lys Arg Arg His Gly Asp Glu
            340                 345                 350
Asp Thr Tyr Tyr Leu Gln Val Arg Gly Arg Glu Asn Phe Glu Ile Leu
            355                 360                 365
Met Lys Leu Lys Glu Ser Leu Glu Leu Met Glu Leu Val Pro Gln Pro
            370                 375                 380
Leu Val Asp Ser Tyr Arg Gln Gln Gln Leu Leu Gln Arg Pro Ser
385                 390                 395                 400
His Leu Gln Pro Pro Ser Tyr Gly Pro Val Leu Ser Pro Met Asn Lys
            405                 410                 415
Val His Gly Gly Met Asn Lys Leu Pro Ser Val Asn Gln Leu Val Gly
            420                 425                 430
Gln Pro Pro Pro His Ser Ser Ala Ala Thr Pro Asn Leu Gly Pro Val
            435                 440                 445
Gly Pro Gly Met Leu Asn Asn His Gly His Ala Val Pro Ala Asn Gly
            450                 455                 460
Glu Met Ser Ser Ser His Ser Ala Gln Ser Met Val Ser Gly Ser His
465                 470                 475                 480
Cys Thr Pro Pro Pro Tyr His Ala Asp Pro Ser Leu Val Ser Phe
            485                 490                 495
Leu Thr Gly Leu Gly Cys Pro Asn Cys Ile Glu Tyr Phe Thr Ser Gln
            500                 505                 510
Gly Leu Gln Ser Ile Tyr His Leu Gln Asn Leu Thr Ile Glu Asp Leu
            515                 520                 525
Gly Ala Leu Lys Ile Pro Glu Gln Tyr Arg Met Thr Ile Trp Arg Gly
            530                 535                 540
Leu Gln Asp Leu Lys Gln Gly His Asp Tyr Ser Thr Ala Gln Gln Leu
545                 550                 555                 560
Leu Arg Ser Ser Asn Ala Ala Thr Ile Ser Ile Gly Gly Ser Gly Glu
            565                 570                 575
Leu Gln Arg Gln Arg Val Met Glu Ala Val His Phe Arg Val Arg His
```

```
                    580                 585                 590
Thr Ile Thr Ile Pro Asn Arg Gly Gly Pro Gly Gly Gly Pro Asp Glu
                595                 600                 605

Trp Ala Asp Phe Gly Phe Asp Leu Pro Asp Cys Lys Ala Arg Lys Gln
            610                 615                 620

Pro Ile Lys Glu Glu Phe Thr Glu Ala Glu Ile His
625                 630                 635

<210> SEQ ID NO 23
<211> LENGTH: 413
<212> TYPE: PRT
<213> ORGANISM: rat
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid

<400> SEQUENCE: 23

Met Lys Arg Ile Tyr Leu Leu Val Val Gly Leu Tyr Leu Leu Ser Phe
1               5                   10                  15

Ser Arg Ala Glu Glu Gly Leu Asn Phe Pro Thr Tyr Asp Gly Lys Asp
            20                  25                  30

Arg Val Val Ser Leu Ser Glu Lys Asn Leu Lys Gln Val Leu Lys Arg
        35                  40                  45

Tyr Asp Leu Leu Cys Leu Tyr Tyr His Glu Pro Val Ser Ser Asp Lys
    50                  55                  60

Val Ala Gln Lys Gln Phe Gln Leu Lys Glu Ile Val Leu Glu Leu Val
65                  70                  75                  80

Ala Gln Val Leu Glu His Lys Asn Ile Gly Phe Val Met Val Asp Ser
                85                  90                  95

Arg Lys Glu Ala Lys Leu Ala Lys Arg Leu Gly Phe Ser Glu Glu Gly
            100                 105                 110

Ser Leu Tyr Val Leu Lys Gly Gly Arg Thr Ile Glu Phe Asp Gly Glu
        115                 120                 125

Phe Ala Ala Asp Val Leu Val Glu Phe Leu Leu Asp Leu Ile Glu Asp
    130                 135                 140

Pro Val Glu Ile Val Asn Asn Lys Leu Glu Val Gln Ala Phe Glu Arg
145                 150                 155                 160

Ile Glu Asp Gln Ile Lys Leu Leu Gly Phe Phe Lys Asn Glu Asp Ser
                165                 170                 175

Glu Tyr Tyr Lys Ala Phe Gln Glu Ala Ala Glu His Phe Gln Pro Tyr
            180                 185                 190

Ile Lys Phe Phe Ala Thr Phe Asp Lys Gly Val Ala Lys Lys Leu Phe
        195                 200                 205

Leu Glu Val Asn Glu Val Gly Phe Tyr Glu Pro Phe Met Asp Glu Pro
    210                 215                 220

Ser Val Ile Pro Asn Lys Pro Tyr Thr Glu Glu Leu Val Glu Phe
225                 230                 235                 240

Val Lys Glu His Gln Arg Pro Xaa Leu Arg Pro Leu Arg Pro Glu Asp
                245                 250                 255

Met Phe Glu Thr Trp Glu Asp Asp Leu Asn Gly Ile His Ile Val Ala
            260                 265                 270

Phe Ala Glu Lys Ser Asp Pro Asp Gly Tyr Glu Phe Leu Glu Ile Leu
```

```
                275                 280                 285
Lys Gln Val Ala Arg Asp Asn Thr Asp Asn Pro Asp Leu Ser Ile Leu
            290                 295                 300

Trp Ile Asp Pro Asp Asp Phe Pro Leu Leu Val Ala Tyr Trp Glu Lys
305                 310                 315                 320

Xaa Phe Lys Ile Asp Leu Phe Lys Pro Gln Ile Gly Val Val Asn Val
                325                 330                 335

Thr Asp Ala Asp Ser Val Trp Met Glu Ile Pro Asp Asp Asp Asp Leu
            340                 345                 350

Pro Thr Ala Glu Glu Leu Glu Asp Trp Ile Glu Asp Val Leu Ser Gly
                355                 360                 365

Lys Ile Asn Thr Glu Asp Asp Asn Glu Asp Glu Asp Asp Asp Asp Gly
            370                 375                 380

Asp Asn Asp Asn Asp Asp Asp Asp Asp Asp Asn Ser Asp Glu
385                 390                 395                 400

Asp Asn Asp Asp Ser Asp Asp Asp Asp Asp Asp Glu
                405                 410
```

<210> SEQ ID NO 24
<211> LENGTH: 617
<212> TYPE: PRT
<213> ORGANISM: rat
<220> FEATURE:
<221> NAME/KEY: misc_feature
<222> LOCATION: (258)..(259)
<223> OTHER INFORMATION: Xaa can be any naturally occurring amino acid

<400> SEQUENCE: 24

```
Met Leu Leu Ala Arg Met Lys Pro Gln Val Gln Pro Glu Leu Gly Gly
1               5                   10                  15

Ala Asp Gln Leu Pro Glu Gln Pro Leu Arg Pro Cys Lys Thr Ala Asp
                20                  25                  30

Leu Leu Val Val Lys Glu Arg Asn Gly Val Gln Cys Leu Leu Ala Ser
            35                  40                  45

Gln Asp Gly Asp Ala Gln Pro Arg Glu Thr Trp Gly Lys Glu Ile Asp
50                  55                  60

Phe Leu Leu Ser Val Val Gly Phe Ala Val Asp Leu Ala Asn Val Trp
65                  70                  75                  80

Arg Phe Pro Tyr Leu Cys Tyr Lys Asn Gly Gly Gly Ala Phe Leu Ile
                85                  90                  95

Pro Tyr Thr Leu Phe Leu Ile Ile Ala Gly Met Pro Leu Phe Tyr Met
                100                 105                 110

Glu Leu Ala Leu Gly Gln Phe Asn Arg Glu Gly Ala Ala Thr Val Trp
            115                 120                 125

Lys Ile Cys Pro Phe Phe Lys Gly Val Gly Tyr Ala Val Ile Leu Ile
130                 135                 140

Ala Leu Tyr Val Gly Phe Tyr Tyr Asn Val Ile Ile Ala Trp Ser Leu
145                 150                 155                 160

Tyr Tyr Leu Phe Ala Ser Phe Thr Leu Asn Leu Pro Trp Thr Asn Cys
                165                 170                 175

Gly His Ala Trp Asn Ser Pro Asn Cys Thr Asp Pro Lys Leu Leu Asn
            180                 185                 190

Ala Ser Val Leu Gly Asp His Thr Lys Tyr Ser Lys Tyr Lys Phe Thr
                195                 200                 205

Pro Ala Ala Glu Phe Tyr Glu Arg Gly Val Leu His Leu His Glu Ser
210                 215                 220
```

Ser Gly Ile His Asp Ile Gly Leu Pro Gln Trp Gln Leu Leu Leu Cys
225                 230                 235                 240

Leu Met Val Val Ile Val Leu Tyr Phe Ser Leu Trp Lys Gly Val
            245                 250                 255

Lys Xaa Xaa Gly Lys Val Val Trp Ile Thr Ala Thr Leu Pro Tyr Phe
            260                 265                 270

Val Leu Phe Val Leu Leu Val His Gly Val Thr Leu Pro Gly Ala Ser
            275                 280                 285

Asn Gly Ile Asn Ala Tyr Leu His Ile Asp Phe Tyr Arg Leu Lys Glu
            290                 295                 300

Ala Thr Val Trp Ile Asp Ala Thr Gln Ile Phe Phe Ser Leu Gly
305                 310                 315                 320

Ala Gly Phe Gly Val Leu Ile Ala Phe Ala Ser Tyr Asn Lys Phe Asp
                325                 330                 335

Asn Asn Cys Tyr Arg Asp Ala Leu Leu Thr Ser Thr Ile Asn Cys Val
                340                 345                 350

Thr Ser Phe Ile Ser Gly Phe Ala Ile Phe Ser Ile Leu Gly Tyr Met
            355                 360                 365

Ala His Glu His Lys Val Lys Ile Glu Asp Val Ala Thr Glu Gly Ala
            370                 375                 380

Gly Leu Val Phe Val Leu Tyr Pro Glu Ala Ile Ser Thr Leu Ser Gly
385                 390                 395                 400

Ser Thr Phe Trp Ala Val Leu Phe Phe Leu Met Leu Leu Ala Leu Gly
                405                 410                 415

Leu Asp Ser Ser Met Gly Gly Met Glu Ala Val Ile Thr Gly Leu Ala
                420                 425                 430

Asp Asp Phe Gln Val Leu Lys Arg His Arg Lys Leu Phe Thr Cys Ala
                435                 440                 445

Val Thr Leu Gly Thr Phe Leu Leu Ala Met Phe Cys Ile Thr Lys Gly
            450                 455                 460

Gly Ile Tyr Val Leu Thr Leu Leu Asp Thr Phe Ala Ala Gly Thr Ser
465                 470                 475                 480

Ile Leu Phe Ala Val Leu Met Glu Ala Ile Gly Val Ser Trp Phe Tyr
                485                 490                 495

Gly Val Asp Arg Phe Ser Asn Asp Ile Gln Gln Met Met Gly Phe Lys
                500                 505                 510

Pro Gly Leu Tyr Trp Arg Leu Cys Trp Lys Phe Val Ser Pro Ala Phe
            515                 520                 525

Leu Leu Phe Val Val Val Ser Ile Ile Asn Phe Lys Pro Leu Thr
            530                 535                 540

Tyr Asp Asp Tyr Val Tyr Pro Pro Trp Ala Asn Trp Val Gly Trp Gly
545                 550                 555                 560

Ile Ala Leu Ser Ser Met Ile Leu Val Pro Ala Tyr Val Ile Tyr Lys
                565                 570                 575

Phe Phe Ser Ile Arg Gly Ser Leu Trp Glu Arg Val Ala Tyr Gly Ile
            580                 585                 590

Thr Pro Glu Asn Glu His His Leu Val Ala Gln Arg Asp Val Arg Gln
            595                 600                 605

Phe Gln Leu Arg His Trp Leu Ala Ile
            610                 615

<210> SEQ ID NO 25
<211> LENGTH: 2179

-continued

```
<212> TYPE: PRT
<213> ORGANISM: human
<220> FEATURE:
<221> NAME/KEY: misc_feature
<222> LOCATION: (1939)..(1939)
<223> OTHER INFORMATION: Xaa can be any naturally occurring amino acid

<400> SEQUENCE: 25

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
    130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Tyr Ala Ile Ile Gly Leu Glu
        275                 280                 285

Leu Phe Met Gly Lys Met His Lys Thr Cys Tyr Asn Gln Glu Gly Ile
290                 295                 300

Ala Asp Val Pro Ala Glu Asp Pro Ser Pro Cys Ala Leu Glu Thr
305                 310                 315                 320

Gly His Gly Arg Gln Cys Gln Asn Gly Thr Val Cys Lys Pro Gly Trp
                325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
        355                 360                 365

Leu Tyr Trp Val Asn Asp Ala Val Gly Arg Asp Trp Pro Trp Ile Tyr
```

-continued

```
            370                 375                 380
Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
            435                 440                 445

Pro Glu Asn Glu Asp Glu Gly Met Asp Glu Glu Lys Pro Arg Asn Met
450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
                485                 490                 495

Ile Ser Lys Ser Lys Phe Ser Arg Tyr Trp Arg Arg Trp Asn Arg Phe
                500                 505                 510

Cys Arg Arg Lys Cys Arg Ala Ala Val Lys Ser Asn Val Phe Tyr Trp
            515                 520                 525

Leu Val Ile Phe Leu Val Phe Leu Asn Thr Leu Thr Ile Ala Ser Glu
            530                 535                 540

His Tyr Asn Gln Pro Asn Trp Leu Thr Glu Val Gln Asp Thr Ala Asn
545                 550                 555                 560

Lys Ala Leu Leu Ala Leu Phe Thr Ala Glu Met Leu Leu Lys Met Tyr
                565                 570                 575

Ser Leu Gly Leu Gln Ala Tyr Phe Val Ser Leu Phe Asn Arg Phe Asp
            580                 585                 590

Cys Phe Val Val Cys Gly Gly Ile Leu Glu Thr Ile Leu Val Glu Thr
            595                 600                 605

Lys Ile Met Ser Pro Leu Gly Ile Ser Val Leu Arg Cys Val Arg Leu
            610                 615                 620

Leu Arg Ile Phe Lys Ile Thr Arg Tyr Trp Asn Ser Leu Ser Asn Leu
625                 630                 635                 640

Val Ala Ser Leu Leu Asn Ser Val Arg Ser Ile Ala Ser Leu Leu Leu
                645                 650                 655

Leu Leu Phe Leu Phe Ile Ile Ile Phe Ser Leu Leu Gly Met Gln Leu
                660                 665                 670

Phe Gly Gly Lys Phe Asn Phe Asp Glu Met Gln Thr Arg Arg Ser Thr
            675                 680                 685

Phe Asp Asn Phe Pro Gln Ser Leu Leu Thr Val Phe Gln Ile Leu Thr
690                 695                 700

Gly Glu Asp Trp Asn Ser Val Met Tyr Asp Gly Ile Met Ala Tyr Gly
705                 710                 715                 720

Gly Pro Ser Phe Pro Gly Met Leu Val Cys Ile Tyr Phe Ile Ile Leu
                725                 730                 735

Phe Ile Cys Gly Asn Tyr Ile Leu Leu Asn Val Phe Leu Ala Ile Ala
            740                 745                 750

Val Asp Asn Leu Ala Asp Ala Glu Ser Leu Thr Ser Ala Gln Lys Glu
            755                 760                 765

Glu Glu Glu Glu Lys Glu Arg Lys Lys Leu Ala Arg Thr Ala Ser Pro
            770                 775                 780

Glu Lys Lys Gln Glu Leu Val Glu Lys Pro Ala Val Gly Glu Ser Lys
785                 790                 795                 800
```

```
Glu Glu Lys Ile Glu Leu Lys Ser Ile Thr Ala Asp Gly Glu Ser Pro
            805                 810                 815

Pro Ala Thr Lys Ile Asn Met Asp Asp Leu Gln Pro Asn Glu Asn Glu
            820                 825                 830

Asp Lys Ser Pro Tyr Pro Asn Pro Glu Thr Thr Gly Glu Glu Asp Glu
            835                 840                 845

Glu Glu Pro Glu Met Pro Val Gly Pro Arg Pro Arg Pro Leu Ser Glu
            850                 855                 860

Leu His Leu Lys Glu Lys Ala Val Pro Met Pro Glu Ala Ser Ala Phe
865                 870                 875                 880

Phe Ile Phe Ser Ser Asn Asn Arg Phe Arg Leu Gln Cys His Arg Ile
            885                 890                 895

Val Asn Asp Thr Ile Phe Thr Asn Leu Ile Leu Phe Phe Ile Leu Leu
            900                 905                 910

Ser Ser Ile Ser Leu Ala Ala Glu Asp Pro Val Gln His Thr Ser Phe
            915                 920                 925

Arg Asn His Ile Leu Phe Tyr Phe Asp Ile Val Phe Thr Thr Ile Phe
            930                 935                 940

Thr Ile Glu Ile Ala Leu Lys Met Thr Ala Tyr Gly Ala Phe Leu His
945                 950                 955                 960

Lys Gly Ser Phe Cys Arg Asn Tyr Phe Asn Ile Leu Asp Leu Leu Val
            965                 970                 975

Val Ser Val Ser Leu Ile Ser Phe Gly Ile Gln Ser Ser Ala Ile Asn
            980                 985                 990

Val Val Lys Ile Leu Arg Val Leu Arg Val Leu Arg Pro Leu Arg Ala
            995                 1000                1005

Ile Asn Arg Ala Lys Gly Leu Lys His Val Val Gln Cys Val Phe
     1010                1015                1020

Val Ala Ile Arg Thr Ile Gly Asn Ile Val Ile Val Thr Thr Leu
     1025                1030                1035

Leu Gln Phe Met Phe Ala Cys Ile Gly Val Gln Leu Phe Lys Gly
     1040                1045                1050

Lys Leu Tyr Thr Cys Ser Asp Ser Ser Lys Gln Thr Glu Ala Glu
     1055                1060                1065

Cys Lys Gly Asn Tyr Ile Thr Tyr Lys Asp Gly Glu Val Asp His
     1070                1075                1080

Pro Ile Ile Gln Pro Arg Ser Trp Glu Asn Ser Lys Phe Asp Phe
     1085                1090                1095

Asp Asn Val Leu Ala Ala Met Met Ala Leu Phe Thr Val Ser Thr
     1100                1105                1110

Phe Glu Gly Trp Pro Glu Leu Leu Tyr Arg Ser Ile Asp Ser His
     1115                1120                1125

Thr Glu Asp Lys Gly Pro Ile Tyr Asn Tyr Arg Val Glu Ile Ser
     1130                1135                1140

Ile Phe Phe Ile Ile Tyr Ile Ile Ile Ala Phe Phe Met Met
     1145                1150                1155

Asn Ile Phe Val Gly Phe Val Ile Val Thr Phe Gln Glu Gln Gly
     1160                1165                1170

Glu Gln Glu Tyr Lys Asn Cys Glu Leu Asp Lys Asn Gln Arg Gln
     1175                1180                1185

Cys Val Glu Tyr Ala Leu Lys Ala Arg Pro Leu Arg Arg Tyr Ile
     1190                1195                1200
```

-continued

| | | | | | | | | | | | |
|---|---|---|---|---|---|---|---|---|---|---|---|
| Pro | Lys 1205 | Asn | His | Gln 1210 | Tyr | Lys | Val | Trp 1215 | Tyr | Val | Asn Ser |
| Thr | Tyr 1220 | Phe | Glu | Tyr 1225 | Leu | Met | Phe | Val 1230 | Leu | Ile | Leu Leu | Asn Thr |
| Ile | Cys 1235 | Leu | Ala | Met 1240 | Gln | His | Tyr | Gly 1245 | Gln | Ser | Cys Leu Phe Lys |
| Ile | Ala 1250 | Met | Asn | Ile 1255 | Leu | Asn | Met | Leu 1260 | Phe | Thr | Gly Leu Phe Thr |
| Val | Glu 1265 | Met | Ile | Leu 1270 | Lys | Leu | Ile | Ala 1275 | Phe | Lys | Pro Lys His Tyr |
| Phe | Cys 1280 | Asp | Ala | Trp 1285 | Asn | Thr | Phe | Asp 1290 | Ala | Leu | Ile Val Val Gly |
| Ser | Ile 1295 | Val | Asp | Ile 1300 | Ala | Ile | Thr | Glu 1305 | Val | Asn | Pro Ala Glu His |
| Thr | Gln 1310 | Cys | Ser | Pro 1315 | Ser | Met | Gly | Pro 1320 | Ser | Cys | Ser His Pro Pro |
| Leu | Ala 1325 | Val | Leu | Thr 1330 | Ala | Pro | Pro | Val 1335 | Ala | Asp | Gly Phe Gln Asn |
| Ala | Glu 1340 | Glu | Asn | Ser 1345 | Arg | Ile | Ser | Ile 1350 | Thr | Phe | Phe Arg Leu Phe |
| Arg | Val 1355 | Met | Arg | Leu 1360 | Val | Lys | Leu | Leu 1365 | Ser | Arg | Gly Glu Gly Ile |
| Arg | Thr 1370 | Leu | Leu | Trp 1375 | Thr | Phe | Ile | Lys 1380 | Ser | Phe | Gln Ala Leu Pro |
| Tyr | Val 1385 | Ala | Leu | Leu 1390 | Ile | Val | Met | Leu 1395 | Phe | Phe | Ile Tyr Ala Val |
| Ile | Gly 1400 | Met | Gln | Val 1405 | Phe | Gly | Lys | Ile 1410 | Ala | Leu | Asn Asp Thr Thr |
| Glu | Ile 1415 | Asn | Arg | Asn 1420 | Asn | Asn | Phe | Gln 1425 | Thr | Phe | Pro Gln Ala Val |
| Leu | Leu 1430 | Leu | Phe | Arg 1435 | Cys | Ala | Thr | Gly 1440 | Glu | Ala | Trp Gln Asp Ile |
| Met | Leu 1445 | Ala | Cys | Met 1450 | Pro | Gly | Lys | Lys 1455 | Cys | Ala | Pro Glu Ser Glu |
| Pro | Ser 1460 | Asn | Ser | Thr 1465 | Glu | Gly | Glu | Thr 1470 | Pro | Cys | Gly Ser Ser Phe |
| Ala | Val 1475 | Phe | Tyr | Phe 1480 | Ile | Ser | Phe | Tyr 1485 | Met | Leu | Cys Ala Phe Leu |
| Ile | Ile 1490 | Asn | Leu | Phe 1495 | Val | Ala | Val | Ile 1500 | Met | Asp | Asn Phe Asp Tyr |
| Leu | Thr 1505 | Arg | Asp | Trp 1510 | Ser | Ile | Leu | Gly 1515 | Pro | His | His Leu Asp Glu |
| Phe | Lys 1520 | Arg | Ile | Trp 1525 | Ala | Glu | Tyr | Asp 1530 | Pro | Glu | Ala Lys Gly Arg |
| Ile | Lys 1535 | His | Leu | Asp 1540 | Val | Val | Thr | Leu 1545 | Leu | Arg | Arg Ile Gln Pro |
| Pro | Leu 1550 | Gly | Phe | Gly 1555 | Lys | Leu | Cys | Pro 1560 | His | Arg | Val Ala Cys Lys |
| Arg | Leu 1565 | Val | Ser | Met 1570 | Asn | Met | Pro | Leu 1575 | Asn | Ser | Asp Gly Thr Val |
| Met | Phe 1580 | Asn | Ala | Thr 1585 | Leu | Phe | Ala | Leu 1590 | Val | Arg | Thr Ala Leu Arg |
| Ile | Lys | Thr | Glu | Glu | Gly | Pro | Ser | Pro | Ser | Glu | Ala His Gln Gly |

```
                1595                1600                1605

Ala Glu Asp Pro Phe Arg Pro Ala Gly Asn Leu Glu Gln Ala Asn
    1610                1615                1620

Glu Glu Leu Arg Ala Ile Ile Lys Lys Ile Trp Lys Arg Thr Ser
1625                1630                1635

Met Lys Leu Leu Asp Gln Val Val Pro Ala Gly Asp Asp Glu
    1640                1645                1650

Val Thr Val Gly Lys Phe Tyr Ala Thr Phe Leu Ile Gln Glu Tyr
1655                1660                1665

Phe Arg Lys Phe Lys Lys Arg Lys Glu Gln Gly Leu Val Gly Lys
    1670                1675                1680

Pro Ser Gln Arg Asn Ala Leu Ser Leu Gln Ala Gly Leu Arg Thr
    1685                1690                1695

Leu His Asp Ile Gly Pro Glu Ile Arg Arg Ala Ile Ser Gly Asp
    1700                1705                1710

Leu Thr Ala Glu Glu Glu Leu Asp Lys Ala Met Lys Glu Ala Val
    1715                1720                1725

Ser Ala Ala Ser Glu Asp Asp Ile Phe Arg Arg Ala Gly Gly Leu
1730                1735                1740

Phe Gly Asn His Val Ser Tyr Tyr Gln Ser Asp Gly Arg Ser Ala
    1745                1750                1755

Phe Pro Gln Thr Phe Thr Thr Gln Arg Pro Leu His Ile Asn Lys
    1760                1765                1770

Ala Gly Ser Ser Gln Gly Asp Thr Glu Ser Pro Ser His Glu Lys
    1775                1780                1785

Leu Val Asp Ser Thr Phe Thr Pro Ser Ser Tyr Ser Ser Thr Gly
    1790                1795                1800

Ser Asn Ala Asn Ile Asn Asn Ala Asn Asn Thr Ala Leu Gly Arg
    1805                1810                1815

Leu Pro Arg Pro Ala Gly Tyr Pro Ser Thr Val Ser Thr Val Glu
    1820                1825                1830

Gly His Gly Pro Pro Leu Ser Pro Ala Ile Arg Val Gln Glu Val
    1835                1840                1845

Ala Trp Lys Leu Ser Ser Asn Arg Cys His Ser Arg Glu Ser Gln
    1850                1855                1860

Ala Ala Met Ala Gly Gln Glu Glu Thr Ser Gln Asp Glu Thr Tyr
    1865                1870                1875

Glu Val Lys Met Asn His Asp Thr Glu Ala Cys Ser Glu Pro Ser
    1880                1885                1890

Leu Leu Ser Thr Glu Met Leu Ser Tyr Gln Asp Asp Glu Asn Arg
    1895                1900                1905

Gln Leu Thr Leu Pro Glu Glu Asp Lys Arg Asp Ile Arg Gln Ser
    1910                1915                1920

Pro Lys Arg Gly Phe Leu Arg Ser Ala Ser Leu Gly Arg Arg Ala
    1925                1930                1935

Xaa Phe His Leu Glu Cys Leu Lys Arg Gln Lys Asp Arg Gly Gly
    1940                1945                1950

Asp Ile Ser Gln Lys Thr Val Leu Pro Leu His Leu Val His His
    1955                1960                1965

Gln Ala Leu Ala Val Ala Gly Leu Ser Pro Leu Leu Gln Arg Ser
    1970                1975                1980

His Ser Pro Ala Ser Phe Pro Arg Pro Phe Ala Thr Pro Pro Ala
    1985                1990                1995
```

```
Thr Pro Gly Ser Arg Gly Trp Pro Pro Gln Pro Val Pro Thr Leu
    2000            2005            2010

Arg Leu Glu Gly Val Glu Ser Ser Glu Lys Leu Asn Ser Ser Phe
    2015            2020            2025

Pro Ser Ile His Cys Gly Ser Trp Ala Glu Thr Thr Pro Gly Gly
    2030            2035            2040

Gly Gly Ser Ser Ala Ala Arg Arg Val Arg Pro Val Ser Leu Met
    2045            2050            2055

Val Pro Ser Gln Ala Gly Ala Pro Gly Arg Gln Phe His Gly Ser
    2060            2065            2070

Ala Ser Ser Leu Val Glu Ala Val Leu Ile Ser Glu Gly Leu Gly
    2075            2080            2085

Gln Phe Ala Gln Asp Pro Lys Phe Ile Glu Val Thr Thr Gln Glu
    2090            2095            2100

Leu Ala Asp Ala Cys Asp Met Thr Ile Glu Glu Met Glu Ser Ala
    2105            2110            2115

Ala Asp Asn Ile Leu Ser Gly Gly Ala Pro Gln Ser Pro Asn Gly
    2120            2125            2130

Ala Leu Leu Pro Phe Val Asn Cys Arg Asp Ala Gly Gln Asp Arg
    2135            2140            2145

Ala Gly Gly Glu Glu Asp Ala Gly Cys Val Arg Ala Arg Gly Ala
    2150            2155            2160

Pro Ser Glu Glu Glu Leu Gln Asp Ser Arg Val Tyr Val Ser Ser
    2165            2170            2175

Leu

<210> SEQ ID NO 26
<211> LENGTH: 1113
<212> TYPE: PRT
<213> ORGANISM: human
<220> FEATURE:
<221> NAME/KEY: misc_feature
<222> LOCATION: (975)..(975)
<223> OTHER INFORMATION: Xaa can be any naturally occurring amino acid
<220> FEATURE:
<221> NAME/KEY: misc_feature
<222> LOCATION: (978)..(978)
<223> OTHER INFORMATION: Xaa can be any naturally occurring amino acid

<400> SEQUENCE: 26

Met Pro Arg Pro Glu Leu Pro Leu Pro Glu Gly Trp Glu Glu Ala Arg
1               5                   10                  15

Asp Phe Asp Gly Lys Val Tyr Tyr Ile Asp His Thr Asn Arg Thr Thr
                20                  25                  30

Ser Trp Ile Asp Pro Arg Asp Arg Tyr Thr Lys Pro Leu Thr Phe Ala
            35                  40                  45

Asp Cys Ile Ser Asp Glu Leu Pro Leu Gly Trp Glu Glu Ala Tyr Asp
        50                  55                  60

Pro Gln Val Gly Asp Tyr Phe Ile Asp His Asn Thr Lys Thr Thr Gln
65                  70                  75                  80

Ile Glu Asp Pro Arg Val Gln Trp Arg Arg Glu Gln Glu His Met Leu
                85                  90                  95

Lys Asp Tyr Leu Val Val Ala Gln Glu Ala Leu Ser Ala Gln Lys Glu
                100                 105                 110

Ile Tyr Gln Val Lys Gln Gln Arg Leu Glu Leu Ala Gln Gln Glu Tyr
            115                 120                 125
```

-continued

```
Gln Gln Leu His Ala Val Trp Glu His Lys Leu Gly Ser Gln Val Ser
    130                 135                 140

Leu Val Ser Gly Ser Ser Ser Ser Lys Tyr Asp Pro Glu Ile Leu
145                 150                 155                 160

Lys Ala Glu Ile Ala Thr Ala Lys Ser Arg Val Asn Lys Leu Lys Arg
                165                 170                 175

Glu Met Val His Leu Gln His Glu Leu Gln Phe Lys Glu Arg Gly Phe
            180                 185                 190

Gln Thr Leu Lys Lys Ile Asp Lys Lys Met Ser Asp Ala Gln Gly Ser
        195                 200                 205

Tyr Lys Leu Asp Glu Ala Gln Ala Val Leu Arg Glu Thr Lys Ala Ile
    210                 215                 220

Lys Lys Ala Ile Thr Cys Gly Glu Lys Glu Lys Gln Asp Leu Ile Lys
225                 230                 235                 240

Ser Leu Ala Met Leu Lys Asp Gly Phe Arg Thr Asp Arg Gly Ser His
                245                 250                 255

Ser Asp Leu Trp Ser Ser Ser Ser Leu Glu Ser Ser Phe Pro
            260                 265                 270

Leu Pro Lys Gln Tyr Leu Asp Val Ser Ser Gln Thr Asp Ile Ser Gly
        275                 280                 285

Ser Phe Gly Ile Asn Ser Asn Asn Gln Leu Ala Glu Lys Val Arg Leu
    290                 295                 300

Arg Leu Arg Tyr Glu Glu Ala Lys Arg Arg Ile Ala Asn Leu Lys Ile
305                 310                 315                 320

Gln Leu Ala Lys Leu Asp Ser Glu Ala Trp Pro Gly Val Leu Asp Ser
                325                 330                 335

Glu Arg Asp Arg Leu Ile Leu Ile Asn Glu Lys Glu Leu Leu Lys
            340                 345                 350

Glu Met Arg Phe Ile Ser Pro Arg Lys Trp Thr Gln Gly Glu Val Glu
        355                 360                 365

Gln Leu Glu Met Ala Arg Lys Arg Leu Gly Lys Asp Leu Gln Ala Ala
    370                 375                 380

Arg Asp Thr Gln Ser Lys Ala Leu Thr Glu Arg Leu Lys Leu Asn Ser
385                 390                 395                 400

Lys Arg Asn Gln Leu Val Arg Glu Leu Glu Glu Ala Thr Arg Gln Val
                405                 410                 415

Ala Thr Leu His Ser Gln Leu Lys Ser Leu Ser Ser Met Gln Ser
            420                 425                 430

Leu Ser Ser Gly Ser Ser Pro Gly Ser Leu Thr Ser Ser Arg Gly Ser
        435                 440                 445

Leu Val Ala Ser Ser Leu Asp Ser Ser Thr Ser Ala Ser Phe Thr Asp
    450                 455                 460

Leu Tyr Tyr Asp Pro Phe Glu Gln Leu Asp Ser Glu Leu Gln Ser Lys
465                 470                 475                 480

Val Glu Phe Leu Leu Leu Glu Gly Ala Thr Gly Phe Arg Pro Ser Gly
                485                 490                 495

Cys Ile Thr Thr Ile His Glu Asp Glu Val Ala Lys Thr Gln Lys Ala
            500                 505                 510

Glu Gly Gly Gly Arg Leu Gln Ala Leu Arg Ser Leu Ser Gly Thr Pro
        515                 520                 525

Lys Ser Met Thr Ser Leu Ser Pro Arg Ser Ser Leu Ser Ser Pro Ser
    530                 535                 540

Pro Pro Cys Ser Pro Leu Met Ala Asp Pro Leu Leu Ala Gly Asp Ala
```

-continued

```
            545                 550                 555                 560
        Phe Leu Asn Ser Leu Glu Phe Glu Asp Pro Glu Leu Ser Ala Thr Leu
                        565                 570                 575
        Cys Glu Leu Ser Leu Gly Asn Ser Ala Gln Glu Arg Tyr Arg Leu Glu
                        580                 585                 590
        Glu Pro Gly Thr Glu Gly Lys Gln Leu Gly Gln Ala Val Asn Thr Ala
                        595                 600                 605
        Gln Gly Cys Gly Leu Lys Val Ala Cys Val Ser Ala Ala Val Ser Asp
                        610                 615                 620
        Glu Ser Val Ala Gly Asp Ser Gly Val Tyr Glu Ala Ser Val Gln Arg
        625                 630                 635                 640
        Leu Gly Ala Ser Glu Ala Ala Ala Phe Asp Ser Asp Glu Ser Glu Ala
                        645                 650                 655
        Val Gly Ala Thr Arg Ile Gln Ile Ala Leu Lys Tyr Asp Glu Lys Asn
                        660                 665                 670
        Lys Gln Phe Ala Ile Leu Ile Ile Gln Leu Ser Asn Leu Ser Ala Leu
                        675                 680                 685
        Leu Gln Gln Gln Asp Gln Lys Val Asn Ile Arg Val Ala Val Leu Pro
                        690                 695                 700
        Cys Ser Glu Ser Thr Thr Cys Leu Phe Arg Thr Arg Pro Leu Asp Ala
        705                 710                 715                 720
        Ser Asp Thr Leu Val Phe Asn Glu Val Phe Trp Val Ser Met Ser Tyr
                        725                 730                 735
        Pro Ala Leu His Gln Lys Thr Leu Arg Val Asp Val Cys Thr Thr Asp
                        740                 745                 750
        Arg Ser His Leu Glu Glu Cys Leu Gly Gly Ala Gln Ile Ser Leu Ala
                        755                 760                 765
        Glu Val Cys Arg Ser Gly Glu Arg Ser Thr Arg Trp Tyr Asn Leu Leu
                        770                 775                 780
        Ser Tyr Lys Tyr Leu Lys Lys Gln Ser Arg Glu Leu Lys Pro Val Gly
        785                 790                 795                 800
        Val Met Ala Pro Ala Ser Gly Pro Ala Ser Thr Asp Ala Val Ser Ala
                        805                 810                 815
        Leu Leu Glu Gln Thr Ala Val Glu Leu Glu Lys Arg Gln Glu Gly Arg
                        820                 825                 830
        Ser Ser Thr Gln Thr Leu Glu Asp Ser Trp Arg Tyr Glu Glu Thr Ser
                        835                 840                 845
        Glu Asn Glu Ala Val Ala Glu Glu Glu Glu Glu Val Glu Glu Glu
                        850                 855                 860
        Glu Gly Glu Glu Asp Val Phe Thr Glu Lys Ala Ser Pro Asp Met Asp
        865                 870                 875                 880
        Gly Tyr Pro Ala Leu Lys Val Asp Lys Glu Thr Asn Thr Glu Thr Pro
                        885                 890                 895
        Ala Pro Ser Pro Thr Val Val Arg Pro Lys Asp Arg Val Gly Thr
                        900                 905                 910
        Pro Ser Gln Gly Pro Phe Leu Arg Gly Ser Thr Ile Ile Arg Ser Lys
                        915                 920                 925
        Thr Phe Ser Pro Gly Pro Gln Ser Gln Tyr Val Cys Arg Leu Asn Arg
                        930                 935                 940
        Ser Asp Ser Asp Ser Ser Thr Leu Ser Lys Lys Pro Pro Phe Val Arg
        945                 950                 955                 960
        Asn Ser Leu Glu Arg Arg Ser Val Arg Met Lys Arg Pro Ser Xaa Val
                        965                 970                 975
```

```
Lys Xaa Leu Arg Ser Glu Arg Leu Ile Arg Thr Ser Leu Asp Leu Glu
        980                 985                 990

Leu Asp Leu Gln Ala Thr Arg Thr Trp His Ser Gln Leu Thr Gln Glu
        995                1000                1005

Ile Ser Val Leu Lys Glu Leu Lys Glu Gln Leu Glu Gln Ala Lys
   1010                1015                1020

Ser His Gly Glu Lys Glu Leu Pro Gln Trp Leu Arg Glu Asp Glu
   1025                1030                1035

Arg Phe Arg Leu Leu Leu Arg Met Leu Glu Lys Arg Gln Met Asp
   1040                1045                1050

Arg Ala Glu His Lys Gly Glu Leu Gln Thr Asp Lys Met Met Arg
   1055                1060                1065

Ala Ala Ala Lys Asp Val His Arg Leu Arg Gly Gln Ser Cys Lys
   1070                1075                1080

Glu Pro Pro Glu Val Gln Ser Phe Arg Glu Lys Met Ala Phe Phe
   1085                1090                1095

Thr Arg Pro Arg Met Asn Ile Pro Ala Leu Ser Ala Asp Asp Val
   1100                1105                1110

<210> SEQ ID NO 27
<211> LENGTH: 1235
<212> TYPE: PRT
<213> ORGANISM: rat
<220> FEATURE:
<221> NAME/KEY: misc_feature
<222> LOCATION: (498)..(498)
<223> OTHER INFORMATION: Xaa can be any naturally occurring amino acid
<220> FEATURE:
<221> NAME/KEY: misc_feature
<222> LOCATION: (570)..(570)
<223> OTHER INFORMATION: Xaa can be any naturally occurring amino acid
<220> FEATURE:
<221> NAME/KEY: misc_feature
<222> LOCATION: (612)..(612)
<223> OTHER INFORMATION: Xaa can be any naturally occurring amino acid

<400> SEQUENCE: 27

Met Ala Ser Pro Pro Asp Thr Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Ala His His Asp Gly Ala Gly Gly Gly Cys
        115                 120                 125

Gly Gly Ser Cys Ser Gly Ser Ser Gly Val Gly Glu Ala Gly Glu Asp
    130                 135                 140

Leu Ser Tyr Asp Thr Gly Pro Gly Pro Ala Phe Lys Glu Val Trp Gln
145                 150                 155                 160

Val Ile Leu Lys Pro Lys Gly Leu Gly Gln Thr Lys Asn Leu Ile Gly
```

```
                    165                 170                 175
Ile Tyr Arg Leu Cys Leu Thr Ser Lys Thr Ile Ser Phe Val Lys Leu
                180                 185                 190

Asn Ser Glu Ala Ala Val Val Leu Gln Leu Met Asn Ile Arg Arg
            195                 200                 205

Cys Gly His Ser Glu Asn Phe Phe Ile Glu Val Gly Arg Ser Ala
        210                 215                 220

Val Thr Gly Pro Gly Glu Phe Trp Met Gln Val Asp Asp Ser Val Val
225                 230                 235                 240

Ala Gln Asn Met His Glu Thr Ile Leu Glu Ala Met Arg Ala Met Ser
                245                 250                 255

Asp Glu Phe Arg Pro Arg Thr Lys Ser Gln Ser Ser Ser Cys Ser
            260                 265                 270

Asn Pro Ile Ser Val Pro Leu Arg Arg His His Leu Asn Asn Pro Pro
        275                 280                 285

Pro Ser Gln Val Gly Leu Thr Arg Arg Ser Arg Thr Glu Ser Ile Thr
    290                 295                 300

Ala Thr Ser Pro Ala Ser Met Val Gly Gly Lys Pro Gly Ser Phe Arg
305                 310                 315                 320

Val Arg Ala Ser Ser Asp Gly Glu Gly Thr Met Ser Arg Pro Ala Ser
                325                 330                 335

Val Asp Gly Ser Pro Val Ser Pro Ser Thr Asn Arg Thr His Ala His
            340                 345                 350

Arg His Arg Gly Ser Ser Arg Leu His Pro Pro Leu Asn His Ser Arg
        355                 360                 365

Ser Ile Pro Met Pro Ser Ser Arg Cys Ser Pro Ser Ala Thr Ser Pro
    370                 375                 380

Val Ser Leu Ser Ser Ser Ser Thr Ser Gly His Gly Ser Thr Ser Asp
385                 390                 395                 400

Cys Leu Phe Pro Arg Arg Ser Ser Ala Ser Val Ser Gly Ser Pro Ser
                405                 410                 415

Asp Gly Gly Phe Ile Ser Ser Asp Glu Tyr Gly Ser Ser Pro Cys Asp
            420                 425                 430

Phe Arg Ser Ser Phe Arg Ser Val Thr Pro Asp Ser Leu Gly His Thr
        435                 440                 445

Pro Pro Ala Arg Gly Glu Glu Leu Ser Asn Tyr Ile Cys Met Gly
    450                 455                 460

Gly Lys Gly Ala Ser Thr Leu Thr Ala Pro Asn Gly His Tyr Ile Leu
465                 470                 475                 480

Ser Arg Gly Gly Asn Gly His Arg Tyr Ile Pro Gly Ala Thr Met Gly
                485                 490                 495

Thr Xaa Pro Ala Leu Thr Gly Asp Glu Ala Ala Gly Ala Ala Asp Leu
            500                 505                 510

Asp Asn Arg Phe Arg Lys Arg Thr His Ser Ala Gly Thr Ser Pro Thr
        515                 520                 525

Ile Ser His Gln Lys Thr Pro Ser Gln Ser Ser Val Val Ser Ile Glu
    530                 535                 540

Glu Tyr Thr Glu Met Met Pro Ala Ala Tyr Pro Pro Gly Gly Gly Ser
545                 550                 555                 560

Gly Gly Arg Leu Pro Gly Tyr Arg His Xaa Ala Phe Val Pro Thr His
                565                 570                 575

Ser Tyr Pro Glu Glu Gly Leu Glu Met His His Leu Glu Arg Arg Gly
            580                 585                 590
```

```
Gly His His Arg Pro Asp Ser Ser Asn Leu His Thr Asp Asp Gly Tyr
        595                 600                 605

Met Pro Met Xaa Pro Gly Val Ala Pro Val Pro Ser Asn Arg Lys Gly
        610                 615                 620

Asn Gly Asp Tyr Met Pro Met Ser Pro Lys Ser Val Ser Ala Pro Gln
625                 630                 635                 640

Gln Ile Ile Asn Pro Ile Arg Arg His Pro Gln Arg Val Asp Pro Asn
                645                 650                 655

Gly Tyr Met Met Met Ser Pro Ser Gly Ser Cys Ser Pro Asp Ile Gly
            660                 665                 670

Gly Gly Ser Cys Ser Ser Ser Ile Ser Ala Ala Pro Ser Gly Ser
        675                 680                 685

Ser Tyr Gly Lys Pro Trp Thr Asn Gly Val Gly Gly His His Thr His
        690                 695                 700

Ala Leu Pro His Ala Lys Pro Pro Val Glu Ser Gly Gly Lys Leu
705                 710                 715                 720

Leu Pro Cys Thr Gly Asp Tyr Met Asn Met Ser Pro Val Gly Asp Ser
                725                 730                 735

Asn Thr Ser Ser Pro Ser Glu Cys Tyr Tyr Gly Pro Glu Asp Pro Gln
            740                 745                 750

His Lys Pro Val Leu Ser Tyr Tyr Ser Leu Pro Arg Ser Phe Lys His
        755                 760                 765

Thr Gln Arg Pro Gly Glu Pro Glu Glu Gly Ala Arg His Gln His Leu
        770                 775                 780

Arg Leu Ser Ser Ser Ser Gly Arg Leu Arg Tyr Thr Ala Thr Ala Glu
785                 790                 795                 800

Asp Ser Ser Ser Ser Thr Ser Ser Asp Ser Leu Gly Gly Gly Tyr Cys
                805                 810                 815

Gly Ala Arg Pro Glu Ser Ser Val Thr His Pro His His His Ala Leu
            820                 825                 830

Gln Pro His Leu Pro Arg Lys Val Asp Thr Ala Ala Gln Thr Asn Ser
        835                 840                 845

Arg Leu Ala Arg Pro Thr Arg Leu Ser Leu Gly Asp Pro Lys Ala Ser
850                 855                 860

Thr Leu Pro Arg Val Arg Glu Gln Gln Gln Gln Gln Gln Gln Gln Gln
865                 870                 875                 880

Gln Ser Ser Leu His Pro Pro Glu Pro Lys Ser Pro Gly Glu Tyr Val
                885                 890                 895

Asn Ile Glu Phe Gly Ser Gly Gln Pro Gly Tyr Leu Ala Gly Pro Ala
            900                 905                 910

Thr Ser Arg Ser Ser Pro Ser Val Arg Cys Leu Pro Gln Leu His Pro
        915                 920                 925

Ala Pro Arg Glu Glu Thr Gly Ser Glu Glu Tyr Met Asn Met Asp Leu
930                 935                 940

Gly Pro Gly Arg Arg Ala Thr Trp Gln Glu Ser Gly Gly Val Glu Leu
945                 950                 955                 960

Gly Arg Val Gly Pro Ala Pro Pro Gly Ala Ala Ser Ile Cys Arg Pro
                965                 970                 975

Thr Arg Ser Val Pro Asn Ser Arg Gly Asp Tyr Met Thr Met Gln Ile
            980                 985                 990

Gly Cys Pro Arg Gln Ser Tyr Val Asp Thr Ser Pro Val Ala Pro Val
        995                 1000                1005
```

```
Ser Tyr Ala Asp Met Arg Thr Gly Ile Ala Ala Glu Lys Val Ser
    1010                1015                1020

Leu Pro Arg Thr Thr Gly Ala Ala Pro Pro Ser Ser Thr Ala
    1025                1030            1035

Ser Ala Ser Ala Ser Val Thr Pro Gln Gly Ala Ala Glu Gln Ala
    1040                1045                1050

Ala His Ser Ser Leu Leu Gly Gly Pro Gln Gly Pro Gly Gly Met
    1055                1060                1065

Ser Ala Phe Thr Arg Val Asn Leu Ser Pro Asn His Asn Gln Ser
    1070                1075                1080

Ala Lys Val Ile Arg Ala Asp Thr Gln Gly Cys Arg Arg Arg His
    1085                1090                1095

Ser Ser Glu Thr Phe Ser Ala Pro Thr Arg Ala Ala Asn Thr Val
    1100                1105                1110

Ser Phe Gly Ala Gly Ala Ala Gly Gly Gly Ser Gly Gly Gly Ser
    1115                1120                1125

Glu Asp Val Lys Arg His Ser Ser Ala Ser Phe Glu Asn Val Trp
    1130                1135                1140

Leu Arg Pro Gly Asp Leu Gly Gly Ala Ser Lys Glu Ser Ala Pro
    1145                1150                1155

Gly Cys Gly Ala Ala Gly Gly Leu Glu Lys Ser Leu Asn Tyr Ile
    1160                1165                1170

Asp Leu Asp Leu Val Lys Asp Val Lys Gln His Pro Gln Asp Cys
    1175                1180                1185

Pro Ser Gln Gln Gln Ser Leu Pro Pro Pro Pro His Gln Pro
    1190                1195                1200

Leu Gly Ser Asn Glu Gly Ser Ser Pro Arg Arg Ser Ser Glu Asp
    1205                1210                1215

Leu Ser Thr Tyr Ala Ser Ile Asn Phe Gln Lys Gln Pro Glu Asp
    1220                1225                1230

Arg Gln
    1235

<210> SEQ ID NO 28
<211> LENGTH: 357
<212> TYPE: PRT
<213> ORGANISM: rat
<220> FEATURE:
<221> NAME/KEY: misc_feature
<222> LOCATION: (318)..(318)
<223> OTHER INFORMATION: Xaa can be any naturally occurring amino acid

<400> SEQUENCE: 28

Met Ala Glu Leu Gln Glu Val Gln Ile Thr Glu Glu Lys Pro Leu Leu
1               5                   10                  15

Pro Gly Gln Thr Pro Glu Ala Ala Lys Thr His Ser Val Glu Thr Pro
                20                  25                  30

Tyr Gly Ser Val Thr Phe Thr Val Tyr Gly Thr Pro Lys Pro Lys Arg
            35                  40                  45

Pro Ala Ile Phe Thr Tyr His Asp Val Gly Leu Asn Tyr Lys Ser Cys
        50                  55                  60

Phe Gln Pro Leu Phe Gln Phe Gly Asp Met Gln Glu Ile Ile Gln Asn
65                  70                  75                  80

Phe Val Arg Val His Val Asp Ala Pro Gly Met Glu Glu Gly Ala Pro
                85                  90                  95

Val Phe Pro Leu Gly Tyr Gln Tyr Pro Ser Leu Asp Gln Leu Ala Asp
```

```
                 100                 105                 110
Met Ile Pro Cys Ile Leu Gln Tyr Leu Asn Phe Ser Thr Ile Ile Gly
            115                 120                 125

Val Gly Val Gly Ala Gly Ala Tyr Ile Leu Ser Arg Tyr Ala Leu Asn
        130                 135                 140

His Pro Asp Thr Val Glu Gly Leu Val Leu Ile Asn Ile Asp Pro Asn
145                 150                 155                 160

Ala Lys Gly Trp Met Asp Trp Ala Ala His Lys Leu Thr Gly Leu Thr
                165                 170                 175

Ser Ser Ile Pro Glu Met Ile Leu Gly His Leu Phe Ser Gln Glu Glu
            180                 185                 190

Leu Ser Gly Asn Ser Glu Leu Ile Gln Lys Tyr Arg Ser Leu Ile Thr
        195                 200                 205

His Ala Pro Asn Leu Glu Asn Ile Glu Leu Tyr Trp Asn Ser Tyr Asn
    210                 215                 220

Asn Arg Arg Asp Leu Asn Phe Glu Arg Gly Gly Glu Met Thr Leu Lys
225                 230                 235                 240

Cys Pro Val Met Leu Val Val Gly Asp Gln Ala Pro His Glu Asp Ala
                245                 250                 255

Val Val Glu Cys Asn Ser Lys Leu Asp Pro Thr Gln Thr Ser Phe Leu
            260                 265                 270

Lys Met Ala Asp Ser Gly Gly Gln Pro Gln Leu Thr Gln Pro Gly Lys
        275                 280                 285

Leu Thr Glu Ala Phe Lys Tyr Phe Val Gln Gly Met Gly Tyr Met Ala
    290                 295                 300

Ser Ser Cys Met Thr Arg Leu Ser Arg Ser Arg Thr Ala Xaa Leu Thr
305                 310                 315                 320

Ser Ala Ala Ser Ile Asp Gly Ser Arg Ser Arg Ser Arg Thr Leu Ser
                325                 330                 335

Gln Ser Ser Glu Ser Gly Thr Leu Pro Ser Gly Pro Pro Gly His Thr
            340                 345                 350

Met Glu Val Ser Cys
        355

<210> SEQ ID NO 29
<211> LENGTH: 399
<212> TYPE: PRT
<213> ORGANISM: human
<220> FEATURE:
<221> NAME/KEY: misc_feature
<222> LOCATION: (285)..(285)
<223> OTHER INFORMATION: Xaa can be any naturally occurring amino acid

<400> SEQUENCE: 29

Met Gly Ala Ser Phe Trp Pro Ile Arg Gln Ala Arg Glu Gln Gln Arg
1               5                   10                  15

Arg Ala Leu Ser Phe Arg Gln Thr Ser Trp Leu Ser Glu Pro Pro Leu
            20                  25                  30

Gly Pro Ala Pro His Leu Ser Met Val Gln Ala His Gly Gly Arg Ser
        35                  40                  45

Arg Ala Gln Pro Leu Thr Leu Ser Leu Gly Ala Ala Met Thr Gln Pro
    50                  55                  60

Pro Pro Glu Lys Thr Pro Ala Lys Lys His Val Arg Leu Gln Glu Arg
65                  70                  75                  80

Arg Gly Ser Asn Val Ala Leu Met Leu Asp Val Arg Ser Leu Gly Ala
                85                  90                  95
```

-continued

Val Glu Pro Ile Cys Ser Val Asn Thr Pro Arg Glu Val Thr Leu His
                100                 105                 110

Phe Leu Arg Thr Ala Gly His Pro Leu Thr Arg Trp Ala Leu Gln Arg
            115                 120                 125

Gln Pro Pro Ser Pro Lys Gln Leu Glu Glu Phe Leu Lys Ile Pro
130                 135                 140

Ser Asn Phe Val Ser Pro Glu Asp Leu Asp Ile Pro Gly His Ala Ser
145                 150                 155                 160

Lys Asp Arg Tyr Lys Thr Ile Leu Pro Asn Pro Gln Ser Arg Val Cys
                165                 170                 175

Leu Gly Arg Ala Gln Ser Gln Glu Asp Gly Asp Tyr Ile Asn Ala Asn
            180                 185                 190

Tyr Ile Arg Gly Tyr Asp Gly Lys Glu Lys Val Tyr Ile Ala Thr Gln
        195                 200                 205

Gly Pro Met Pro Asn Thr Val Ser Asp Phe Trp Glu Met Val Trp Gln
210                 215                 220

Glu Glu Val Ser Leu Ile Val Met Leu Thr Gln Leu Arg Glu Gly Lys
225                 230                 235                 240

Glu Lys Cys Val His Tyr Trp Pro Thr Glu Glu Thr Tyr Gly Pro
                245                 250                 255

Phe Gln Ile Arg Ile Gln Asp Met Lys Glu Cys Pro Glu Tyr Thr Val
            260                 265                 270

Arg Gln Leu Thr Ile Gln Tyr Gln Glu Glu Arg Arg Xaa Val Lys His
        275                 280                 285

Ile Leu Phe Ser Ala Trp Pro Asp His Gln Thr Pro Glu Ser Ala Gly
290                 295                 300

Pro Leu Leu Arg Leu Val Ala Glu Val Glu Glu Ser Pro Glu Thr Ala
305                 310                 315                 320

Ala His Pro Gly Pro Ile Val Val His Cys Ser Ala Gly Ile Gly Arg
                325                 330                 335

Thr Gly Cys Phe Ile Ala Thr Arg Ile Gly Cys Gln Gln Leu Lys Ala
            340                 345                 350

Arg Gly Glu Val Asp Ile Leu Gly Ile Val Cys Gln Leu Arg Leu Asp
        355                 360                 365

Arg Gly Gly Met Ile Gln Thr Ala Glu Gln Tyr Gln Phe Leu His His
370                 375                 380

Thr Leu Ala Leu Tyr Ala Gly Gln Leu Pro Glu Glu Pro Ser Pro
385                 390                 395

<210> SEQ ID NO 30
<211> LENGTH: 547
<212> TYPE: PRT
<213> ORGANISM: human
<220> FEATURE:
<221> NAME/KEY: misc_feature
<222> LOCATION: (311)..(311)
<223> OTHER INFORMATION: Xaa can be any naturally occurring amino acid

<400> SEQUENCE: 30

Met Ala Glu Pro Ser Gly Ser Pro Val His Val Gln Leu Pro Gln Gln
1               5                   10                  15

Ala Ala Pro Val Thr Ala Ala Ala Ala Pro Ala Ala Thr
            20                  25                  30

Ala Ala Pro Ala Pro Ala Ala Pro Ala Ala Pro Ala Pro Ala
        35                  40                  45

-continued

```
Pro Ala Pro Ala Ala Gln Ala Val Gly Trp Pro Ile Cys Arg Asp Ala
 50                  55                  60

Tyr Glu Leu Gln Glu Val Ile Gly Ser Gly Ala Thr Ala Val Val Gln
 65                  70                  75                  80

Ala Ala Leu Cys Lys Pro Arg Gln Glu Arg Val Ala Ile Lys Arg Ile
                 85                  90                  95

Asn Leu Glu Lys Cys Gln Thr Ser Met Asp Glu Leu Leu Lys Glu Ile
                100                 105                 110

Gln Ala Met Ser Gln Cys Ser His Pro Asn Val Val Thr Tyr Tyr Thr
            115                 120                 125

Ser Phe Val Val Lys Asp Glu Leu Trp Leu Val Met Lys Leu Leu Ser
130                 135                 140

Gly Gly Ser Met Leu Asp Ile Ile Lys Tyr Ile Val Asn Arg Gly Glu
145                 150                 155                 160

His Lys Asn Gly Val Leu Glu Glu Ala Ile Ile Ala Thr Ile Leu Lys
                165                 170                 175

Glu Val Leu Glu Gly Leu Asp Tyr Leu His Arg Asn Gly Gln Ile His
            180                 185                 190

Arg Asp Leu Lys Ala Gly Asn Ile Leu Leu Gly Glu Asp Gly Ser Val
        195                 200                 205

Gln Ile Ala Asp Phe Gly Val Ser Ala Phe Leu Ala Thr Gly Gly Asp
210                 215                 220

Val Thr Arg Asn Lys Val Arg Lys Thr Phe Val Gly Thr Pro Cys Trp
225                 230                 235                 240

Met Ala Pro Glu Val Met Glu Gln Val Arg Gly Tyr Asp Phe Lys Ala
                245                 250                 255

Asp Met Trp Ser Phe Gly Ile Thr Ala Ile Glu Leu Ala Thr Gly Ala
            260                 265                 270

Ala Pro Tyr His Lys Tyr Pro Pro Met Lys Val Leu Met Leu Thr Leu
        275                 280                 285

Gln Asn Asp Pro Pro Thr Leu Glu Thr Gly Val Glu Asp Lys Glu Met
290                 295                 300

Met Lys Lys Tyr Gly Lys Xaa Phe Arg Lys Leu Leu Ser Leu Cys Leu
305                 310                 315                 320

Gln Lys Asp Pro Ser Lys Arg Pro Thr Ala Ala Glu Leu Leu Lys Cys
                325                 330                 335

Lys Phe Phe Gln Lys Ala Lys Asn Arg Glu Tyr Leu Ile Glu Lys Leu
            340                 345                 350

Leu Thr Arg Thr Pro Asp Ile Ala Gln Arg Ala Lys Lys Val Arg Arg
        355                 360                 365

Val Pro Gly Ser Ser Gly His Leu His Lys Thr Glu Asp Gly Asp Trp
370                 375                 380

Glu Trp Ser Asp Asp Glu Met Asp Glu Lys Ser Glu Glu Gly Lys Ala
385                 390                 395                 400

Ala Phe Ser Gln Glu Lys Ser Arg Arg Val Lys Glu Glu Asn Pro Glu
                405                 410                 415

Ile Ala Val Ser Ala Ser Thr Ile Pro Glu Gln Ile Gln Ser Leu Ser
            420                 425                 430

Val His Asp Ser Gln Gly Pro Pro Asn Ala Asn Glu Asp Tyr Arg Glu
        435                 440                 445

Ala Ser Ser Cys Ala Val Asn Leu Val Leu Arg Leu Arg Asn Ser Arg
450                 455                 460

Lys Glu Leu Asn Asp Ile Arg Phe Glu Phe Thr Pro Gly Arg Asp Thr
```

```
              465                 470                 475                 480
Ala Asp Gly Val Ser Gln Glu Leu Phe Ser Ala Gly Leu Val Asp Gly
                    485                 490                 495

His Asp Val Val Ile Val Ala Ala Asn Leu Gln Lys Ile Val Asp Asp
                500                 505                 510

Pro Lys Ala Leu Lys Thr Leu Thr Phe Lys Leu Ala Ser Gly Cys Asp
            515                 520                 525

Gly Ser Glu Ile Pro Asp Glu Val Lys Leu Ile Gly Phe Ala Gln Leu
530                 535                 540

Ser Val Ser
545

<210> SEQ ID NO 31
<211> LENGTH: 577
<212> TYPE: PRT
<213> ORGANISM: human
<220> FEATURE:
<221> NAME/KEY: misc_feature
<222> LOCATION: (558)..(558)
<223> OTHER INFORMATION: Xaa can be any naturally occurring amino acid

<400> SEQUENCE: 31

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp
                85                  90                  95

Ile Thr Gln Arg Leu Phe Phe Leu Gln Val Lys Glu Gly Ile Leu Asn
            100                 105                 110

Asp Asp Ile Tyr Cys Pro Pro Glu Thr Ala Val Leu Leu Ala Ser Tyr
        115                 120                 125

Ala Val Gln Ser Lys Tyr Gly Asp Phe Asn Lys Glu Val His Lys Ser
    130                 135                 140

Gly Tyr Leu Ala Gly Asp Lys Leu Leu Pro Gln Arg Val Leu Glu Gln
145                 150                 155                 160

His Lys Leu Asn Lys Asp Gln Trp Glu Glu Arg Ile Gln Val Trp His
                165                 170                 175

Glu Glu His Arg Gly Met Leu Arg Glu Asp Ala Val Leu Glu Tyr Leu
            180                 185                 190

Lys Ile Ala Gln Asp Leu Glu Met Tyr Gly Val Asn Tyr Phe Ser Ile
        195                 200                 205

Lys Asn Lys Lys Gly Ser Glu Leu Trp Leu Gly Val Asp Ala Leu Gly
    210                 215                 220

Leu Asn Ile Tyr Glu Gln Asn Asp Arg Leu Thr Pro Lys Ile Gly Phe
225                 230                 235                 240

Pro Trp Ser Glu Ile Arg Asn Ile Ser Phe Asn Asp Lys Lys Phe Val
                245                 250                 255

Ile Lys Pro Ile Asp Lys Lys Ala Pro Asp Phe Val Phe Tyr Ala Pro
            260                 265                 270
```

```
Arg Leu Arg Ile Asn Lys Arg Ile Leu Ala Leu Cys Met Gly Asn His
        275                 280                 285
Glu Leu Tyr Met Arg Arg Lys Pro Asp Thr Ile Glu Val Gln Gln
    290                 295                 300
Met Lys Ala Gln Ala Arg Glu Glu Lys His Gln Lys Gln Met Glu Arg
305                 310                 315                 320
Ala Met Leu Glu Asn Glu Lys Lys Arg Glu Met Ala Glu Lys Glu
        325                 330                 335
Lys Glu Lys Ile Glu Arg Glu Lys Glu Leu Met Glu Arg Leu Lys
        340                 345                 350
Gln Ile Glu Glu Gln Thr Lys Lys Ala Gln Gln Glu Leu Glu Glu Gln
        355                 360                 365
Thr Arg Arg Ala Leu Glu Leu Glu Gln Glu Arg Lys Arg Ala Gln Ser
370                 375                 380
Glu Ala Glu Lys Leu Ala Lys Glu Arg Gln Ala Glu Glu Ala Lys
385                 390                 395                 400
Glu Ala Leu Leu Gln Ala Ser Arg Asp Gln Lys Thr Gln Glu Gln
        405                 410                 415
Leu Ala Leu Glu Met Ala Glu Leu Thr Ala Arg Ile Ser Gln Leu Glu
        420                 425                 430
Met Ala Arg Gln Lys Lys Glu Ser Glu Ala Val Glu Trp Gln Gln Lys
        435                 440                 445
Ala Gln Met Val Gln Glu Asp Leu Glu Lys Thr Arg Ala Glu Leu Lys
450                 455                 460
Thr Ala Met Ser Thr Pro His Val Ala Glu Pro Ala Glu Asn Glu Gln
465                 470                 475                 480
Asp Glu Gln Asp Glu Asn Gly Ala Glu Ala Ser Ala Asp Leu Arg Ala
                485                 490                 495
Asp Ala Met Ala Lys Asp Arg Ser Glu Glu Arg Thr Thr Glu Ala
                500                 505                 510
Glu Lys Asn Glu Arg Val Gln Lys His Leu Lys Ala Leu Thr Ser Glu
        515                 520                 525
Leu Ala Asn Ala Arg Asp Glu Ser Lys Lys Thr Ala Asn Asp Met Ile
        530                 535                 540
His Ala Glu Asn Met Arg Leu Gly Arg Asp Lys Tyr Lys Xaa Leu Arg
545                 550                 555                 560
Gln Ile Arg Gln Gly Asn Thr Lys Gln Arg Ile Asp Glu Phe Glu Ser
                565                 570                 575
Met

<210> SEQ ID NO 32
<211> LENGTH: 211
<212> TYPE: PRT
<213> ORGANISM: rat
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
```

```
<222> LOCATION: (144)..(144)
<223> OTHER INFORMATION: Xaa can be any naturally occurring amino acid

<400> SEQUENCE: 32

Met Ala Asp Glu Ser Ser Asp Ala Ala Gly Glu Pro Gln Pro Ala Pro
1               5                   10                  15

Ala Pro Val Arg Arg Ser Ser Ala Asn Tyr Arg Ala Tyr Ala Thr
            20                  25                  30

Glu Pro His Ala Lys Lys Ser Lys Ile Xaa Ala Xaa Arg Lys Leu
        35                  40                  45

Gln Leu Lys Thr Leu Met Leu Gln Ile Ala Lys Gln Glu Met Glu Arg
50                  55                  60

Glu Ala Glu Glu Arg Arg Gly Glu Lys Gly Arg Val Leu Xaa Thr Arg
65                  70                  75                  80

Cys Gln Pro Leu Val Leu Asp Gly Leu Gly Phe Glu Glu Leu Gln Asp
                85                  90                  95

Leu Cys Arg Gln Leu His Ala Arg Val Asp Lys Val Asp Glu Glu Arg
            100                 105                 110

Tyr Asp Val Glu Ala Lys Val Thr Lys Asn Ile Thr Glu Ile Ala Asp
        115                 120                 125

Leu Thr Gln Lys Ile Tyr Asp Leu Arg Gly Lys Phe Lys Arg Pro Xaa
130                 135                 140

Leu Arg Arg Val Arg Ile Ser Ala Asp Ala Met Met Gln Ala Leu Leu
145                 150                 155                 160

Gly Thr Arg Ala Lys Glu Ser Leu Asp Leu Arg Ala His Leu Lys Gln
                165                 170                 175

Val Lys Lys Glu Asp Ile Glu Lys Glu Asn Arg Glu Val Gly Asp Trp
            180                 185                 190

Arg Lys Asn Ile Asp Ala Leu Ser Gly Met Glu Gly Arg Lys Lys Lys
        195                 200                 205

Phe Glu Gly
    210

<210> SEQ ID NO 33
<211> LENGTH: 288
<212> TYPE: PRT
<213> ORGANISM: human
<220> FEATURE:
<221> NAME/KEY: misc_feature
<222> LOCATION: (194)..(194)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (284)..(284)
<223> OTHER INFORMATION: Xaa can be any naturally occurring amino acid

<400> SEQUENCE: 33

Met Ser Asp Ile Glu Glu Val Val Glu Glu Tyr Glu Glu Glu Glu Gln
1               5                   10                  15

Glu Glu Ala Ala Val Glu Glu Gln Glu Glu Ala Ala Glu Glu Asp Ala
            20                  25                  30

Glu Ala Glu Ala Glu Thr Glu Glu Thr Arg Ala Glu Glu Asp Glu Glu
        35                  40                  45

Glu Glu Glu Ala Lys Glu Ala Glu Asp Gly Pro Met Glu Glu Ser Lys
50                  55                  60
```

```
Pro Lys Pro Arg Ser Phe Met Pro Asn Leu Val Pro Pro Lys Ile Pro
 65                  70                  75                  80

Asp Gly Glu Arg Val Asp Phe Asp Asp Ile His Arg Lys Arg Met Glu
                 85                  90                  95

Lys Asp Leu Asn Glu Leu Gln Ala Leu Ile Glu Ala His Phe Glu Asn
            100                 105                 110

Arg Lys Lys Glu Glu Glu Leu Val Ser Leu Lys Asp Arg Ile Glu
            115                 120                 125

Lys Arg Arg Ala Glu Arg Ala Glu Gln Gln Arg Ile Arg Asn Glu Arg
            130                 135                 140

Glu Lys Glu Arg Gln Asn Arg Leu Ala Glu Arg Ala Arg Arg Glu
145                 150                 155                 160

Glu Glu Glu Asn Arg Arg Lys Ala Glu Asp Glu Ala Arg Lys Lys Lys
                165                 170                 175

Ala Leu Ser Asn Met Met His Phe Gly Gly Tyr Ile Gln Lys Gln Ala
            180                 185                 190

Gln Xaa Glu Arg Lys Ser Gly Lys Arg Gln Xaa Glu Arg Glu Lys Lys
    195                 200                 205

Lys Lys Ile Leu Ala Glu Arg Arg Lys Val Leu Ala Ile Asp His Leu
210                 215                 220

Asn Glu Asp Gln Leu Arg Glu Lys Ala Lys Glu Leu Trp Gln Thr Ile
225                 230                 235                 240

Tyr Asn Leu Glu Ala Glu Lys Phe Asp Leu Gln Glu Lys Phe Lys Gln
                245                 250                 255

Gln Lys Tyr Glu Ile Asn Val Leu Arg Asn Arg Ile Asn Asp Asn Gln
            260                 265                 270

Lys Val Ser Lys Thr Arg Gly Lys Ala Lys Val Xaa Gly Arg Trp Lys
275                 280                 285
```

<210> SEQ ID NO 34
<211> LENGTH: 92
<212> TYPE: PRT
<213> ORGANISM: rat
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid

<400> SEQUENCE: 34

```
Met Ala Pro Leu His His Ile Leu Ile Val Cys Val Cys Leu Leu Ser
 1               5                  10                  15

Met Ala Ser Ala Glu Ala Pro Gln Glu Pro Asp Pro Phe Thr Tyr Asp
                20                  25                  30

Tyr His Thr Leu Arg Ile Gly Gly Leu Thr Ala Gly Ile Leu Leu Phe
             35                  40                  45

Ile Leu Gly Ile Leu Ile Leu Ser Lys Arg Cys Arg Cys Lys Phe
         50                  55                  60

Asn Gln Gln Gln Arg Thr Gly Glu Pro Asp Glu Glu Glu Gly Thr Phe
 65                  70                  75                  80

Arg Ser Xaa Ile Arg Arg Leu Xaa Thr Arg Arg
                 85                  90
```

<210> SEQ ID NO 35
<211> LENGTH: 355

```
<212> TYPE: PRT
<213> ORGANISM: human
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 35

Met Gly Cys Arg Gln Ser Ser Glu Glu Lys Glu Ala Ala Arg Arg Xaa
1               5                   10                  15

Arg Arg Ile Asp Arg His Leu Arg Ser Glu Xaa Gln Arg Gln Arg Arg
            20                  25                  30

Glu Ile Lys Leu Leu Leu Leu Gly Thr Ser Asn Ser Gly Lys Ser Thr
        35                  40                  45

Ile Val Lys Gln Met Lys Ile Ile His Ser Gly Gly Phe Asn Leu Glu
50                  55                  60

Ala Cys Lys Glu Tyr Lys Pro Leu Ile Ile Tyr Asn Ala Ile Asp Ser
65                  70                  75                  80

Leu Thr Arg Ile Ile Arg Ala Leu Ala Ala Leu Arg Ile Asp Phe His
                85                  90                  95

Asn Pro Asp Arg Ala Tyr Asp Ala Val Gln Leu Phe Ala Leu Thr Gly
            100                 105                 110

Pro Ala Glu Ser Lys Gly Glu Ile Thr Pro Glu Leu Leu Gly Val Met
        115                 120                 125

Arg Arg Leu Trp Ala Asp Gln Gly Ala Gln Ala Cys Phe Ser Arg Ser
130                 135                 140

Ser Glu Tyr His Leu Glu Asp Asn Ala Ala Tyr Tyr Leu Asn Asp Leu
145                 150                 155                 160

Glu Arg Ile Ala Ala Ala Asp Tyr Ile Pro Thr Val Glu Asp Ile Leu
                165                 170                 175

Arg Ser Arg Asp Met Thr Thr Gly Ile Val Glu Asn Lys Phe Thr Phe
            180                 185                 190

Lys Glu Leu Thr Phe Lys Met Val Asp Val Gly Gly Gln Arg Ser Glu
        195                 200                 205

Arg Lys Lys Trp Ile His Cys Phe Glu Gly Val Thr Ala Ile Ile Phe
210                 215                 220

Cys Val Glu Leu Ser Gly Tyr Asp Leu Lys Leu Tyr Glu Asp Asn Gln
225                 230                 235                 240

Thr Ser Arg Met Ala Glu Ser Leu Arg Leu Phe Asp Ser Ile Cys Asn
                245                 250                 255

Asn Asn Trp Phe Ile Asn Thr Ser Leu Ile Leu Phe Leu Asn Lys Lys
            260                 265                 270

Asp Leu Leu Ala Glu Lys Ile Arg Arg Ile Pro Leu Thr Ile Cys Phe
        275                 280                 285

Pro Glu Tyr Lys Gly Gln Asn Thr Tyr Glu Glu Ala Ala Val Tyr Ile
290                 295                 300

Gln Arg Gln Phe Glu Asp Leu Asn Arg Asn Lys Glu Thr Lys Glu Ile
305                 310                 315                 320

Tyr Ser His Phe Thr Cys Ala Thr Asp Thr Ser Asn Ile Gln Phe Val
                325                 330                 335

Phe Asp Ala Val Thr Asp Val Ile Gln Asn Asn Leu Lys Tyr Ile
            340                 345                 350
```

-continued

```
Gly Leu Cys
        355

<210> SEQ ID NO 36
<211> LENGTH: 195
<212> TYPE: PRT
<213> ORGANISM: human
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid

<400> SEQUENCE: 36

Met Gly Ser Gln Ser Ser Lys Ala Pro Arg Gly Asp Val Thr Ala Glu
1               5                   10                  15

Glu Ala Ala Gly Ala Ser Pro Ala Lys Ala Asn Gly Gln Glu Asn Gly
                20                  25                  30

His Val Lys Ser Asn Gly Asp Leu Ser Pro Lys Gly Glu Gly Glu Ser
        35                  40                  45

Pro Pro Val Asn Gly Thr Asp Glu Ala Ala Gly Ala Thr Gly Asp Ala
    50                  55                  60

Ile Glu Pro Ala Pro Thr Ser Gln Gly Ala Glu Ala Lys Gly Glu Val
65                  70                  75                  80

Pro Pro Lys Glu Thr Pro Lys Lys Lys Lys Phe Xaa Phe Lys Lys
                85                  90                  95

Pro Phe Lys Leu Ser Gly Leu Xaa Phe Lys Arg Asn Arg Lys Glu Gly
            100                 105                 110

Gly Gly Asp Ser Ser Ala Ser Ser Pro Thr Glu Glu Glu Gln Glu Gln
        115                 120                 125

Gly Glu Ile Gly Ala Cys Ser Asp Glu Gly Thr Ala Gln Glu Gly Lys
    130                 135                 140

Ala Ala Ala Thr Pro Glu Ser Gln Glu Pro Gln Ala Lys Gly Ala Glu
145                 150                 155                 160

Ala Ser Ala Ala Ser Glu Glu Glu Ala Gly Pro Gln Ala Thr Glu Pro
                165                 170                 175

Ser Thr Pro Ser Gly Pro Glu Ser Gly Pro Thr Pro Ala Ser Ala Glu
            180                 185                 190

Gln Asn Glu
        195

<210> SEQ ID NO 37
<211> LENGTH: 206
<212> TYPE: PRT
<213> ORGANISM: human
<220> FEATURE:
<221> NAME/KEY: misc_feature
<222> LOCATION: (187)..(187)
<223> OTHER INFORMATION: Xaa can be any naturally occurring amino acid

<400> SEQUENCE: 37

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
        35                  40                  45
```

```
Met Leu Asp Glu Gln Gly Glu Gln Leu Asp Arg Val Glu Glu Gly Met
    50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Asp Glu Arg Gln Met Ala
            115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Xaa Asn Lys Thr Arg Ile
            180                 185                 190

Asp Glu Ala Asn Gln Arg Ala Thr Lys Met Leu Gly Ser Gly
            195                 200                 205

<210> SEQ ID NO 38
<211> LENGTH: 706
<212> TYPE: PRT
<213> ORGANISM: human
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (676)..(676)
<223> OTHER INFORMATION: Xaa can be any naturally occurring amino acid

<400> SEQUENCE: 38

Met Ser Pro Phe Leu Arg Ile Gly Leu Ser Asn Phe Asp Cys Gly Ser
1               5                   10                  15

Cys Gln Ser Cys Gln Gly Glu Ala Val Asn Pro Tyr Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu Met Ser Asp Thr
        115                 120                 125

Lys Asp Met Asn Glu Phe Glu Thr Glu Gly Phe Phe Ala Leu His Gln
    130                 135                 140

Arg Arg Gly Ala Ile Lys Gln Ala Lys Val His His Val Lys Cys His
145                 150                 155                 160

Glu Phe Thr Ala Thr Phe Phe Pro Gln Pro Thr Phe Cys Ser Val Cys
                165                 170                 175
```

His Glu Phe Val Trp Gly Leu Asn Lys Gln Gly Tyr Gln Cys Arg Gln
                180                 185                 190

Cys Asn Ala Ala Ile His Lys Lys Cys Ile Asp Lys Val Ile Ala Lys
            195                 200                 205

Cys Thr Gly Ser Ala Ile Asn Ser Arg Glu Xaa Met Phe His Lys Glu
210                 215                 220

Arg Phe Lys Ile Asp Met Pro His Arg Phe Lys Val Tyr Asn Tyr Lys
225                 230                 235                 240

Ser Pro Thr Phe Cys Glu His Cys Gly Thr Leu Leu Trp Gly Leu Ala
                245                 250                 255

Arg Gln Gly Leu Lys Cys Asp Ala Cys Gly Met Asn Val His His Arg
            260                 265                 270

Cys Gln Thr Lys Val Ala Asn Leu Cys Gly Ile Asn Gln Lys Leu Met
        275                 280                 285

Ala Glu Ala Leu Ala Met Ile Glu Ser Thr Gln Gln Ala Arg Cys Leu
    290                 295                 300

Arg Asp Thr Glu Gln Ile Phe Arg Glu Gly Pro Val Glu Ile Gly Leu
305                 310                 315                 320

Pro Cys Ser Ile Lys Asn Glu Ala Arg Pro Pro Cys Leu Pro Thr Pro
                325                 330                 335

Gly Lys Arg Glu Pro Gln Gly Ile Ser Trp Glu Ser Pro Leu Asp Glu
            340                 345                 350

Val Asp Lys Met Cys His Leu Pro Glu Pro Glu Leu Asn Lys Glu Arg
        355                 360                 365

Pro Ser Leu Gln Ile Lys Leu Lys Ile Glu Asp Phe Ile Leu His Lys
    370                 375                 380

Met Leu Gly Lys Gly Ser Phe Gly Lys Val Phe Leu Ala Glu Phe Lys
385                 390                 395                 400

Lys Thr Asn Gln Phe Phe Ala Ile Lys Ala Leu Lys Lys Asp Val Val
                405                 410                 415

Leu Met Asp Asp Asp Val Glu Cys Thr Met Val Glu Lys Arg Val Leu
            420                 425                 430

Ser Leu Ala Trp Glu His Pro Phe Leu Thr His Met Phe Cys Thr Phe
        435                 440                 445

Gln Thr Lys Glu Asn Leu Phe Phe Val Met Glu Tyr Leu Asn Gly Gly
    450                 455                 460

Asp Leu Met Tyr His Ile Gln Ser Cys His Lys Phe Asp Leu Ser Arg
465                 470                 475                 480

Ala Thr Phe Tyr Ala Ala Glu Ile Ile Leu Gly Leu Gln Phe Leu His
                485                 490                 495

Ser Lys Gly Ile Val Tyr Arg Asp Leu Lys Leu Asp Asn Ile Leu Leu
            500                 505                 510

Asp Lys Asp Gly His Ile Lys Ile Ala Asp Phe Gly Met Cys Lys Glu
        515                 520                 525

Asn Met Leu Gly Asp Ala Lys Thr Asn Thr Phe Cys Gly Thr Pro Asp
    530                 535                 540

Tyr Ile Ala Pro Glu Ile Leu Leu Gly Gln Lys Tyr Asn His Ser Val
545                 550                 555                 560

Asp Trp Trp Ser Phe Gly Val Leu Leu Tyr Glu Met Leu Ile Gly Gln
                565                 570                 575

Ser Pro Phe His Gly Gln Asp Glu Glu Glu Leu Phe His Ser Ile Arg
            580                 585                 590

Met Asp Asn Pro Phe Tyr Pro Arg Trp Leu Glu Lys Glu Ala Lys Asp 595                 600                 605
Leu Leu Val Lys Leu Phe Val Arg Glu Pro Glu Lys Arg Leu Gly Val
            610                 615                 620

Arg Gly Asp Ile Arg Gln His Pro Leu Phe Arg Glu Ile Asn Trp Glu
625                 630                 635                 640

Glu Leu Glu Arg Lys Glu Ile Asp Pro Pro Phe Arg Pro Lys Val Lys
                645                 650                 655

Ser Pro Phe Asp Cys Ser Asn Phe Asp Lys Glu Phe Leu Asn Glu Lys
            660                 665                 670

Pro Arg Leu Xaa Phe Ala Asp Arg Ala Leu Ile Asn Ser Met Asp Gln
        675                 680                 685

Asn Met Phe Arg Asn Phe Ser Phe Met Asn Pro Gly Met Glu Arg Leu
690                 695                 700

Ile Ser
705

<210> SEQ ID NO 39
<211> LENGTH: 158
<212> TYPE: PRT
<213> ORGANISM: mouse
<220> FEATURE:
<221> NAME/KEY: misc_feature
<222> LOCATION: (8)..(8)
<223> OTHER INFORMATION: Xaa can be any naturally occurring amino acid

<400> SEQUENCE: 39

Met Ala Ser Gln Lys Arg Pro Xaa Gln Arg Ser Lys Tyr Leu Ala Thr
1               5                   10                  15

Ala Ser Thr Met Asp His Ala Arg His Gly Phe Leu Pro Arg His Arg
            20                  25                  30

Asp Thr Gly Ile Leu Asp Ser Ile Gly Arg Phe Phe Ser Gly Asp Arg
        35                  40                  45

Gly Ala Pro Lys Arg Gly Ser Gly Lys Asp Ser His Thr Arg Thr Thr
    50                  55                  60

His Tyr Gly Ser Leu Pro Gln Lys Ser Gln His Gly Arg Thr Gln Asp
65                  70                  75                  80

Glu Asn Pro Val Val His Phe Phe Lys Asn Ile Val Thr Pro Arg Thr
                85                  90                  95

Pro Pro Pro Ser Gln Gly Lys Gly Ala Glu Gly Gln Lys Pro Gly Phe
            100                 105                 110

Gly Tyr Gly Gly Arg Ala Ser Asp Tyr Lys Ser Ala His Lys Gly Phe
        115                 120                 125

Lys Gly Ala Tyr Asp Ala Gln Gly Thr Leu Ser Lys Ile Phe Lys Leu
    130                 135                 140

Gly Gly Arg Asp Ser Arg Ser Gly Ser Pro Met Ala Arg Arg
145                 150                 155

<210> SEQ ID NO 40
<211> LENGTH: 78
<212> TYPE: PRT
<213> ORGANISM: human
<220> FEATURE:
<221> NAME/KEY: misc_feature
<222> LOCATION: (36)..(36)
<223> OTHER INFORMATION: Xaa can be any naturally occurring amino acid

<400> SEQUENCE: 40

Met Asp Cys Cys Thr Glu Asn Ala Cys Ser Lys Pro Asp Asp Asp Ile
1               5                   10                  15

Leu Asp Ile Pro Leu Asp Asp Pro Gly Ala Asn Ala Ala Ala Ala Lys
            20                  25                  30

Ile Gln Ala Xaa Phe Arg Gly His Met Ala Arg Lys Lys Ile Lys Ser
            35                  40                  45

Gly Glu Arg Gly Arg Lys Gly Pro Gly Pro Gly Pro Gly Pro Gly Ala
50                      55                  60

Gly Val Ala Arg Gly Gly Ala Gly Gly Pro Ser Gly Asp
65                  70                  75

<210> SEQ ID NO 41
<211> LENGTH: 146
<212> TYPE: PRT
<213> ORGANISM: viral
<220> FEATURE:
<221> NAME/KEY: misc_feature
<222> LOCATION: (118)..(118)
<223> OTHER INFORMATION: Xaa can be any naturally occurring amino acid

<400> SEQUENCE: 41

Pro Phe Tyr Gly Lys Ala Ile Pro Ile Glu Thr Ile Lys Gly Gly Arg
1               5                   10                  15

His Leu Ile Phe Cys His Ser Lys Lys Lys Cys Asp Glu Leu Ala Ala
            20                  25                  30

Lys Leu Ser Gly Leu Gly Leu Asn Ala Val Ala Tyr Tyr Arg Gly Leu
        35                      40                  45

Asp Val Ser Val Ile Pro Thr Ser Gly Asp Val Val Val Ala Thr
    50                  55                  60

Asp Ala Leu Met Thr Gly Phe Thr Gly Asp Phe Asp Ser Val Ile Asp
65                  70                  75                  80

Cys Asn Thr Cys Val Thr Gln Thr Val Asp Phe Ser Leu Asp Pro Thr
                85                  90                  95

Phe Thr Ile Glu Thr Thr Thr Val Pro Gln Asp Ala Val Ser Arg Ser
            100                 105                 110

Gln Arg Arg Gly Arg Xaa Gly Arg Gly Arg Gly Ile Tyr Arg Phe
        115                 120                 125

Val Thr Leu Gly Glu Arg Pro Ser Asp Met Phe Asp Ser Ser Val Leu
    130                 135                 140

Cys Glu
145

<210> SEQ ID NO 42
<211> LENGTH: 866
<212> TYPE: PRT
<213> ORGANISM: human
<220> FEATURE:
<221> NAME/KEY: misc_feature
<222> LOCATION: (618)..(618)
<223> OTHER INFORMATION: Xaa can be any naturally occurring amino acid

<400> SEQUENCE: 42

Met Phe Ser Met Arg Ile Val Cys Leu Val Leu Ser Val Val Gly Thr
1               5                   10                  15

Ala Trp Thr Ala Asp Ser Gly Glu Gly Asp Phe Leu Ala Glu Gly Gly
            20                  25                  30

Gly Val Arg Gly Pro Arg Val Val Glu Arg His Gln Ser Ala Cys Lys
        35                      40                  45

Asp Ser Asp Trp Pro Phe Cys Ser Asp Glu Asp Trp Asn Tyr Lys Cys
    50                  55                  60

-continued

```
Pro Ser Gly Cys Arg Met Lys Gly Leu Ile Asp Glu Val Asn Gln Asp
 65                  70                  75                  80

Phe Thr Asn Arg Ile Asn Lys Leu Lys Asn Ser Leu Phe Glu Tyr Gln
                 85                  90                  95

Lys Asn Asn Lys Asp Ser His Ser Leu Thr Thr Asn Ile Met Glu Ile
            100                 105                 110

Leu Arg Gly Asp Phe Ser Ser Ala Asn Asn Arg Asp Asn Thr Tyr Asn
        115                 120                 125

Arg Val Ser Glu Asp Leu Arg Ser Arg Ile Glu Val Leu Lys Arg Lys
    130                 135                 140

Val Ile Glu Lys Val Gln His Ile Gln Leu Leu Gln Lys Asn Val Arg
145                 150                 155                 160

Ala Gln Leu Val Asp Met Lys Arg Leu Glu Val Asp Ile Asp Ile Lys
                165                 170                 175

Ile Arg Ser Cys Arg Gly Ser Cys Ser Arg Ala Leu Ala Arg Glu Val
            180                 185                 190

Asp Leu Lys Asp Tyr Glu Asp Gln Gln Lys Gln Leu Glu Gln Val Ile
        195                 200                 205

Ala Lys Asp Leu Leu Pro Ser Arg Asp Arg Gln His Leu Pro Leu Ile
    210                 215                 220

Lys Met Lys Pro Val Pro Asp Leu Val Pro Gly Asn Phe Lys Ser Gln
225                 230                 235                 240

Leu Gln Lys Val Pro Pro Glu Trp Lys Ala Leu Thr Asp Met Pro Gln
                245                 250                 255

Met Arg Met Glu Leu Glu Arg Pro Gly Gly Asn Glu Ile Thr Arg Gly
            260                 265                 270

Gly Ser Thr Ser Tyr Gly Thr Gly Ser Glu Thr Glu Ser Pro Arg Asn
        275                 280                 285

Pro Ser Ser Ala Gly Ser Trp Asn Ser Gly Ser Ser Gly Pro Gly Ser
    290                 295                 300

Thr Gly Asn Arg Asn Pro Gly Ser Ser Gly Thr Gly Thr Ala Thr
305                 310                 315                 320

Trp Lys Pro Gly Ser Ser Gly Pro Gly Ser Thr Gly Ser Trp Asn Ser
                325                 330                 335

Gly Ser Ser Gly Thr Gly Ser Thr Gly Asn Gln Asn Pro Gly Ser Pro
            340                 345                 350

Arg Pro Gly Ser Thr Gly Thr Trp Asn Pro Gly Ser Ser Glu Arg Gly
        355                 360                 365

Ser Ala Gly His Trp Thr Ser Glu Ser Ser Val Ser Gly Ser Thr Gly
    370                 375                 380

Gln Trp His Ser Glu Ser Gly Ser Phe Arg Pro Asp Ser Pro Gly Ser
385                 390                 395                 400

Gly Asn Ala Arg Pro Asn Asn Pro Asp Trp Gly Thr Phe Glu Glu Val
                405                 410                 415

Ser Gly Asn Val Ser Pro Gly Thr Arg Arg Glu Tyr His Thr Glu Lys
            420                 425                 430

Leu Val Thr Ser Lys Gly Asp Lys Glu Leu Arg Thr Gly Lys Glu Lys
        435                 440                 445

Val Thr Ser Gly Ser Thr Thr Thr Arg Arg Ser Cys Ser Lys Thr
    450                 455                 460

Val Thr Lys Thr Val Ile Gly Pro Asp Gly His Lys Glu Val Thr Lys
465                 470                 475                 480

Glu Val Val Thr Ser Glu Asp Gly Ser Asp Cys Pro Glu Ala Met Asp
```

485                 490                 495
Leu Gly Thr Leu Ser Gly Ile Gly Thr Leu Asp Gly Phe Arg His Arg
            500                 505                 510

His Pro Asp Glu Ala Ala Phe Phe Asp Thr Ala Ser Thr Gly Lys Thr
            515                 520                 525

Phe Pro Gly Phe Phe Ser Pro Met Leu Gly Glu Phe Val Ser Glu Thr
            530                 535                 540

Glu Ser Arg Gly Ser Glu Ser Gly Ile Phe Thr Asn Thr Lys Glu Ser
545                 550                 555                 560

Ser Ser His His Pro Gly Ile Ala Glu Phe Pro Ser Arg Gly Lys Ser
                565                 570                 575

Ser Ser Tyr Ser Lys Gln Phe Thr Ser Ser Thr Ser Tyr Asn Arg Gly
            580                 585                 590

Asp Ser Thr Phe Glu Ser Lys Ser Tyr Lys Met Ala Asp Glu Ala Gly
            595                 600                 605

Ser Glu Ala Asp His Glu Gly Thr His Xaa Thr Lys Arg Gly His Ala
            610                 615                 620

Lys Ser Arg Pro Val Arg Asp Cys Asp Val Leu Gln Thr His Pro
625                 630                 635                 640

Ser Gly Thr Gln Ser Gly Ile Phe Asn Ile Lys Leu Pro Gly Ser Ser
                645                 650                 655

Lys Ile Phe Ser Val Tyr Cys Asp Gln Glu Thr Ser Leu Gly Gly Trp
            660                 665                 670

Leu Leu Ile Gln Gln Arg Met Asp Gly Ser Leu Asn Phe Asn Arg Thr
            675                 680                 685

Trp Gln Asp Tyr Lys Arg Gly Phe Gly Ser Leu Asn Asp Glu Gly Glu
            690                 695                 700

Gly Glu Phe Trp Leu Gly Asn Asp Tyr Leu His Leu Leu Thr Gln Arg
705                 710                 715                 720

Gly Ser Val Leu Arg Val Glu Leu Glu Asp Trp Ala Gly Asn Glu Ala
                725                 730                 735

Tyr Ala Glu Tyr His Phe Arg Val Gly Ser Glu Ala Glu Gly Tyr Ala
            740                 745                 750

Leu Gln Val Ser Ser Tyr Glu Gly Thr Ala Gly Asp Ala Leu Ile Glu
            755                 760                 765

Gly Ser Val Glu Glu Gly Ala Glu Tyr Thr Ser His Asn Asn Met Gln
            770                 775                 780

Phe Ser Thr Phe Asp Arg Asp Ala Asp Gln Trp Glu Glu Asn Cys Ala
785                 790                 795                 800

Glu Val Tyr Gly Gly Gly Trp Trp Tyr Asn Asn Cys Gln Ala Ala Asn
                805                 810                 815

Leu Asn Gly Ile Tyr Tyr Pro Gly Gly Ser Tyr Asp Pro Arg Asn Asn
            820                 825                 830

Ser Pro Tyr Glu Ile Glu Asn Gly Val Val Trp Val Ser Phe Arg Gly
            835                 840                 845

Ala Asp Tyr Ser Leu Arg Ala Val Arg Met Lys Ile Arg Pro Leu Val
            850                 855                 860

Thr Gln
865

<210> SEQ ID NO 43
<211> LENGTH: 11
<212> TYPE: PRT
<213> ORGANISM: artificial sequence

```
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 43

Gln Lys Arg Pro Xaa Gln Arg Ser Lys Tyr Leu
1               5                   10

<210> SEQ ID NO 44
<211> LENGTH: 16
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 44

Ala Ala Lys Ile Gln Ala Xaa Phe Arg Gly His Met Ala Arg Lys Lys
1               5                   10                  15

<210> SEQ ID NO 45
<211> LENGTH: 23
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 45

Arg Arg Gly Arg Xaa Gly Arg Gly Arg Arg Gly Ile Phe Arg His Glu
1               5                   10                  15

Gly Thr His Ala Thr Lys Arg
            20

<210> SEQ ID NO 46
<211> LENGTH: 13
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 46

Pro Leu Ser Arg Thr Leu Xaa Gln Arg Ser Lys Tyr Leu
1               5                   10

<210> SEQ ID NO 47
<211> LENGTH: 37
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Xaa can be any naturally occurring amino acid

<400> SEQUENCE: 47
```

```
Gly Asn Glu Ile Asp Thr Gln Asn Arg Gln Ile Asp Arg Ile Met Glu
1               5                   10                  15

Lys Ala Asp Xaa Asn Lys Thr Arg Ile Asp Glu Ala Asn Gln Arg Ala
            20                  25                  30

Thr Lys Met Leu Gly
        35

<210> SEQ ID NO 48
<211> LENGTH: 31
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (27)..(27)
<223> OTHER INFORMATION: Xaa can be any naturally occurring amino acid

<400> SEQUENCE: 48

Ala Leu Ser Asn Met Met His Phe Gly Gly Tyr Ile Gln Lys Gln Ala
1               5                   10                  15

Gln Xaa Glu Arg Lys Ser Gly Lys Arg Gln Xaa Glu Arg Glu Lys
            20                  25                  30

<210> SEQ ID NO 49
<211> LENGTH: 37
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid

<400> SEQUENCE: 49

Ile Thr Glu Ile Ala Asp Leu Thr Gln Lys Ile Tyr Asp Leu Arg Gly
1               5                   10                  15

Lys Phe Lys Arg Pro Xaa Leu Arg Arg Val Arg Ile Ser Ala Asp Ala
            20                  25                  30

Met Met Gln Ala Leu
        35

<210> SEQ ID NO 50
<211> LENGTH: 20
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 50

Gly Gly Arg Leu Pro Gly Tyr Arg His Xaa Ala Phe Val Pro Thr His
1               5                   10                  15

Ser Tyr Pro Glu
        20

<210> SEQ ID NO 51
```

```
<211> LENGTH: 19
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: Xaa can be any naturally occurring amino acid

<400> SEQUENCE: 51

Asn Leu His Thr Asp Asp Gly Tyr Met Pro Met Xaa Pro Gly Val Ala
1               5                   10                  15

Pro Val Pro

<210> SEQ ID NO 52
<211> LENGTH: 24
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa can be any naturally occurring amino acid

<400> SEQUENCE: 52

Gly Val Glu Asp Lys Glu Met Met Lys Lys Tyr Gly Lys Xaa Phe Arg
1               5                   10                  15

Lys Leu Leu Ser Leu Cys Leu Gln
            20

<210> SEQ ID NO 53
<211> LENGTH: 26
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (18)..(18)
<223> OTHER INFORMATION: Xaa can be any naturally occurring amino acid

<400> SEQUENCE: 53

Asn Asp Met Ile His Ala Glu Asn Met Arg Leu Gly Arg Asp Lys Tyr
1               5                   10                  15

Lys Xaa Leu Arg Gln Ile Arg Gln Gly Asn
            20                  25

<210> SEQ ID NO 54
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 54

Glu Lys Arg Pro Xaa Gln Arg Ser Lys Tyr Leu
1               5                   10

<210> SEQ ID NO 55
<211> LENGTH: 9
<212> TYPE: PRT
<213> ORGANISM: artificial sequence
```

```
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 55

His Glu Gly Thr His Xaa Thr Lys Arg
1               5

<210> SEQ ID NO 56
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 56

Pro Leu Ser Arg Thr Leu Xaa Val Ser Ser
1               5                   10

<210> SEQ ID NO 57
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 57

Ala Tyr Phe Leu Tyr Xaa Arg Lys Thr Gly Gly
1               5                   10

<210> SEQ ID NO 58
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 58

Met Arg Glu Asp Xaa Ala Arg Val
1               5

<210> SEQ ID NO 59
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 59

Leu Met Gln Gln Gln Lys Xaa Phe Arg
1               5
```

```
<210> SEQ ID NO 60
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 60

Leu Glu Ile Asn Arg Ala Asp Xaa Lys Leu Asn
1               5                   10

<210> SEQ ID NO 61
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 61

Ala Thr Lys Ile Gln Ala Xaa Phe Arg Gly
1               5                   10

<210> SEQ ID NO 62
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 62

Ala Arg Pro Gly Xaa Arg Gly Pro Ala
1               5

<210> SEQ ID NO 63
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 63

Val Tyr Gly Ile Glu Xaa Val Lys Ile
1               5

<210> SEQ ID NO 64
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(7)
```

<223> OTHER INFORMATION: Xaa can be any naturally occurring amino acid

<400> SEQUENCE: 64

Phe Lys Arg Arg Arg Xaa Xaa Lys Asp
1               5

<210> SEQ ID NO 65
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 65

Lys Arg Phe Xaa Phe Lys Lys Xaa Phe Lys Leu
1               5                   10

<210> SEQ ID NO 66
<211> LENGTH: 15
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 66

Phe Lys Lys Xaa Phe Lys Leu Ser Gly Phe Ser Phe Lys Lys Asn
1               5                   10                  15

<210> SEQ ID NO 67
<211> LENGTH: 12
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 67

Glu Thr Pro Lys Lys Lys Lys Lys Arg Phe Xaa Phe
1               5                   10

<210> SEQ ID NO 68
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 68

Asp Asn Leu Leu Pro Met Xaa Pro Glu
1               5

```
<210> SEQ ID NO 69
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 69

Val Leu Gly Arg Arg Xaa Phe Glu Gly
1               5

<210> SEQ ID NO 70
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 70

Ala Tyr Trp Glu Lys Xaa Phe Lys Ile
1               5

<210> SEQ ID NO 71
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 71

Glu His Gln Arg Pro Xaa Leu Arg Pro
1               5

<210> SEQ ID NO 72
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 72

Gly Val Lys Thr Xaa Gly Lys Val
1               5

<210> SEQ ID NO 73
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
```

```
<220> FEATURE:
<221> NAME/KEY: misc_feature
<222> LOCATION: (9)..(9)
<223> OTHER INFORMATION: Xaa can be any naturally occurring amino acid

<400> SEQUENCE: 73

Met Lys Arg Pro Ser Xaa Val Lys Xaa Leu Arg
1               5                   10

<210> SEQ ID NO 74
<211> LENGTH: 23
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 74

Leu Glu Arg Arg Ser Val Arg Met Lys Arg Pro Ser Xaa Val Lys Xaa
1               5                   10                  15

Leu Arg Ser Glu Arg Leu Ile
            20

<210> SEQ ID NO 75
<211> LENGTH: 28
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 75

Tyr Ile Pro Gly Ala Thr Met Gly Thr Xaa Pro Ala Leu Thr Gly Asp
1               5                   10                  15

Glu Ala Ala Gly Ala Ala Asp Leu Asp Asn Arg Phe
            20                  25

<210> SEQ ID NO 76
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 76

Ala Thr Met Gly Thr Xaa Pro Ala Leu
1               5

<210> SEQ ID NO 77
<211> LENGTH: 27
<212> TYPE: PRT
<213> ORGANISM: artificial sequence
<220> FEATURE:
<223> OTHER INFORMATION: Synthetic
<220> FEATURE:
```

```
<221> NAME/KEY: misc_feature
<222> LOCATION: (7)..(7)
<223> OTHER INFORMATION: Xaa can be any naturally occurring amino acid

<400> SEQUENCE: 77

Leu Pro Gly Tyr Arg His Xaa Ala Phe Val Pro Thr His Ser Tyr Pro
1               5                   10                  15

Glu Glu Gly Leu Glu Met His His Leu Glu Arg
            20                  25

<210> SEQ ID NO 78
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 78

Gly Tyr Arg His Xaa Ala Phe Val
1               5

<210> SEQ ID NO 79
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 79

Asp Asp Gly Tyr Met Pro Met Xaa Pro Gly Val
1               5                   10

<210> SEQ ID NO 80
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 80

Gly Tyr Met Pro Met Xaa Pro Gly
1               5

<210> SEQ ID NO 81
<211> LENGTH: 14
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Xaa can be any naturally occurring amino acid

<400> SEQUENCE: 81

Thr Ala Xaa Leu Thr Ser Ala Ala Ser Ile Asp Gly Ser Arg
1               5                   10
```

```
<210> SEQ ID NO 82
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 82

Leu Ser Arg Ser Arg Thr Ala Xaa Leu Thr
1               5                   10

<210> SEQ ID NO 83
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 83

Tyr Gln Glu Glu Arg Arg Xaa Val Lys
1               5

<210> SEQ ID NO 84
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 84

Lys Tyr Gly Lys Xaa Phe Arg Lys Leu
1               5

<210> SEQ ID NO 85
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 85

Lys Tyr Gly Lys Xaa Phe Arg
1               5

<210> SEQ ID NO 86
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (4)..(4)
```

```
<223> OTHER INFORMATION: Xaa can be any naturally occurring amino acid

<400> SEQUENCE: 86

Lys Tyr Lys Xaa Leu Arg Gln Ile Arg
1               5

<210> SEQ ID NO 87
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 87

Gly Arg Val Leu Xaa Thr Arg Cys Gln
1               5

<210> SEQ ID NO 88
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 88

Gly Lys Phe Lys Arg Pro Xaa Leu Arg
1               5

<210> SEQ ID NO 89
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 89

Gln Lys Gln Ala Gln Xaa Glu Arg
1               5

<210> SEQ ID NO 90
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 90

Gly Lys Arg Gln Xaa Glu Arg
1               5

<210> SEQ ID NO 91
<211> LENGTH: 9
<212> TYPE: PRT
```

```
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 91

Gly Lys Ala Lys Val Xaa Gly Arg Trp
1               5

<210> SEQ ID NO 92
<211> LENGTH: 18
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 92

Lys Gln Ala Gln Xaa Glu Arg Lys Ser Gly Lys Arg Gln Xaa Glu Arg
1               5                   10                  15

Glu Lys

<210> SEQ ID NO 93
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 93

Ile Arg Arg Leu Xaa Thr Arg Arg Arg
1               5

<210> SEQ ID NO 94
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 94

Gly Thr Phe Arg Ser Xaa Ile Arg
1               5

<210> SEQ ID NO 95
<211> LENGTH: 20
<212> TYPE: PRT
<213> ORGANISM: artificial sequence
<220> FEATURE:
<223> OTHER INFORMATION: Synthetic
<220> FEATURE:
<221> NAME/KEY: misc_feature
```

```
<222> LOCATION: (13)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 95

Gly Glu Pro Asp Glu Glu Gly Thr Phe Arg Ser Xaa Ile Arg Arg
1               5                   10                  15

Leu Xaa Thr Arg
            20

<210> SEQ ID NO 96
<211> LENGTH: 17
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 96

Ala Arg Arg Xaa Arg Arg Ile Asp Arg His Leu Arg Ser Glu Xaa Gln
1               5                   10                  15

Arg

<210> SEQ ID NO 97
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 97

Arg His Leu Arg Ser Glu Xaa Gln Arg
1               5

<210> SEQ ID NO 98
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 98

Glu Lys Glu Ala Ala Arg Arg Xaa Arg
1               5

<210> SEQ ID NO 99
<211> LENGTH: 35
<212> TYPE: PRT
<213> ORGANISM: artificial sequence
<220> FEATURE:
<223> OTHER INFORMATION: Synthetic
```

```
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 99

Gly Cys Arg Gln Ser Ser Glu Glu Lys Glu Ala Ala Arg Arg Xaa Arg
1               5                   10                  15

Arg Ile Asp Arg His Leu Arg Ser Glu Xaa Gln Arg Gln Arg Glu
            20                  25                  30

Ile Lys Leu
        35

<210> SEQ ID NO 100
<211> LENGTH: 22
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 100

Lys Lys Lys Phe Xaa Phe Lys Lys Pro Phe Lys Leu Ser Gly Leu Xaa
1               5                   10                  15

Phe Lys Arg Asn Arg Lys
            20

<210> SEQ ID NO 101
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 101

Pro Phe Lys Leu Ser Gly Leu Xaa Phe Lys
1               5                   10

<210> SEQ ID NO 102
<211> LENGTH: 12
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 102

Glu Thr Pro Lys Lys Lys Lys Lys Phe Xaa Phe Lys
1               5                   10
```

```
<210> SEQ ID NO 103
<211> LENGTH: 8
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 103

Met Glu Lys Ala Asp Xaa Asn Lys
1               5

<210> SEQ ID NO 104
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 104

Gly Ser Ala Ile Asn Ser Arg Glu Xaa Met
1               5                   10

<210> SEQ ID NO 105
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 105

Leu Asn Glu Lys Pro Arg Leu Xaa Phe Ala
1               5                   10

<210> SEQ ID NO 106
<211> LENGTH: 8
<212> TYPE: PRT
<213> ORGANISM: artificial sequence
<220> FEATURE:
<223> OTHER INFORMATION: Synthetic

<400> SEQUENCE: 106

Arg Lys Arg Thr Leu Arg Arg Leu
1               5

<210> SEQ ID NO 107
<211> LENGTH: 9
<212> TYPE: PRT
<213> ORGANISM: artificial sequence
<220> FEATURE:
<223> OTHER INFORMATION: Synthetic

<400> SEQUENCE: 107

Phe Ala Arg Lys Gly Ala Leu Arg Gln
1               5

<210> SEQ ID NO 108
<211> LENGTH: 9
```

<212> TYPE: PRT
<213> ORGANISM: artificial sequence
<220> FEATURE:
<223> OTHER INFORMATION: Synthetic

<400> SEQUENCE: 108

Ser Leu Asn Pro Glu Trp Asn Glu Thr
1               5

<210> SEQ ID NO 109
<211> LENGTH: 8
<212> TYPE: PRT
<213> ORGANISM: artificial sequence
<220> FEATURE:
<223> OTHER INFORMATION: Synthetic

<400> SEQUENCE: 109

Lys Gln Lys Thr Lys Thr Ile Lys
1               5

<210> SEQ ID NO 110
<211> LENGTH: 13
<212> TYPE: PRT
<213> ORGANISM: artificial sequence
<220> FEATURE:
<223> OTHER INFORMATION: Synthetic

<400> SEQUENCE: 110

Met Asp Pro Asn Gly Leu Ser Asp Pro Tyr Val Lys Leu
1               5                   10

<210> SEQ ID NO 111
<211> LENGTH: 8
<212> TYPE: PRT
<213> ORGANISM: artificial sequence
<220> FEATURE:
<223> OTHER INFORMATION: Synthetic

<400> SEQUENCE: 111

Cys Arg Leu Val Leu Ala Ser Cys
1               5

<210> SEQ ID NO 112
<211> LENGTH: 10
<212> TYPE: PRT
<213> ORGANISM: artificial sequence
<220> FEATURE:
<223> OTHER INFORMATION: Synthetic

<400> SEQUENCE: 112

Ser Phe Asn Ser Tyr Glu Leu Gly Ser Leu
1               5                   10

<210> SEQ ID NO 113
<211> LENGTH: 8
<212> TYPE: PRT
<213> ORGANISM: artificial sequence
<220> FEATURE:
<223> OTHER INFORMATION: Synthetic

<400> SEQUENCE: 113

Glu Ala Val Ser Leu Lys Pro Thr
1               5

<210> SEQ ID NO 114
<211> LENGTH: 8
<212> TYPE: PRT

```
<213> ORGANISM: artificial sequence
<220> FEATURE:
<223> OTHER INFORMATION: Synthetic

<400> SEQUENCE: 114

Glu Ala Val Gly Leu Gln Pro Thr
1               5

<210> SEQ ID NO 115
<211> LENGTH: 18
<212> TYPE: PRT
<213> ORGANISM: artificial sequence
<220> FEATURE:
<223> OTHER INFORMATION: Synthetic

<400> SEQUENCE: 115

Leu His Gln Arg Arg Gly Ala Ile Lys Gln Ala Lys Val His His Val
1               5                   10                  15

Lys Cys

<210> SEQ ID NO 116
<211> LENGTH: 13
<212> TYPE: PRT
<213> ORGANISM: artificial sequence
<220> FEATURE:
<223> OTHER INFORMATION: Synthetic

<400> SEQUENCE: 116

Ser Ile Tyr Arg Arg Gly Ala Arg Arg Trp Arg Lys Leu
1               5                   10

<210> SEQ ID NO 117
<211> LENGTH: 8
<212> TYPE: PRT
<213> ORGANISM: artificial sequence
<220> FEATURE:
<223> OTHER INFORMATION: Synthetic

<400> SEQUENCE: 117

Arg Lys Arg Cys Leu Arg Arg Leu
1               5

<210> SEQ ID NO 118
<211> LENGTH: 8
<212> TYPE: PRT
<213> ORGANISM: artificial sequence
<220> FEATURE:
<223> OTHER INFORMATION: Synthetic

<400> SEQUENCE: 118

Arg Lys Arg Tyr Leu Arg Arg Leu
1               5

<210> SEQ ID NO 119
<211> LENGTH: 8
<212> TYPE: PRT
<213> ORGANISM: artificial sequence
<220> FEATURE:
<223> OTHER INFORMATION: Synthetic

<400> SEQUENCE: 119

Arg Lys Arg Thr Leu Arg Arg Leu
1               5

<210> SEQ ID NO 120
<211> LENGTH: 8
```

```
<212> TYPE: PRT
<213> ORGANISM: artificial sequence
<220> FEATURE:
<223> OTHER INFORMATION: Synthetic

<400> SEQUENCE: 120

Arg Lys Arg Asp Leu Arg Arg Leu
1               5

<210> SEQ ID NO 121
<211> LENGTH: 8
<212> TYPE: PRT
<213> ORGANISM: artificial sequence
<220> FEATURE:
<223> OTHER INFORMATION: Synthetic

<400> SEQUENCE: 121

Arg Lys Arg Glu Leu Arg Arg Leu
1               5

<210> SEQ ID NO 122
<211> LENGTH: 8
<212> TYPE: PRT
<213> ORGANISM: artificial sequence
<220> FEATURE:
<223> OTHER INFORMATION: Synthetic

<400> SEQUENCE: 122

Arg Lys Arg Ala Leu Arg Arg Leu
1               5

<210> SEQ ID NO 123
<211> LENGTH: 7
<212> TYPE: PRT
<213> ORGANISM: artificial sequence
<220> FEATURE:
<223> OTHER INFORMATION: Synthetic

<400> SEQUENCE: 123

Leu Ala Val Phe His Asp Ala
1               5
```